United States Patent
Lee et al.

(10) Patent No.: US 8,106,031 B2
(45) Date of Patent: *Jan. 31, 2012

(54) HYDROLYTICALLY-RESISTANT BORON-CONTAINING THERAPEUTICS AND METHODS OF USE

(75) Inventors: Ving Lee, Los Altos, CA (US); Jacob J. Plattner, Berkeley, CA (US); Stephen J. Benkovic, State College, PA (US); Stephen J. Baker, Mountain View, CA (US); Kirk R. Maples, San Jose, CA (US); Carolyn Bellinger-Kawahara, Redwood City, CA (US); Tsutomu Akama, Sunnyvale, CA (US); Yong-Kang Zhang, San Jose, CA (US); Rajeshwar Singh, Edmonton (CA); Vittorio A. Sauro, Edmonton (CA)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/743,665

(22) Filed: May 2, 2007

(65) Prior Publication Data

US 2007/0265226 A1 Nov. 15, 2007

Related U.S. Application Data

(60) Provisional application No. 60/813,623, filed on May 2, 2006.

(51) Int. Cl.
*C07F 5/02* (2006.01)
*A61K 31/69* (2006.01)
*A61P 31/00* (2006.01)

(52) U.S. Cl. .......................... 514/64; 558/288
(58) Field of Classification Search ........................ None
See application file for complete search history.

(56) References Cited

U.S. PATENT DOCUMENTS

| 3,873,279 A * | 3/1975 | Singer ............................ 44/314 |
| 4,602,011 A | 7/1986 | West et al. |
| 4,766,113 A | 8/1988 | West et al. |
| 5,880,188 A | 3/1999 | Austin et al. |
| 7,465,836 B2 * | 12/2008 | Lee et al. ............................ 568/8 |
| 2005/0054644 A1 * | 3/2005 | Lee et al. ........................ 514/242 |
| 2006/0234981 A1 * | 10/2006 | Baker et al. ..................... 514/64 |
| 2007/0155699 A1 | 7/2007 | Baker et al. |
| 2007/0286822 A1 | 12/2007 | Sanders et al. |

FOREIGN PATENT DOCUMENTS

| CA | 2225014 | 6/1999 |
| WO | WO 9553745 | 12/1995 |
| WO | WO 03033002 | 4/2003 |
| WO | WO 2005/013892 * | 2/2005 |
| WO | WO 2005013892 | 2/2005 |
| WO | WO 2006079843 A1 | 8/2006 |
| WO | WO 2007095638 A2 | 8/2007 |
| WO | WO 2008157726 A1 | 12/2008 |
| WO | WO 2010045503 A | 4/2010 |
| WO | WO 2010045505 A1 | 4/2010 |

OTHER PUBLICATIONS

Haynes et al., Chemical Abstracts, 61:92418, 1964.*
Chemical Abstracts Registry No. 845302-09-2, entered Registry file on STN on Mar. 11, 2005.*
Haynes, R.R. et al. "Aryboronic Acids. VIII. Reactions of Boronphthalide" *J. Org. Chem.* (1964) 29(11):3229-33.
Li, W., "An Improved Protocol for Preparation of 3-Pyridyl- and Some Arylboronic Acids", *J. Org. Chem.* (2002) 67:5394-5397.
Koster, et al. "Cyclisierugen von Bor-Stickstoff-Verbindungen in der Hietz" *Liebigs Ann. Chem.* (1968) 720:23-31.
Zhdankin, et al. "Synthesis and Structure of Benzoboroxoles: Novel Organoboron Heterocycles" *Tetrahedron Letters* (1999) 40:6705-6708.
Genaev, et al., "Intramolecular Borylation Reaction Catalyzed by Lewis acid: Preparation of 1*H*-2,1-benzazaborole Derivatives", Chemical Communications, 2000, vol. 17: pp. 1587-1588.
Lennarz, et al., "Arylboronic Acids IV. Reactions of Boronophthalide", Journal of the American Chemical Society, May 1960, vol. 82; pp. 2172-2175.

* cited by examiner

*Primary Examiner* — Fiona T Powers
(74) *Attorney, Agent, or Firm* — Morgan, Lewis & Bockius LLP

(57) ABSTRACT

Compositions and methods of use of boron derivatives, including benzoxaboroles, benzazaboroles and benzthiaboroles, as therapeutic agents for treatment of diseases caused by fungi, yeast, bacteria or viruses are disclosed, as well as methods for synthesis of said agents and compositions thereof.

23 Claims, No Drawings

HYDROLYTICALLY-RESISTANT BORON-CONTAINING THERAPEUTICS AND METHODS OF USE

CROSS-REFERENCE TO RELATED APPLICATIONS

This application claims priority to U.S. Provisional Patent Application No. 60/813,623 filed May 2, 2006, which is incorporated herein by reference in its entirety for all purposes.

FIELD OF THE INVENTION

The present invention relates to novel compounds and compositions which have selective therapeutic activities, processes for making such compounds, synthetic intermediates employed in these processes and a method for treating human or other mammal in need of medical treatments.

BACKGROUND OF THE INVENTION

Infections of the nail and hoof, known as ungual and/or periungual infections, pose serious problems in dermatology. These ungual and/or periungual can be caused by sources such as fungi, viruses, yeast, bacteria and parasites. Onychomycosis is an example of these serious ungual and/or periungual infections and is caused by at least one fungus. Current treatment for ungual and/or periungual infections generally falls into three categories: systemic administration of medicine; surgical removal of all or part of the nail or hoof followed by topical treatment of the exposed tissue; or topical application of conventional creams, lotions, gels or solutions, frequently including the use of bandages to keep these dosage forms in place on the nail or hoof. All of these approaches have major drawbacks. The following discussion is particularly directed to drawbacks associated with current treatment of ungual and/or periungual antifungal infections.

Long term systemic (oral) administration of an antifungal agent for the treatment of onychomycosis is often required to produce a therapeutic effect in the nail bed. For example, oral treatment with the antifungal compound ketoconozole typically requires administration of 200 to 400 mg/day for 6 months before any significant therapeutic benefit is realized. Such long term, high dose systemic therapy can have significant adverse effects. For example, ketoconozole has been reported to have liver toxicity effects and reduces testosterone levels in blood due to adverse effects on the testes. Patient compliance is a problem with such long term therapies especially those which involve serious adverse effects. Moreover, this type of long term oral therapy is inconvenient in the treatment of a horse or other ruminants afflicted with fungal infections of the hoof. Accordingly, the risks associated with parenteral treatments generate significant disincentive against their use and considerable patient non-compliance.

Surgical removal of all or part of the nail followed by topical treatment also has severe drawbacks. The pain and discomfort associated with the surgery and the undesirable cosmetic appearance of the nail or nail bed represent significant problems, particularly for female patients or those more sensitive to physical appearance. Generally, this type of treatment is not realistic for ruminants such as horses.

Topical therapy has significant problems too. Topical dosage forms such as creams, lotions, gels etc., can not keep the drug in intimate contact with the infected area for therapeutically effective periods of time. Bandages have been used to hold drug reservoirs in place in an attempt to enhance absorption of the pharmaceutical agent. However the bandages are thick, awkward, troublesome and generally lead to poor patient compliance.

Hydrophilic and hydrophobic film forming topical antifungal solutions have also been developed. These dosage forms provide improved contact between the drug and the nail, but the films are not occlusive. Topical formulations for fungal infection treatment have largely tried to deliver the drug to the target site (an infected nail bed) by diffusion across or through the nail.

Nail is more like hair than stratum corneum with respect to chemical composition and permeability. Nitrogen is the major component of the nail attesting to the nail's proteinaceous nature. The total lipid content of mature nail is 0.1-1.0%, while the stratum corneum lipid is about 10% w/w. The nail is 100-200 times thicker than the stratum corneum and has a very high affinity and capacity for binding and retaining antifungal drugs. Consequently little if any drug penetrates through the nail to reach the target site. Because of these reasons topical therapy for fungal infections have generally been ineffective.

Compounds known as penetration or permeation enhancers are well known in the art to produce an increase in the permeability of skin or other body membranes to a pharmacologically active agent. The increased permeability allows an increase in the rate at which the drug permeates through the skin and enters the blood stream. Penetration enhancers have been successful in overcoming the impermeability of pharmaceutical agents through the skin. However, the thin stratum corneum layer of the skin, which is about 10 to 15 cells thick and is formed naturally by cells migrating toward the skin surface from the basal layer, has been easier to penetrate than nails. Moreover, known penetration enhancers have not proven to be useful in facilitating drug migration through the nail tissue.

Antimicrobial compositions for controlling bacterial and fungal infections comprising a metal chelate of 8-hydroxyquinoline and an alkyl benzene sulfonic acid have been shown to be efficacious due to the increased ability of the oleophilic group to penetrate the lipoid layers of micro-cells. The compounds however, do not effectively increase the ability to carry the pharmaceutically active antifungal through the cornified layer or stratum corneum of the skin. U.S. Pat. No. 4,602,011, West et al., Jul. 22, 1986; U.S. Pat. No. 4,766,113, West et al., Aug. 23, 1988.

Therefore, there is a need in the art for compounds which can effectively penetrate the nail. There is also need in the art for compounds which can effectively treat ungual and/or periungual infections. These and other needs are addressed by the current invention.

BRIEF SUMMARY OF THE INVENTION

In one aspect, the present invention relates to therapeutic compounds, which are boron-containing. These compounds include structures that encompass benzoxaboroles, benzazaboroles, benzthiaboroles and related analogs.

These compounds are also provided as pharmaceutical compositions that can be administered to an animal, most preferably a human, for treatment of a disease having either bacterial, fungal or viral etiology, most preferably a human, in an immunologically compromised or debilitated state of health.

In preferred embodiments, the compounds of the invention are those having the structures given by Formulae (I), (II) and (III), with preferred substituents as disclosed herein.

The invention also provides methods for preparing these therapeutic compounds and pharmaceutical compositions thereof, and methods of using said compounds therapeutically. Kits and packaged embodiments of these compounds and pharmaceutical compositions of the invention are also contemplated.

The invention also relates to methods of treating various medical conditions, using the compounds disclosed herein.

DETAILED DESCRIPTION OF THE INVENTION

Definitions and Abbreviations

The abbreviations used herein generally have their conventional meaning within the chemical and biological arts.

"Compound of the invention" and "exemplary compounds of use in methods of the invention," are used interchangeably and refer to the compounds discussed herein, and pharmaceutically acceptable salts and prodrugs of these compounds.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "poly" as used herein means at least 2. For example, a polyvalent metal ion is a metal ion having a valency of at least 2.

"Moiety" refers to the radical of a molecule that is attached to another moiety.

The symbol ⌇⌇⌇, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —OC(O)R', —C(O) R', —CO$_2$R', —CONR'R", —OC(O)NR'R", —NR"C(O)R', —NR'—C(O)NR"R'", —NR"C(O)$_2$R', —NR—C (NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

"Ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. The ring optionally included a heteroatom. Thus, the term "5- to 7-membered ring" includes, for example pyridinyl and piperidinyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The term "pharmaceutically acceptable salts" is meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science* 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al., *J of Controlled Release*, 1:161-162 (1984). The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The term "microbial infection" refers to any infection of a host tissue by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

MIC, or minimum inhibitory concentration, is the point where compound stops more than 90% of cell growth relative to an untreated control.

"Inhibiting" and "blocking," are used interchangeably herein to refer to the partial or full blockade of an editing domain of a tRNA synthetase.

I. Introduction

The present invention provides novel boron compounds and methods for the preparation of these molecules. The invention further provides boron compounds as analogs comprising a functional moiety, such as a drug moiety and methods of use for said analogs.

II. The Compounds

In a first aspect, the invention is a compound described herein. In an exemplary embodiment, the compound has a structure which is a member selected from Formulae (I), (II) or (III):

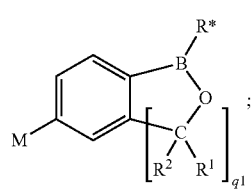
(I)

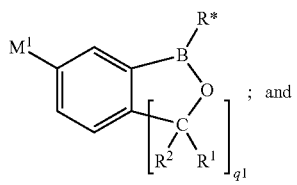
; and (II)

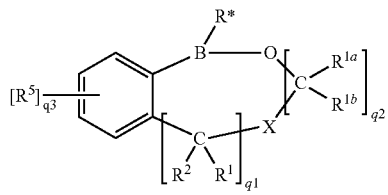
(III)

wherein B is boron. q1 and q2 are integers independently selected from 1 to 3. q3 is an integer selected from 0 to 4. M is a member selected from H, halogen, —OCH$_3$, and —CH$_2$—O—CH$_2$—O—CH$_3$. M$^1$ is a member selected from halogen, —CH$_2$OH, and —OCH$_3$. X is a member selected from O, S, and NR$^{1c}$. R$^{1c}$ is a member selected from H and substituted or unsubstituted alkyl. R$^1$, R$^{1a}$, R$^{1b}$, R$^2$ and R$^5$ are members independently selected from H, OH, NH$_2$, SH, CN, NO$_2$, SO$_2$, OSO$_2$OH, OSO$_2$NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. R* is a member selected from substituted or unsubstituted aryl, substituted or unsubstituted arylalkyl, substituted or unsubstituted heteroaryl, substituted or unsubstituted heteroarylalkyl and substituted or unsubstituted vinyl.

In an exemplary embodiment, there is a proviso that when M is F, R* is not a member selected from:

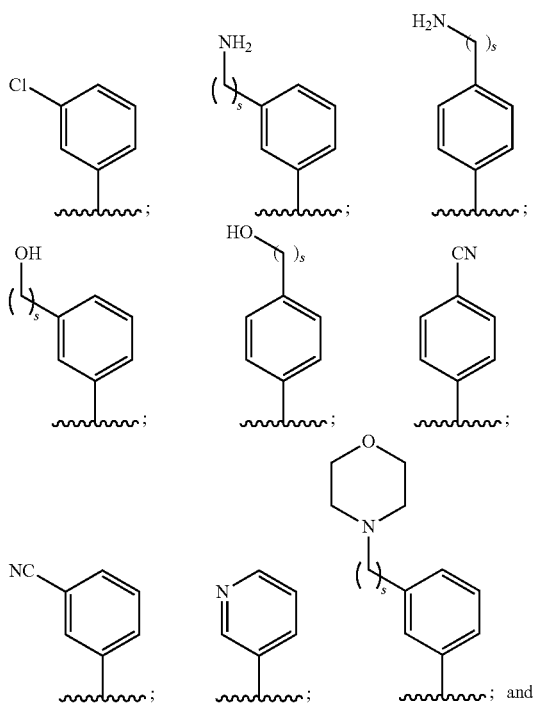

-continued

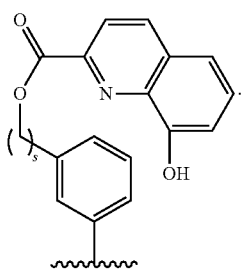

In another exemplary embodiment, there is a proviso that when M is Cl, R* is not a member selected from:

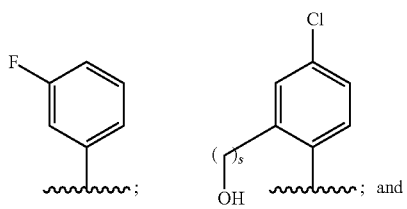

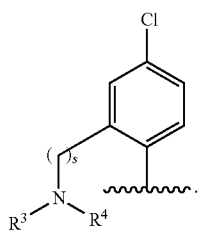

In another exemplary embodiment, there is a proviso that when M is H, R* is not a member selected from:

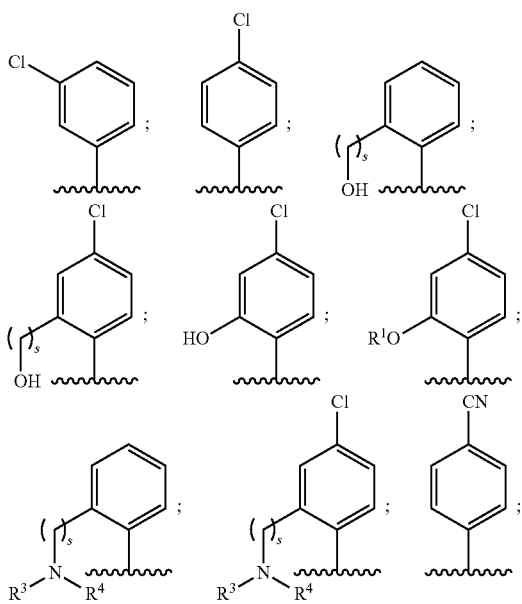

-continued

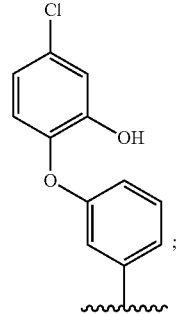

in which the index s is an integer selected from 1 and 2. $R^3$ and $R^4$ are members independently selected from methyl and ethyl.

In another exemplary embodiment, there is a proviso that when M is $OCH_3$, R* is not a member selected from:

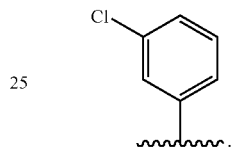

In another exemplary embodiment, there is a proviso that when $M^1$ is F, R* is not a member selected from:

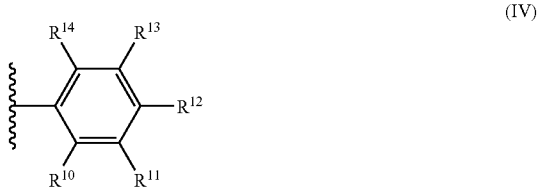

including salts thereof.

In another exemplary embodiment, R* is substituted or unsubstituted aryl. In another exemplary embodiment, aryl has the structure:

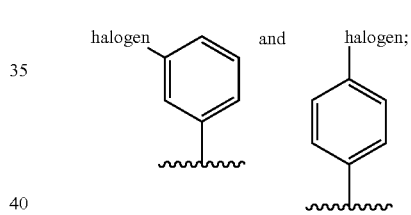

(IV)

in which $R^{10}$, $R^{11}$, $R^{12}$, $R^{13}$ and $R^{14}$ are members independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_3H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$. The index t is a member selected from 1, 2 and 3. The index u is a member selected from 0, 1 and 2. $R^{22}$ and $R^{23}$ are members independently selected from H, substituted or unsubstituted alkyl, and substituted or unsubstituted alkanoyl.

In another exemplary embodiment, R* is substituted or unsubstituted arylalkyl. In another exemplary embodiment, arylalkyl has the structure:

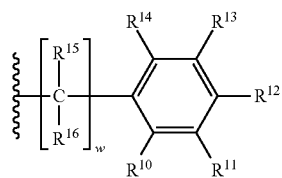

(V)

wherein $R^{10}$, $R^{11}$, $R^{12}$, $R^{13}$ and $R^{14}$ are members independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_3H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$. The index t is an integer selected from 1, 2 and 3. The index u is a member selected from 0, 1 and 2. $R^{22}$ and $R^{23}$ are members independently selected from H, substituted or unsubstituted alkyl, and substituted or unsubstituted alkanoyl. $R^{15}$ and $R^{16}$ are members independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_3H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$. The index w is a member selected from 1 to 6.

In another exemplary embodiment, R* is substituted or unsubstituted heteroaryl. In another exemplary embodiment, heteroaryl has a structure which is a member selected from:

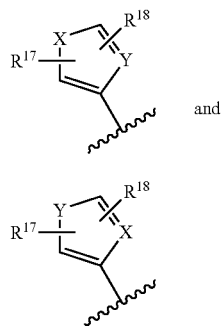

(VIa)

and (VIb)

X is a member selected from CH=CH, N=CH, $NR^{19}$, O and S. $R^{19}$ is a member selected from H, substituted or unsubstituted alkyl, substituted or unsubstituted aryl and substituted or unsubstituted arylalkyl. Y is a member selected from CH and N. $R^{17}$ and $R^{18}$ are members independently selected from H, substituted or unsubstituted alkyl, substituted or unsubstituted aryl, substituted or unsubstituted arylalkyl, $(CH_2)_vOH$, $(CH_2)_wNR^{24}R^{25}$, $CO_2H$, $CO_2$-alkyl, $CONH_2$, S-alkyl, S-aryl, SO-alkyl, SO-aryl, $SO_2$-alkyl, $SO_2$-aryl, $SO_3H$, $SCF_3$, CN, halogen, $CF_3$ and $NO_2$. $R^{24}$ and $R^{25}$ are members independently selected from hydrogen, substituted or unsubstituted alkyl and substituted or unsubstituted alkanoyl. The index v is a member selected from 1, 2 and 3. The index w is a member selected from 0, 1, 2 and 3.

In another exemplary embodiment, R* is substituted or unsubstituted vinyl. In another exemplary embodiment, vinyl has a structure according to the following formula:

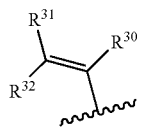

(VII)

wherein $R^{31}$, $R^{32}$ and $R^{33}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted arylalkyl, $(CH_2)_vOH$, $(CH_2-NR^{24}R^{25}$, $CO_2H$, $CO_2$-alkyl, $CONH_2$, S-alkyl, S-aryl, SO-alkyl, SO-aryl, $SO_2$-alkyl, $SO_2$-aryl, $SO_3H$, $SCF_3$, CN, halogen, $CF_3$ and $NO_2$. $R^{24}$ and $R^{25}$ are members independently selected from hydrogen, substituted or unsubstituted alkyl and substituted or unsubstituted alkanoyl. The index v is a member selected from 1, 2 and 3. The index w is a member selected from 0, 1, 2 and 3.

In an exemplary embodiment, R* is a member selected from

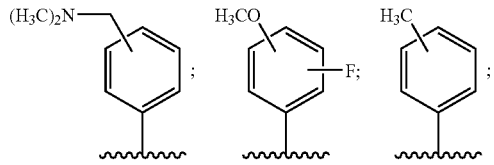

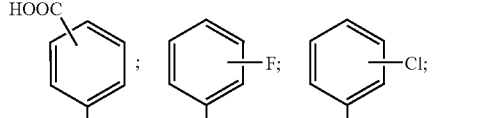

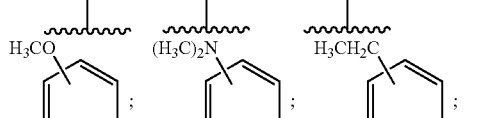

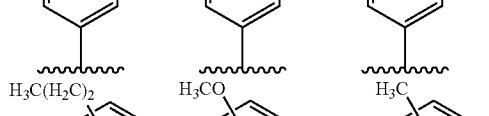

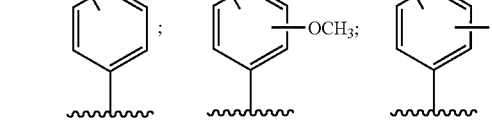

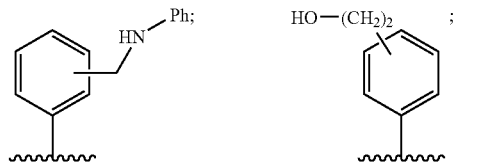

-continued
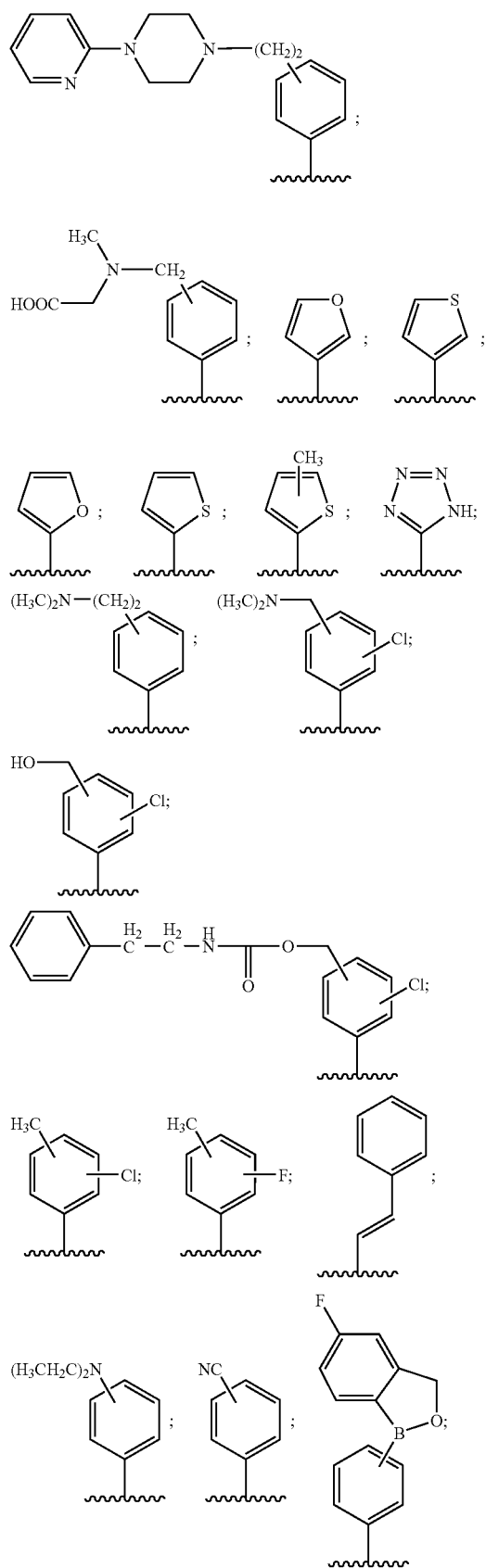
-continued
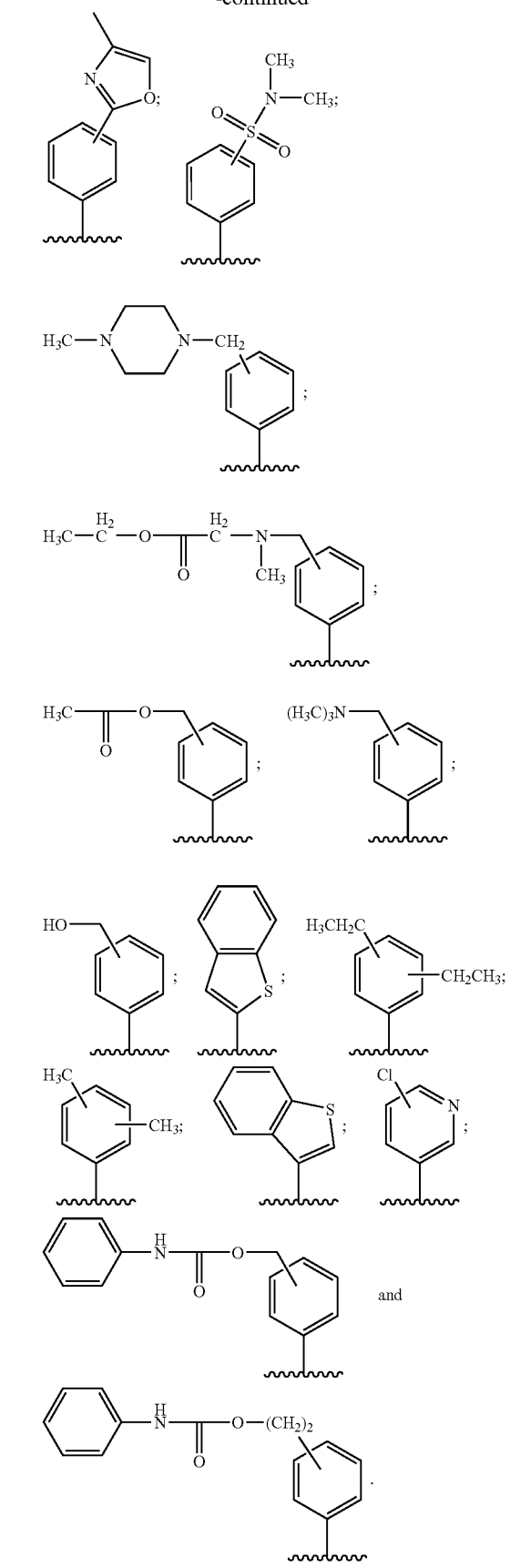
and

In an exemplary embodiment, R* is a member selected from:
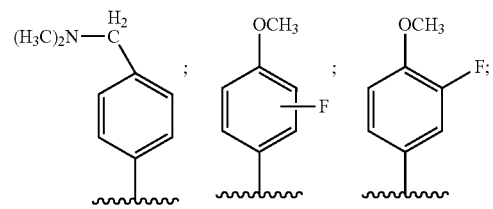
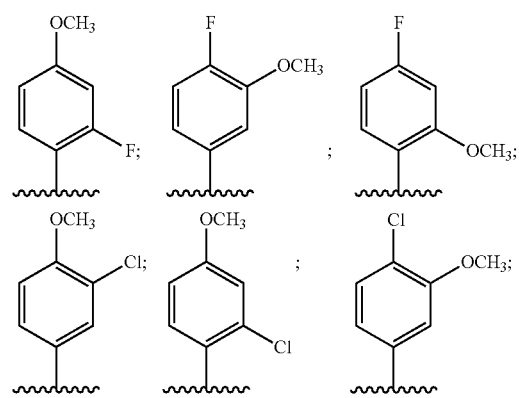
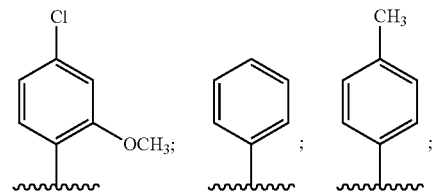
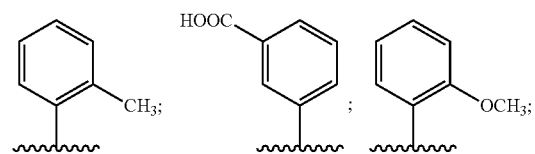
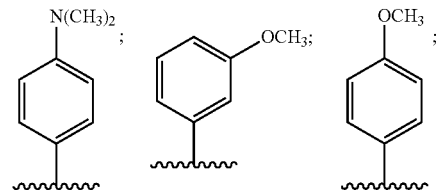
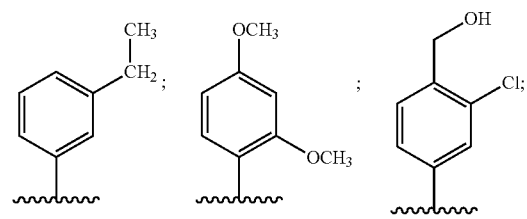
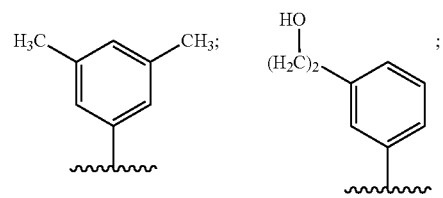
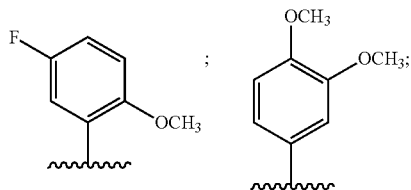
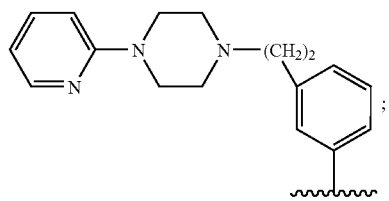
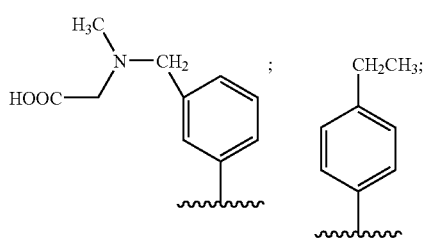
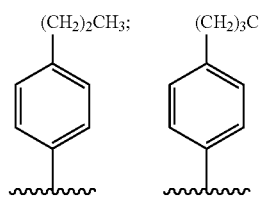
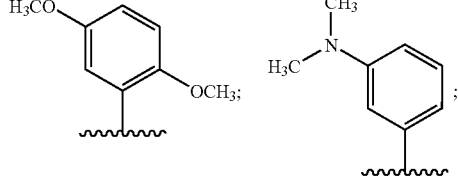
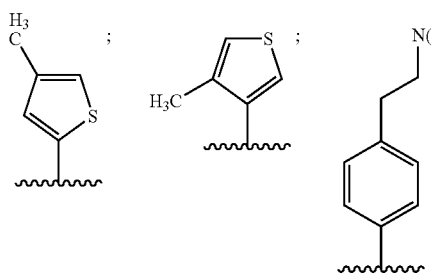
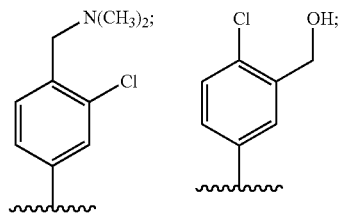
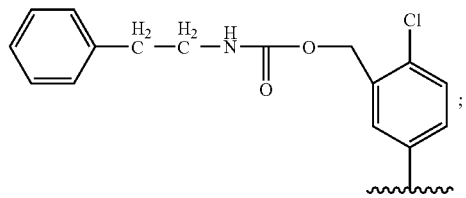

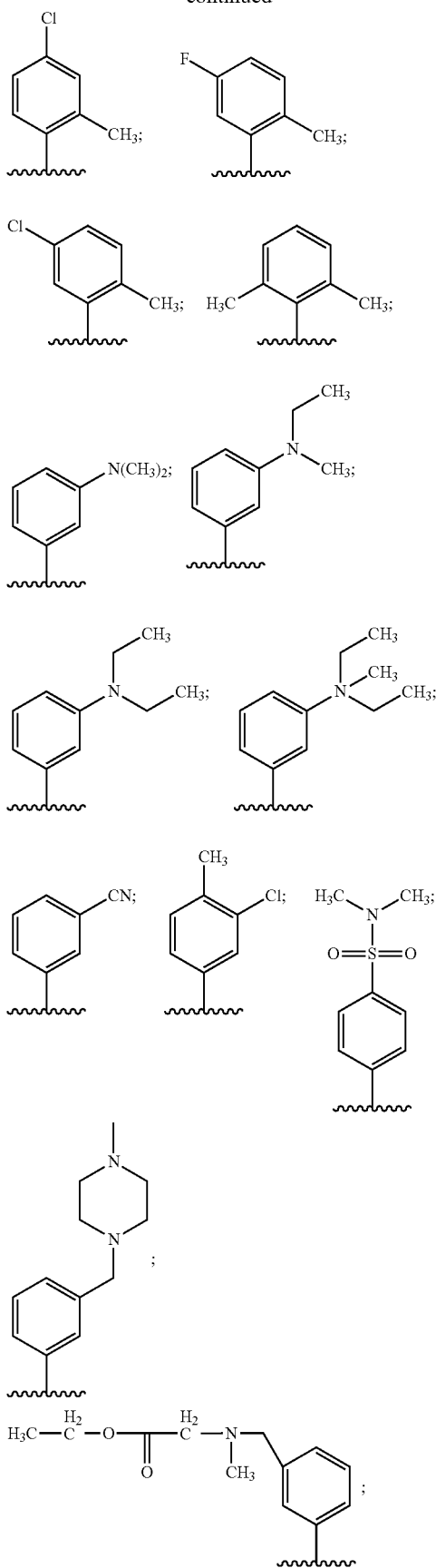
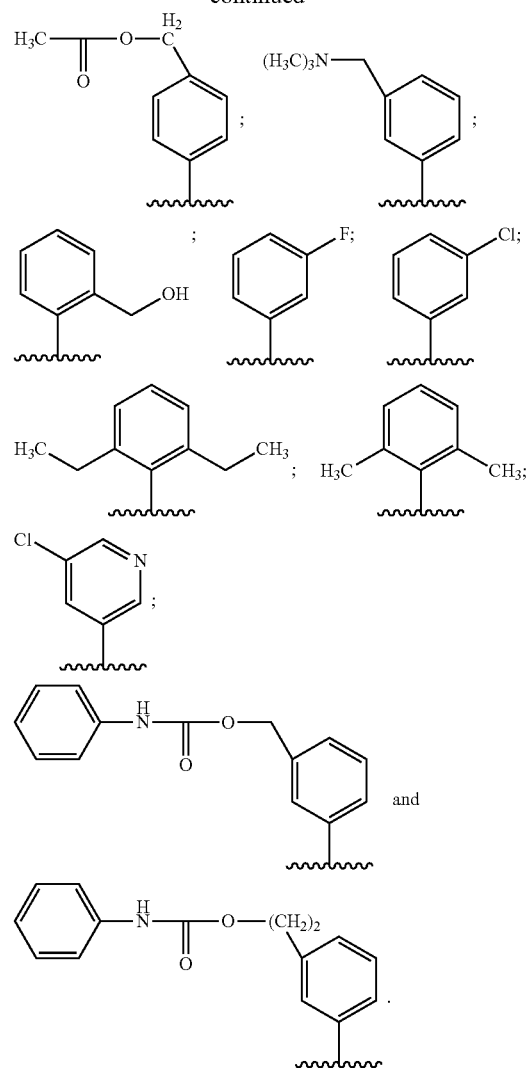
In an exemplary embodiment, M is H, Cl or F in Formula (I), or $M^1$ is H, Cl or F in Formula (II), and R* in either Formula is a member selected from:
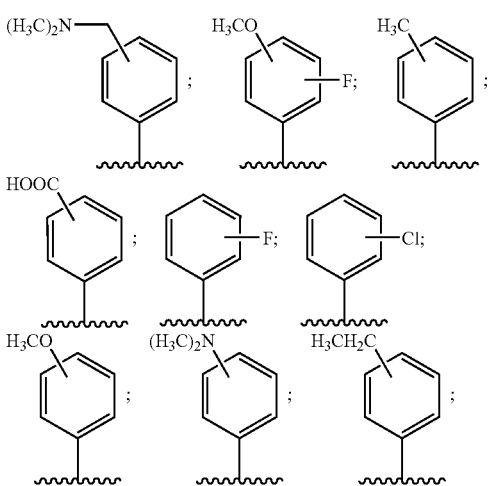

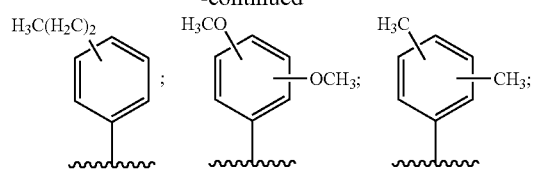
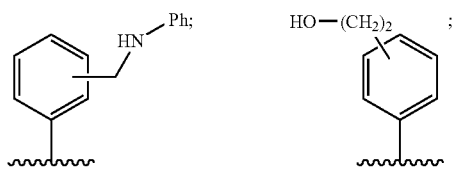
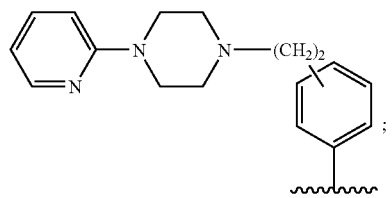
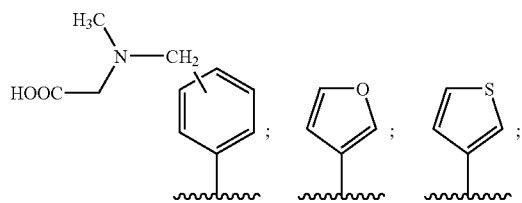
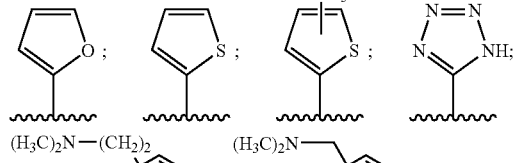
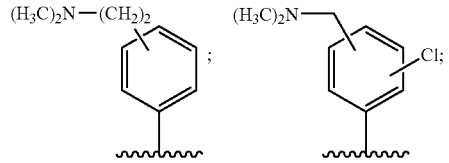
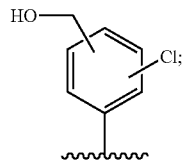
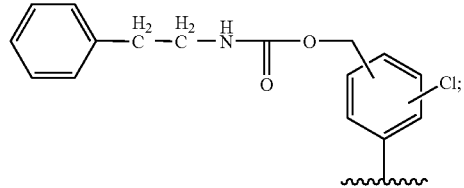
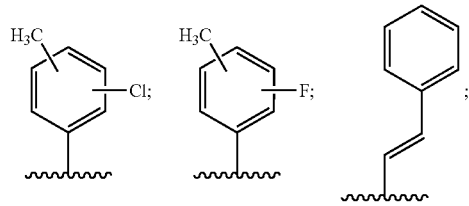
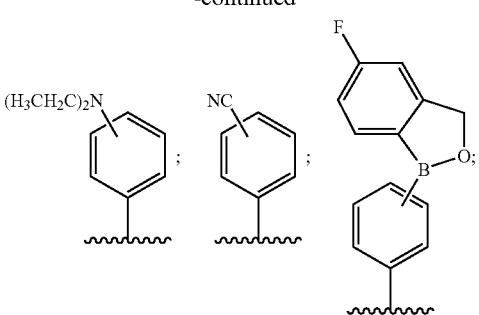
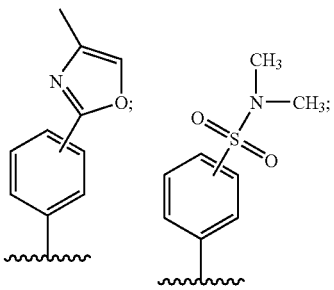
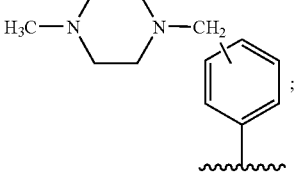
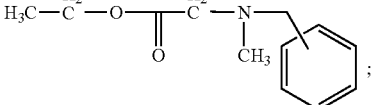
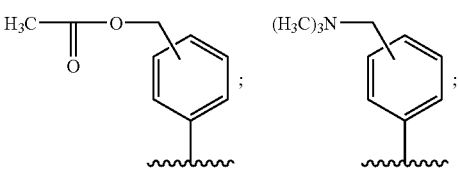
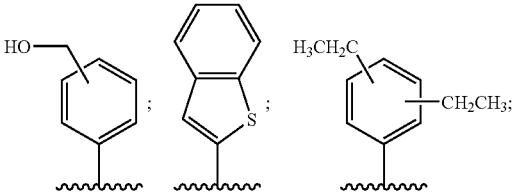
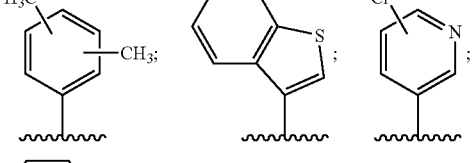
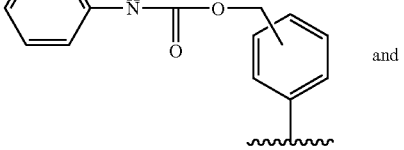
and

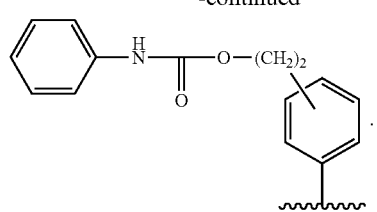
In an exemplary embodiment, M is F in Formula (I), then R* is a member selected from
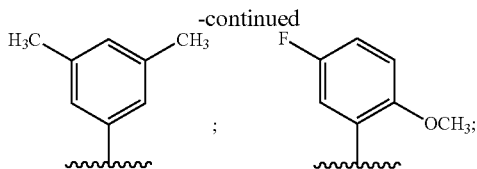
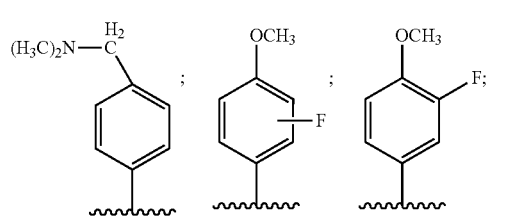
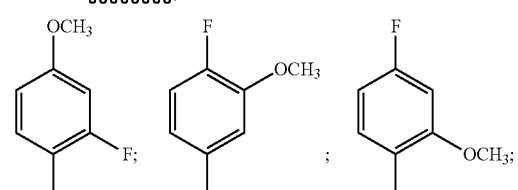
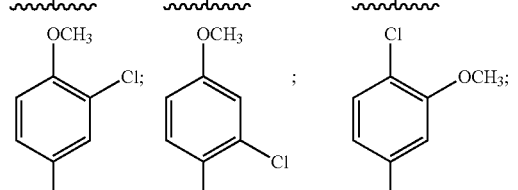
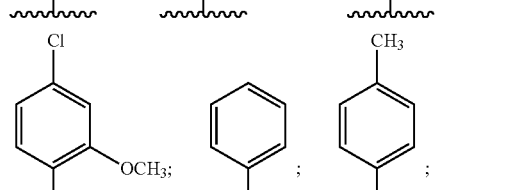
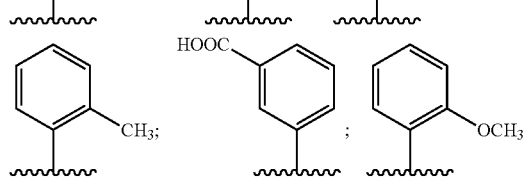
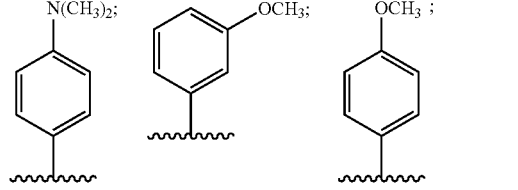
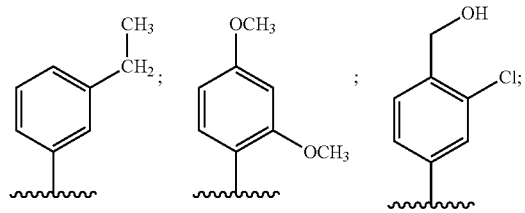
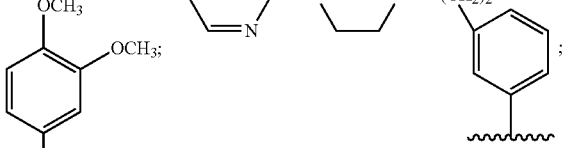
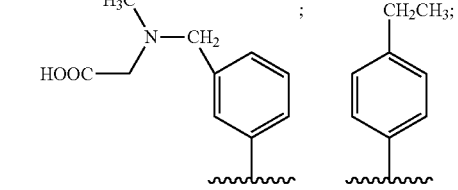
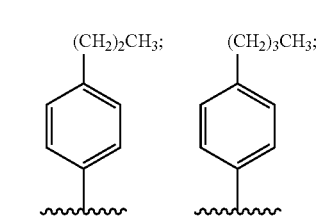
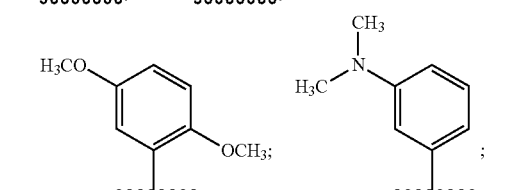
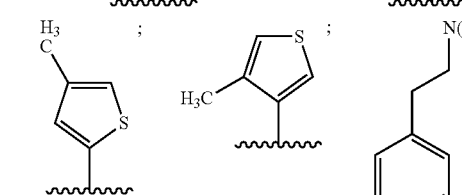
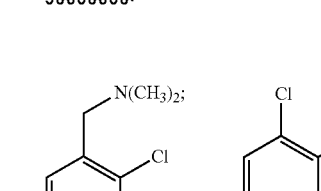
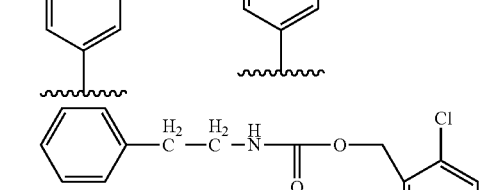

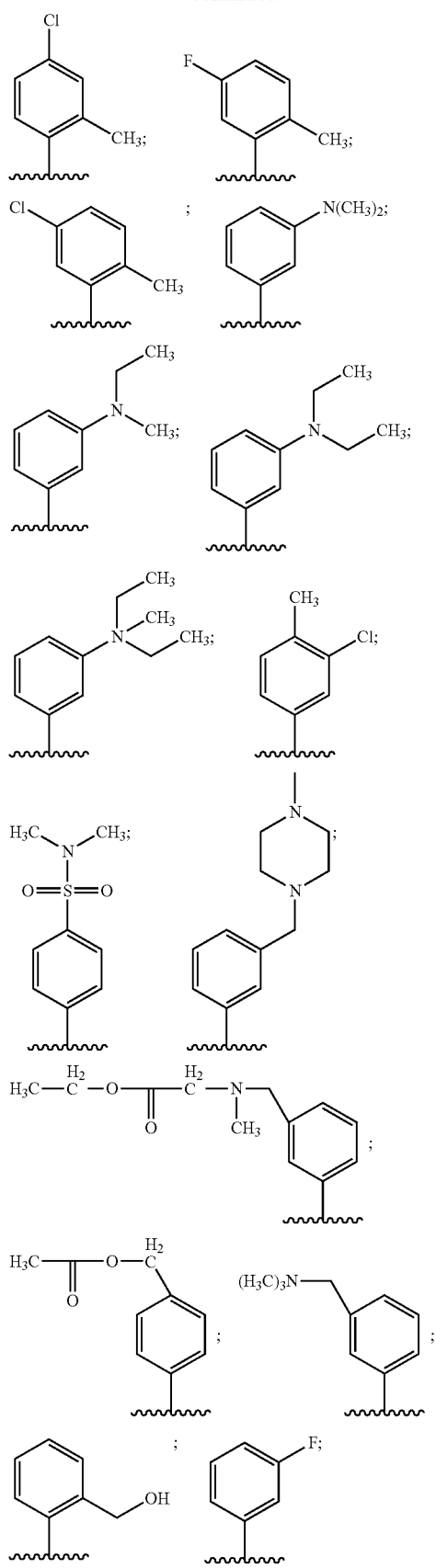
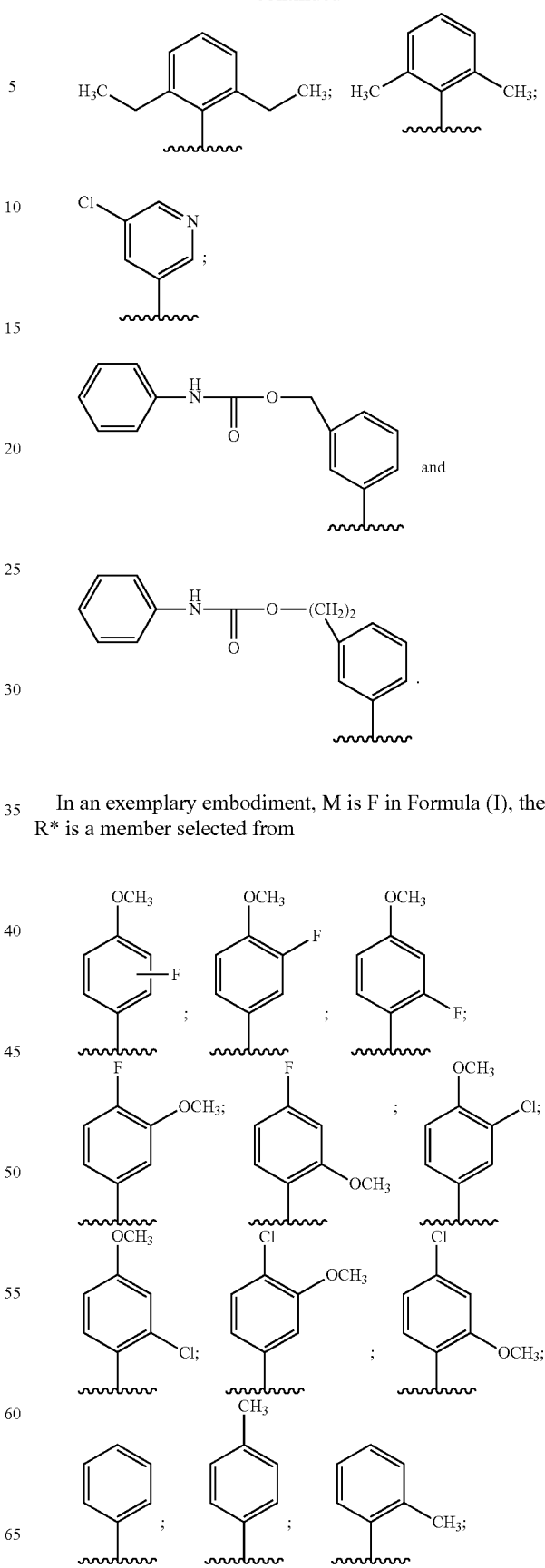
In an exemplary embodiment, M is F in Formula (I), then R* is a member selected from -continued
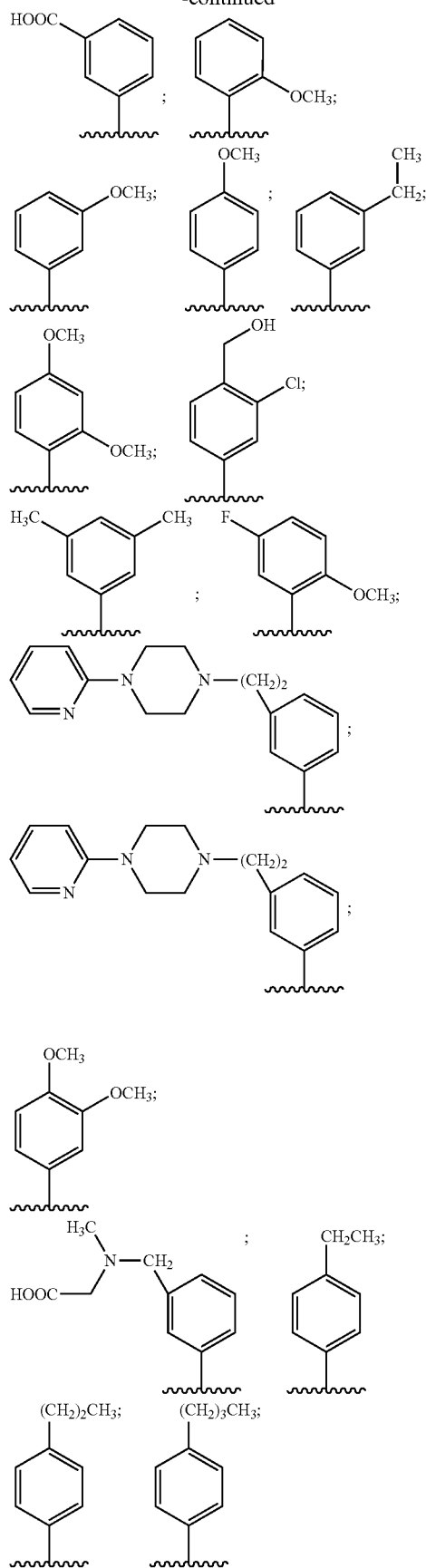
-continued
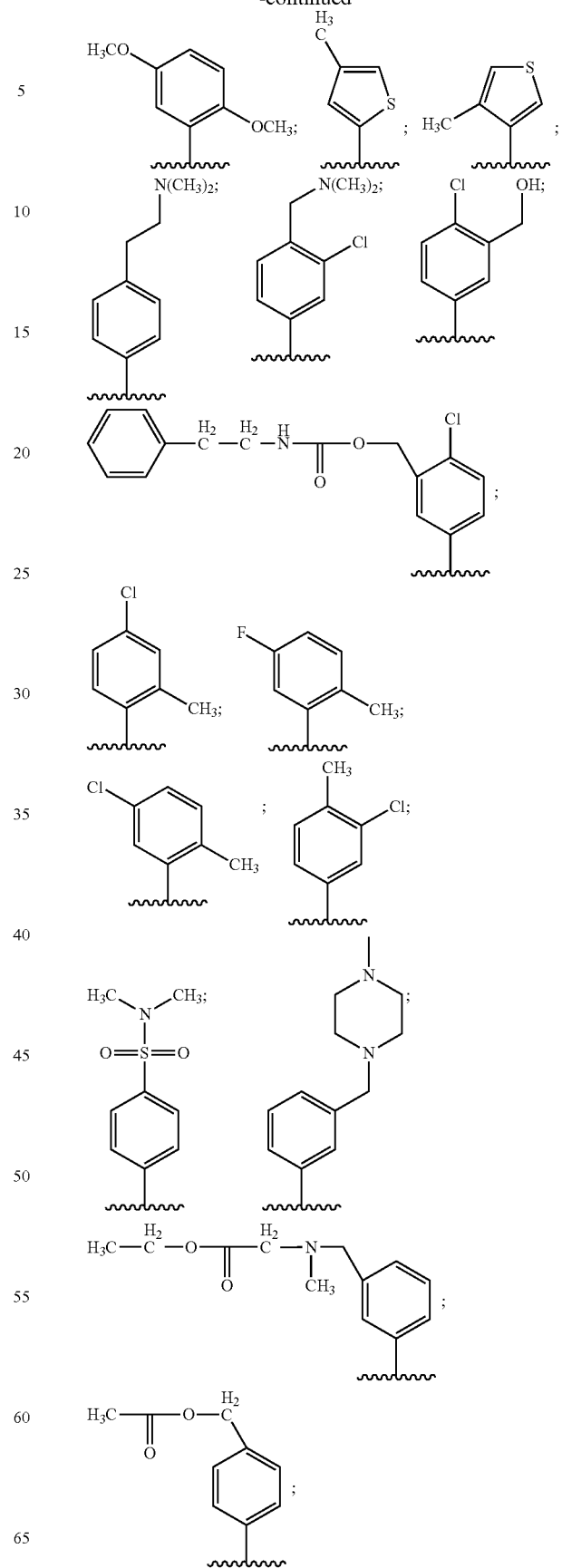

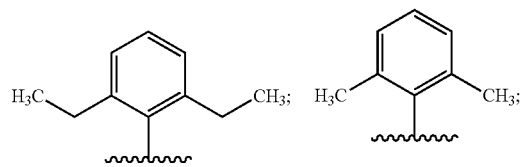
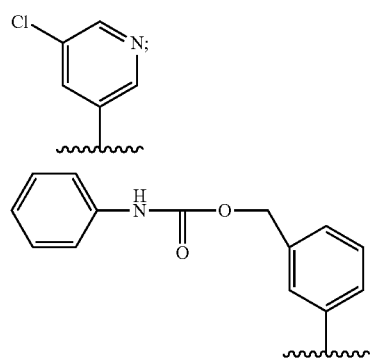
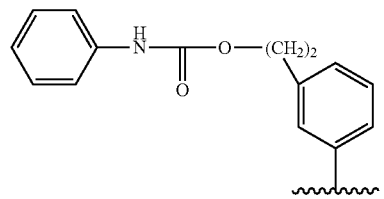
In an exemplary embodiment, M is F in Formula (I), then R* is a member selected from
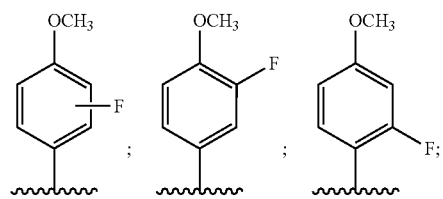
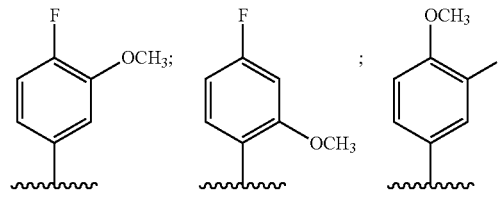
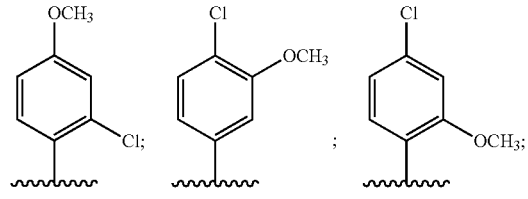
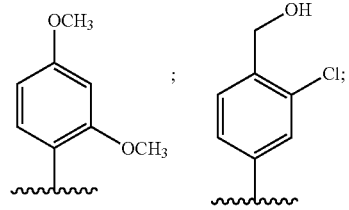
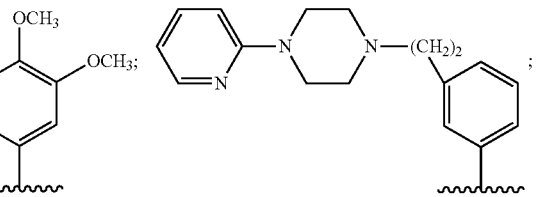
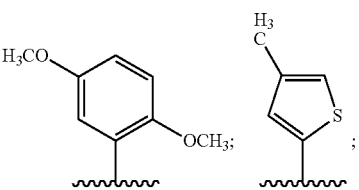
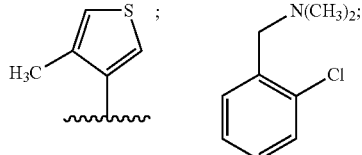
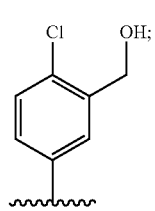
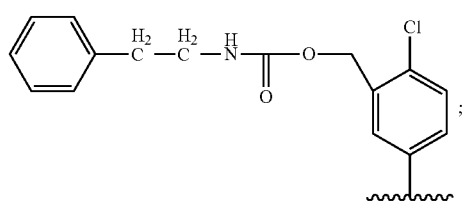
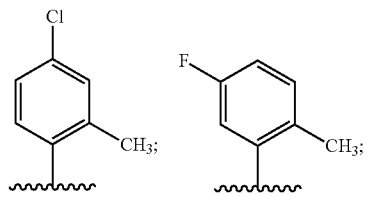
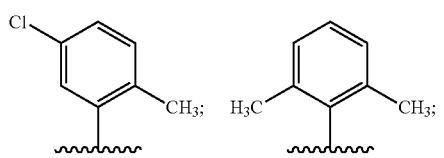

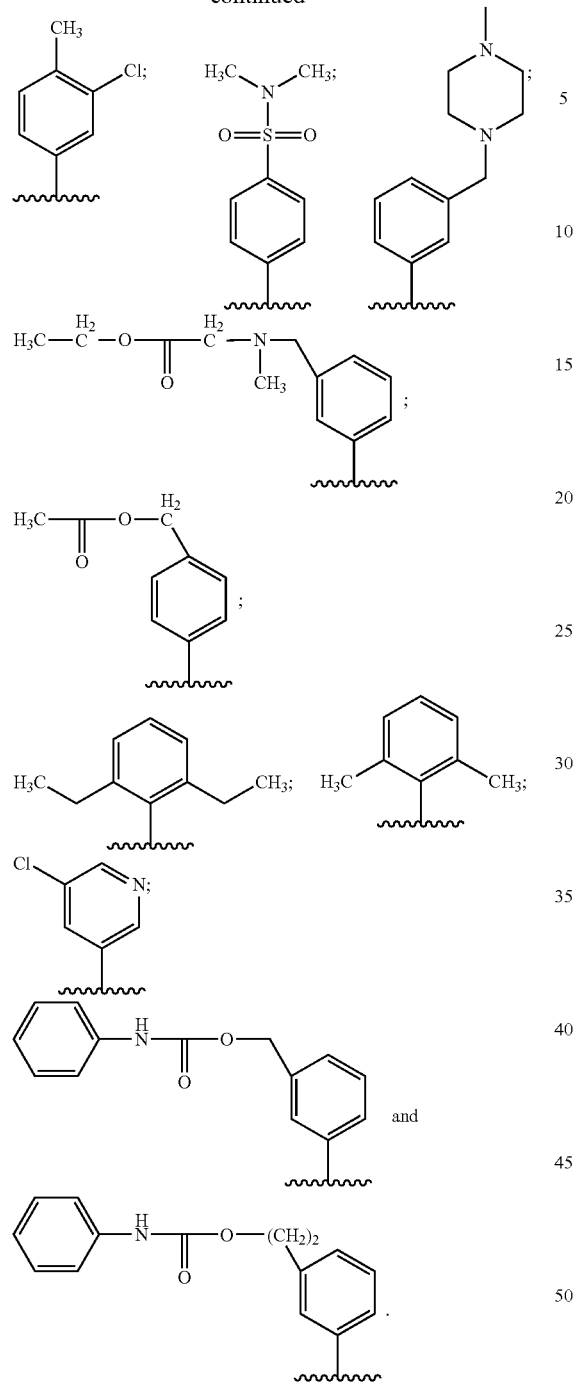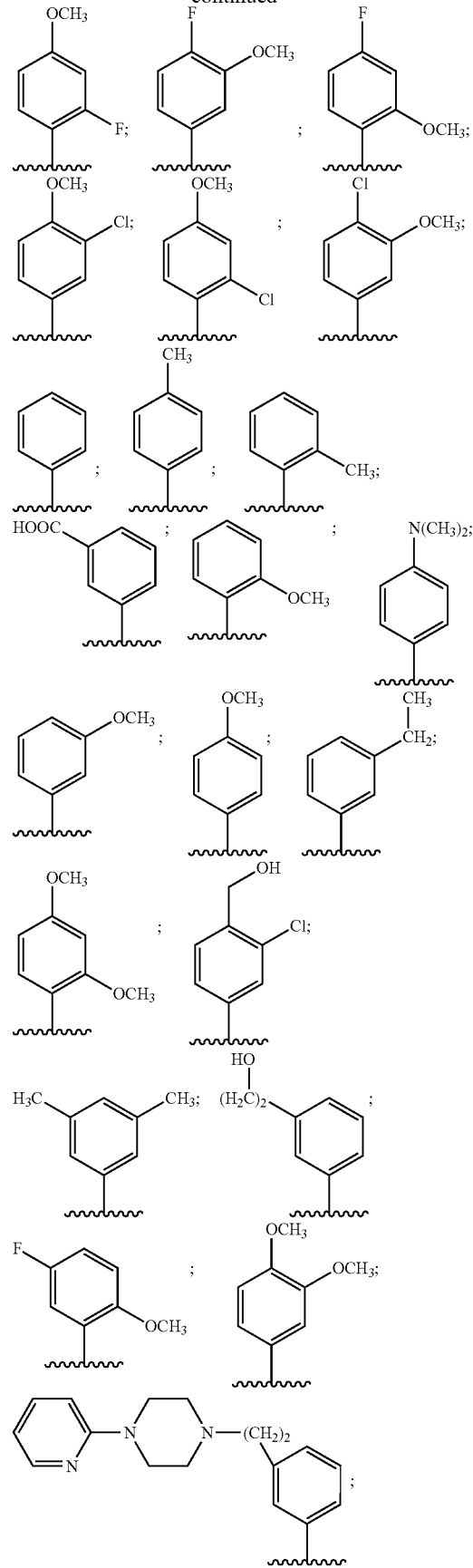
In an exemplary embodiment, M is H in Formula (I), then R* is a member selected from
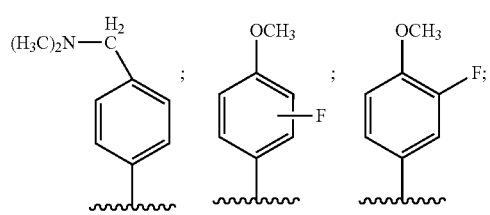

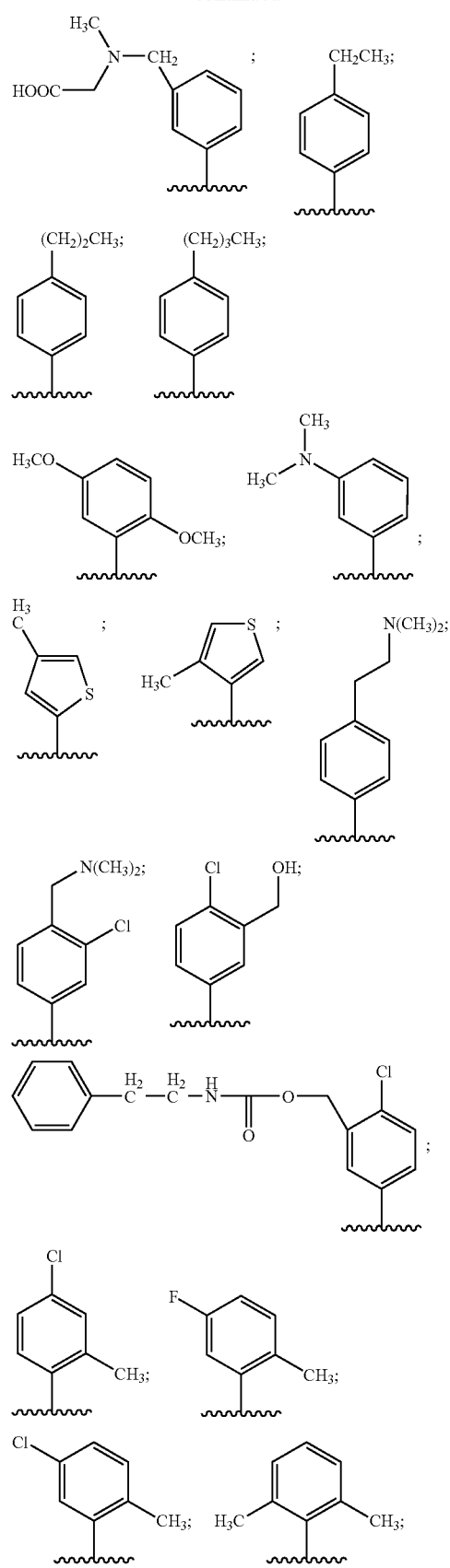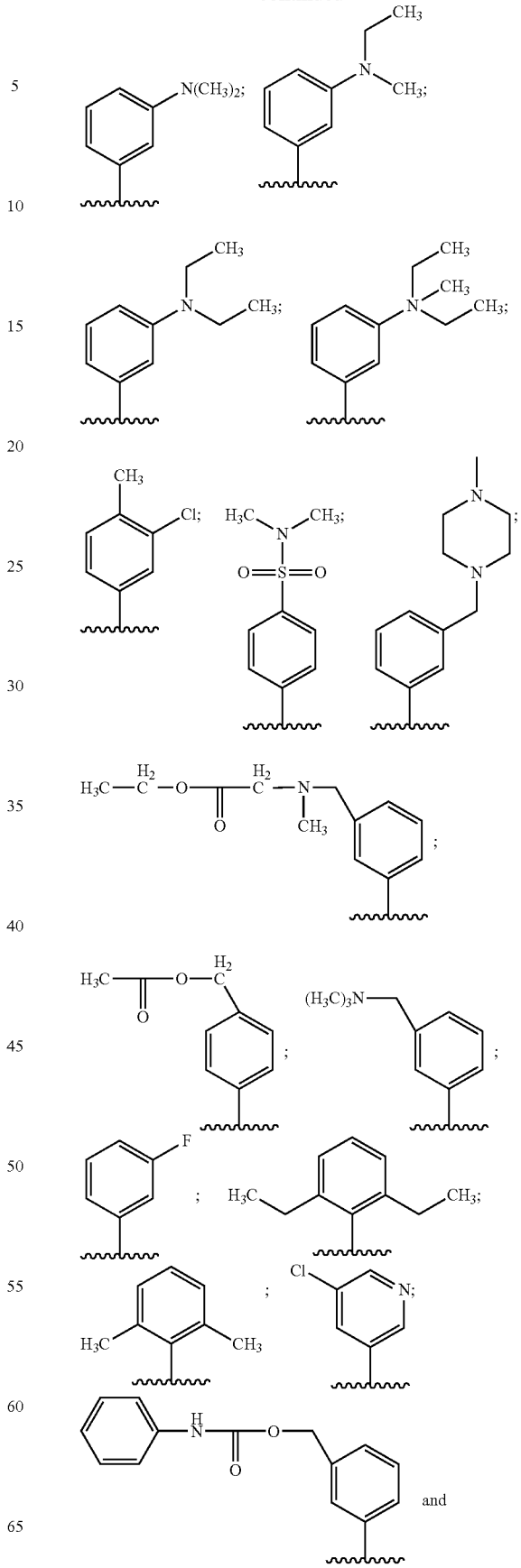

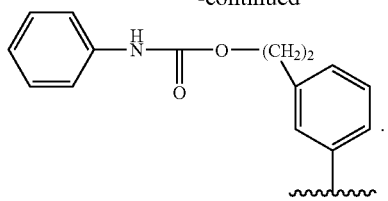
In an exemplary embodiment, M is H in Formula (I), then R* is a member selected from
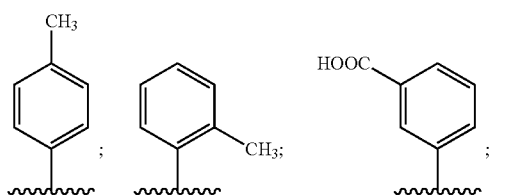
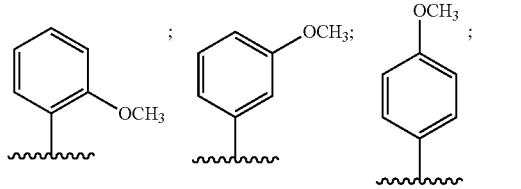
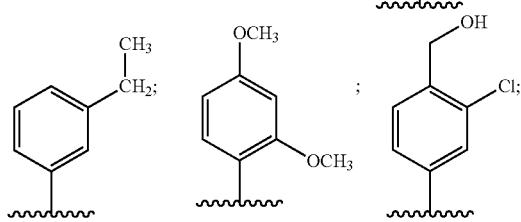
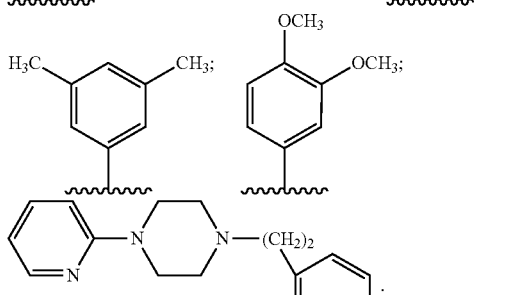
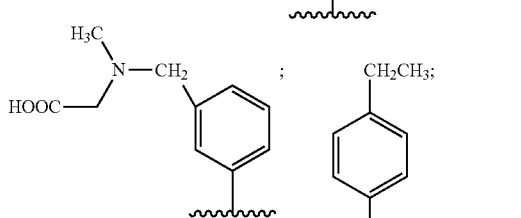
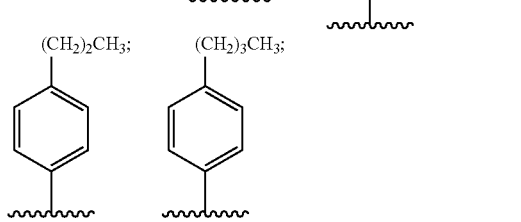
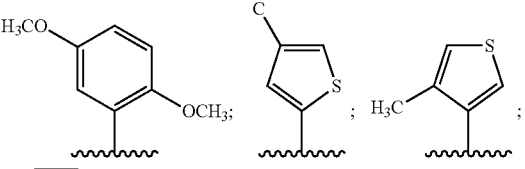
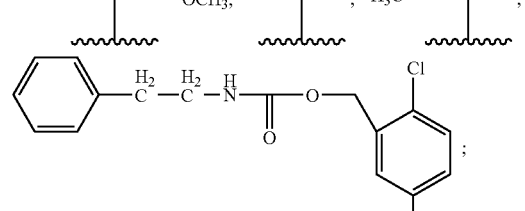
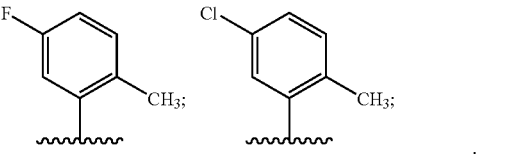
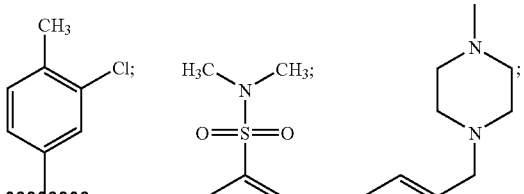
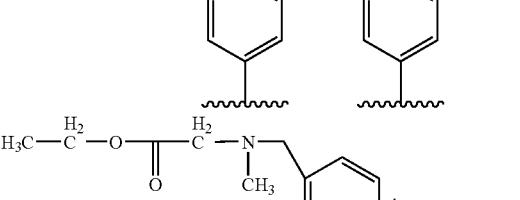
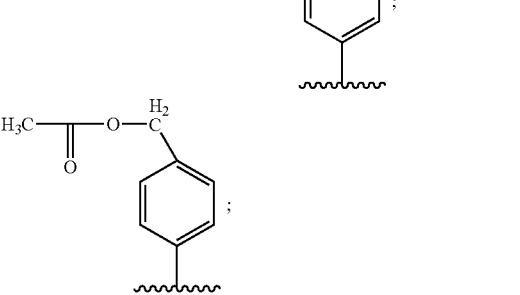
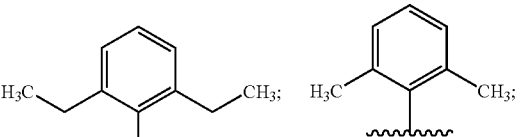
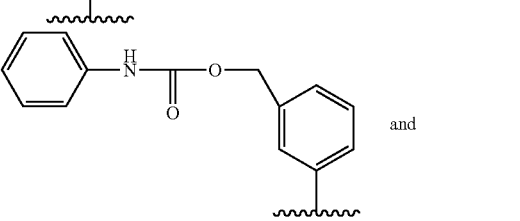 and

37
-continued
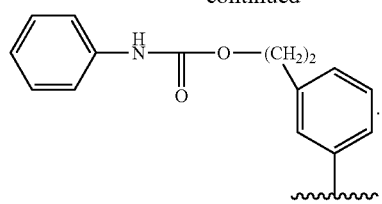
In an exemplary embodiment, M is H in Formula (I), then R* is a member selected from
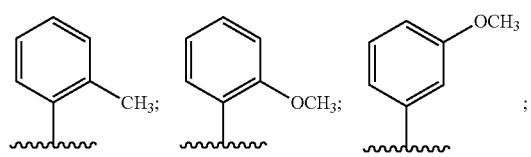
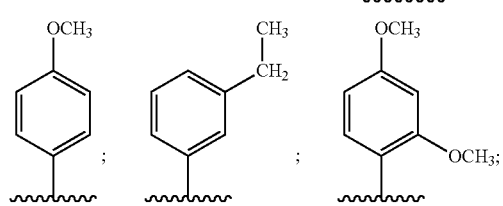
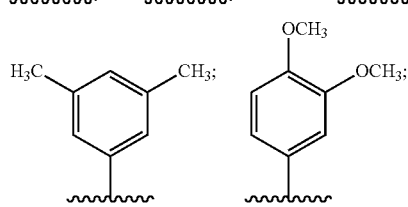
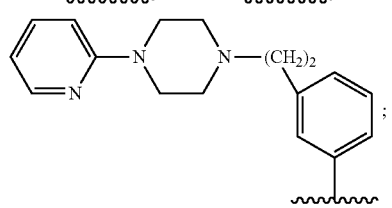
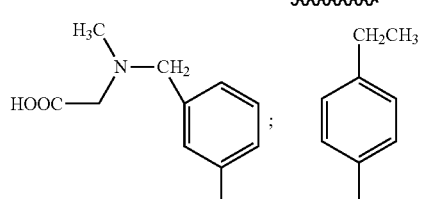
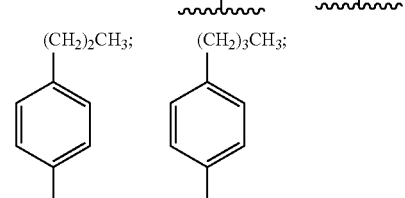
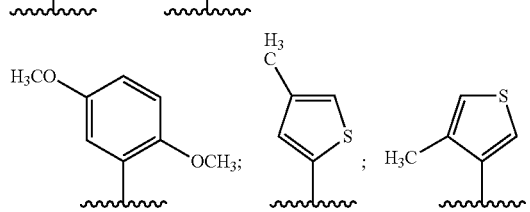
38
-continued
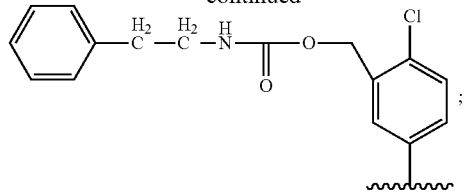
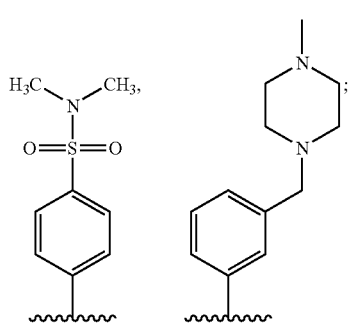
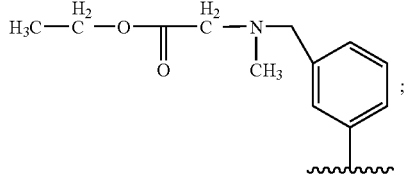
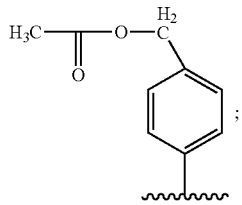
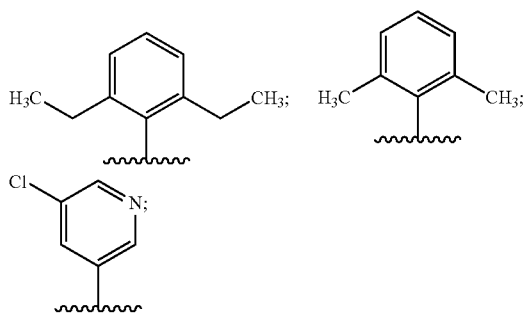
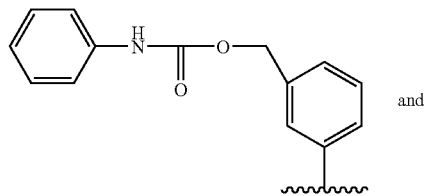
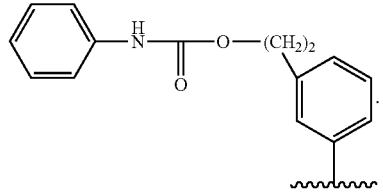 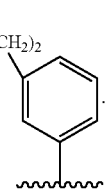

In an exemplary embodiment, M is Cl in Formula (I), then R* is a member selected from
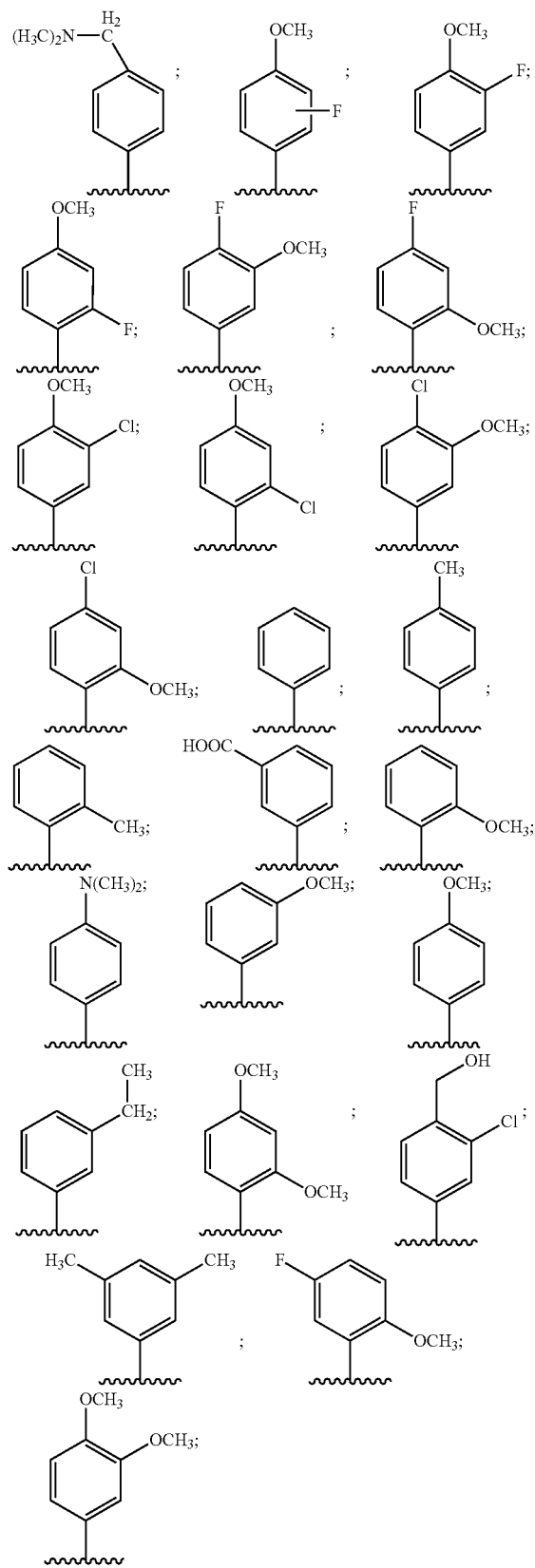
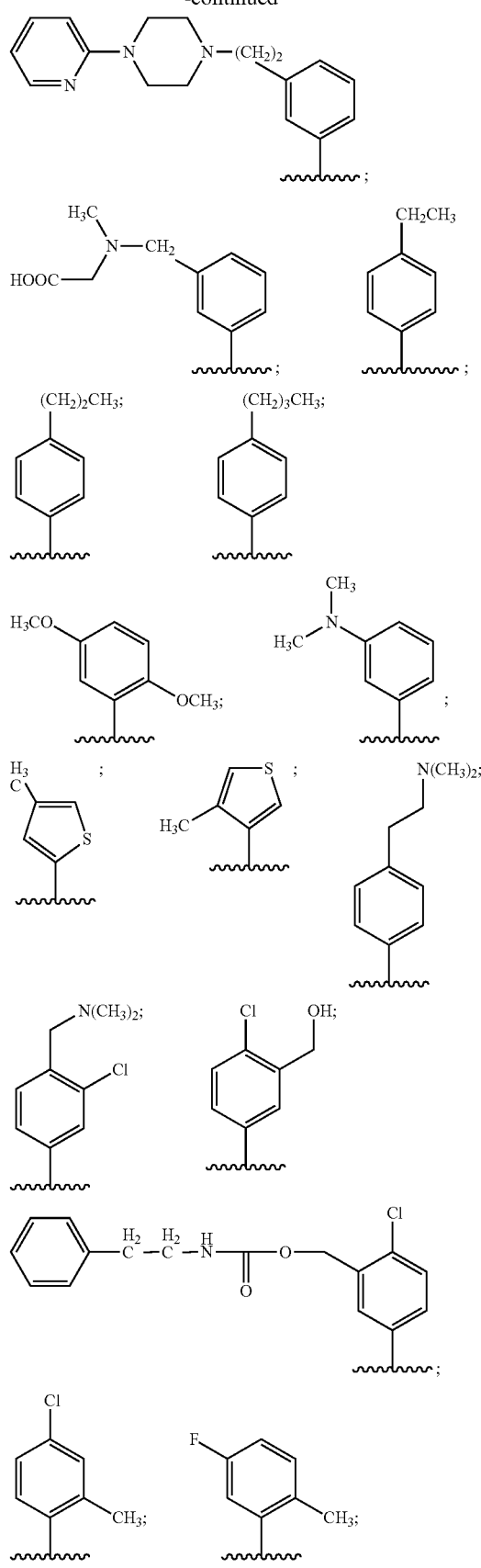

-continued
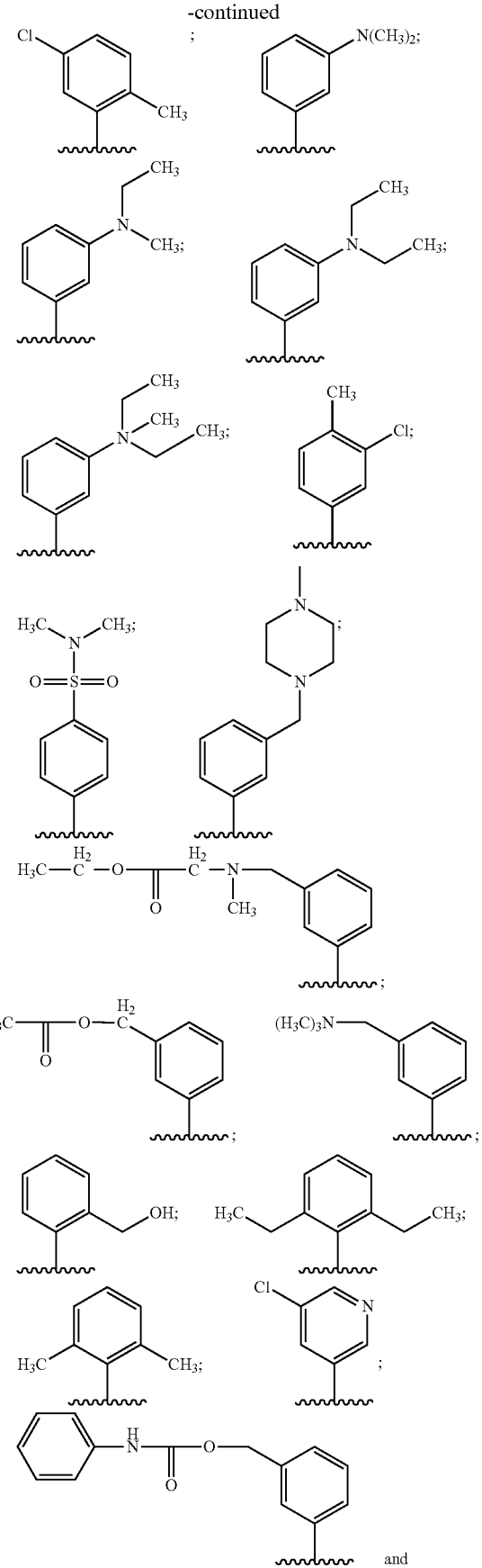
In an exemplary embodiment, M is Cl in Formula (I), then R* is a member selected from
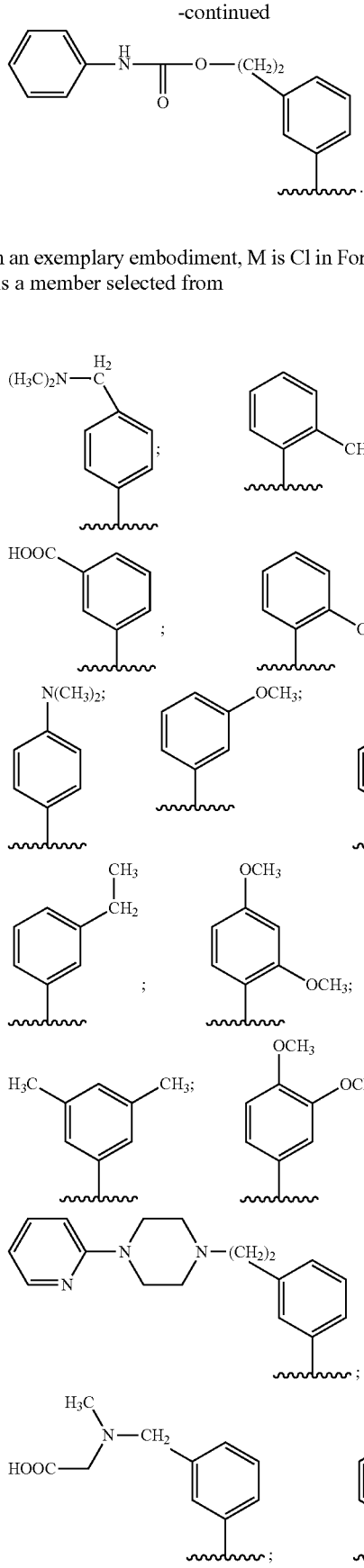

-continued
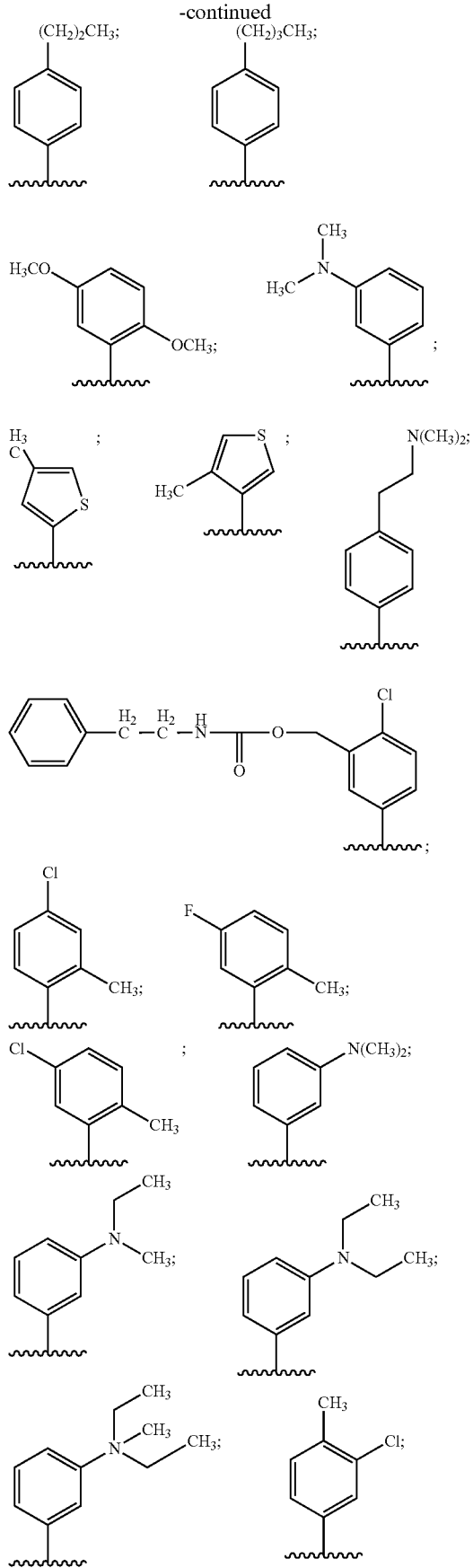
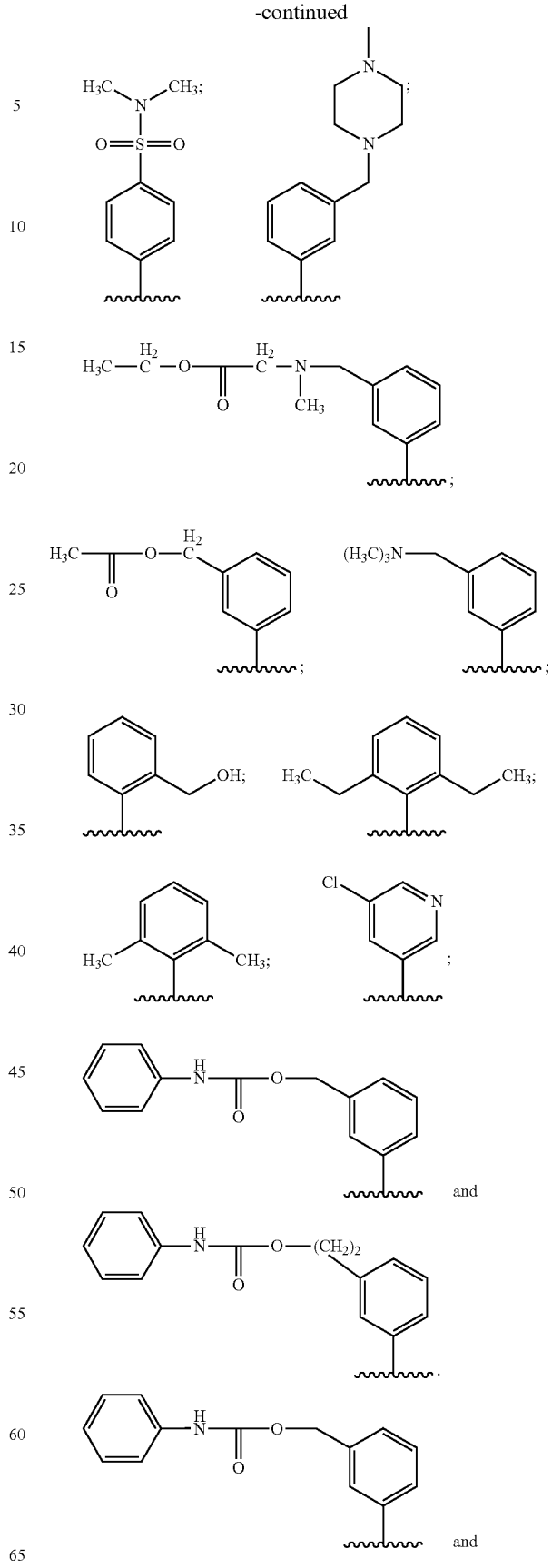

In an exemplary embodiment, $M^1$ is F in Formula (II), then R* is a member selected from
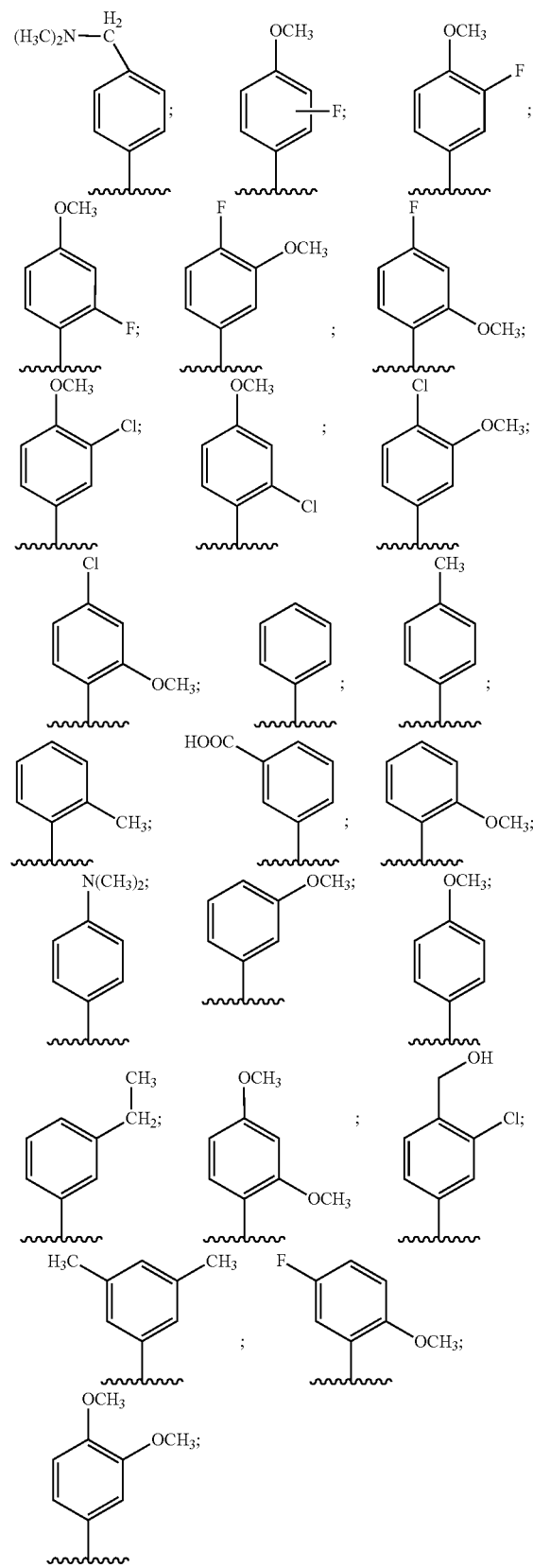
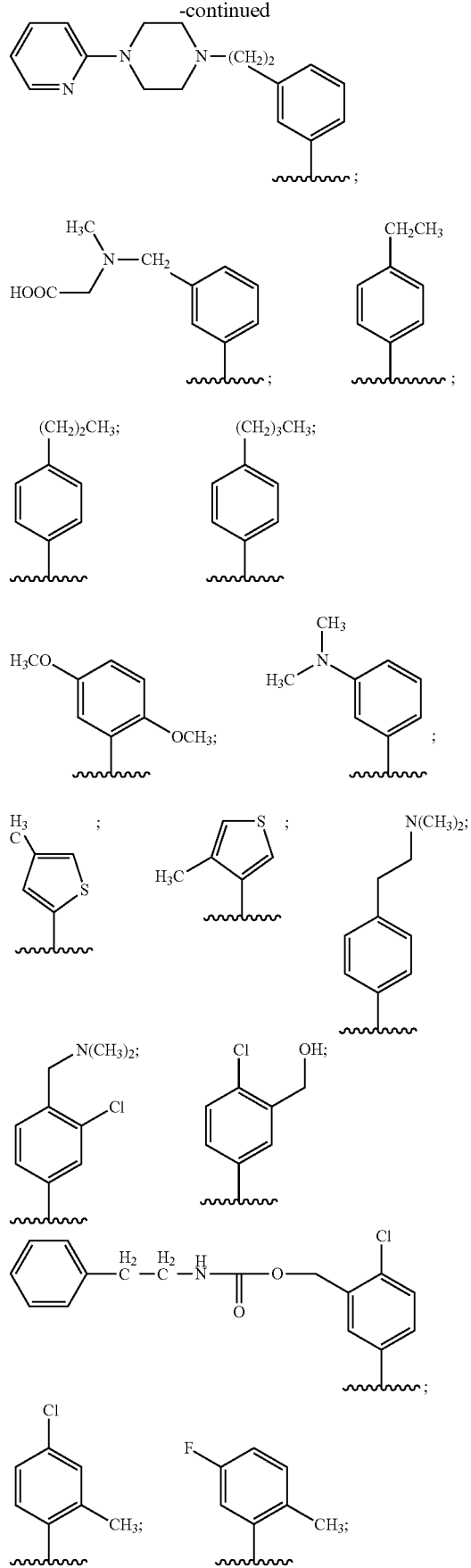

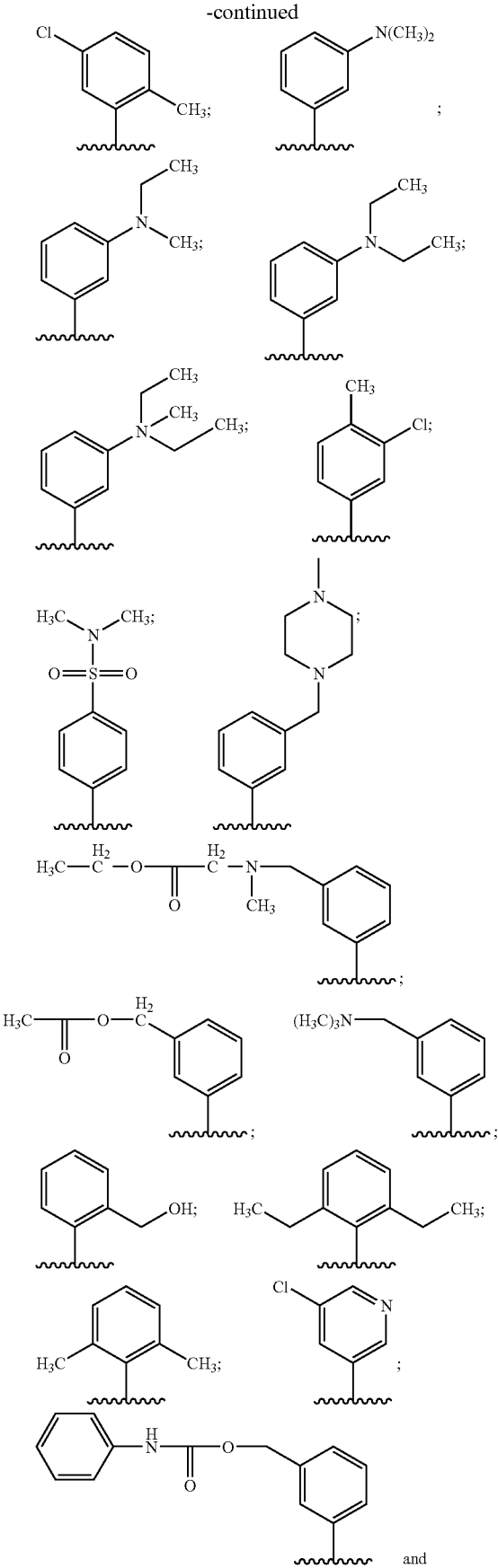
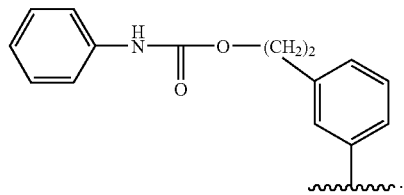
In an exemplary embodiment, $M^1$ is F in Formula (II), then R* is a member selected from
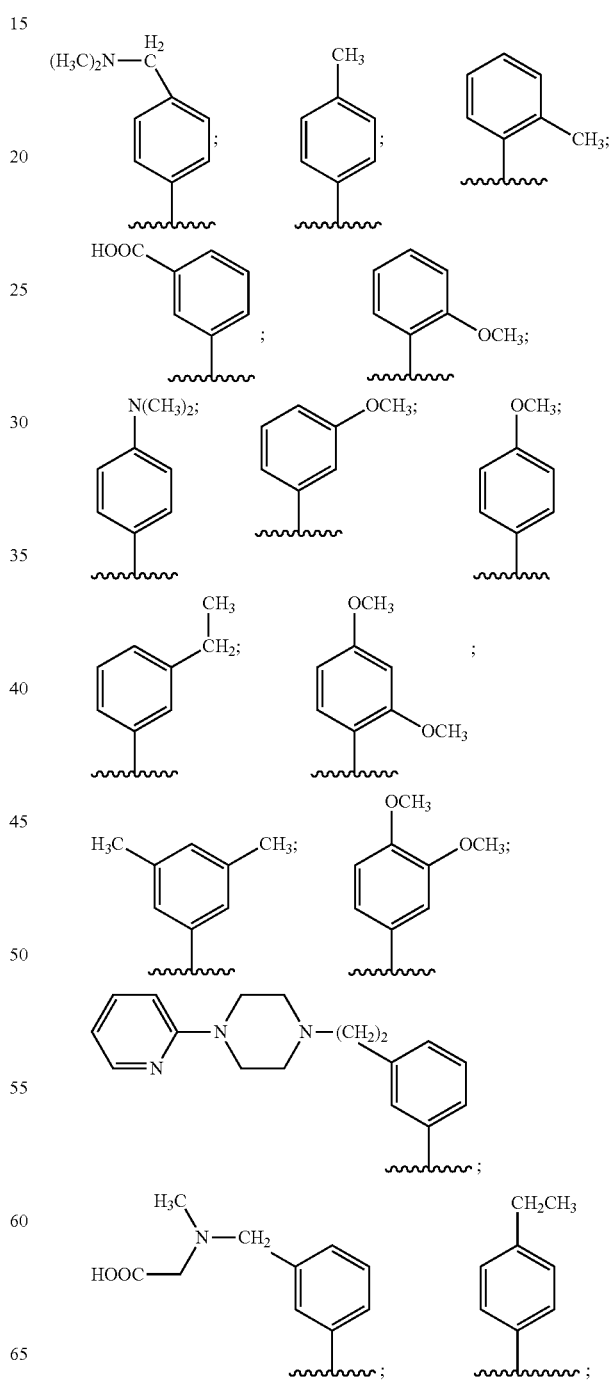

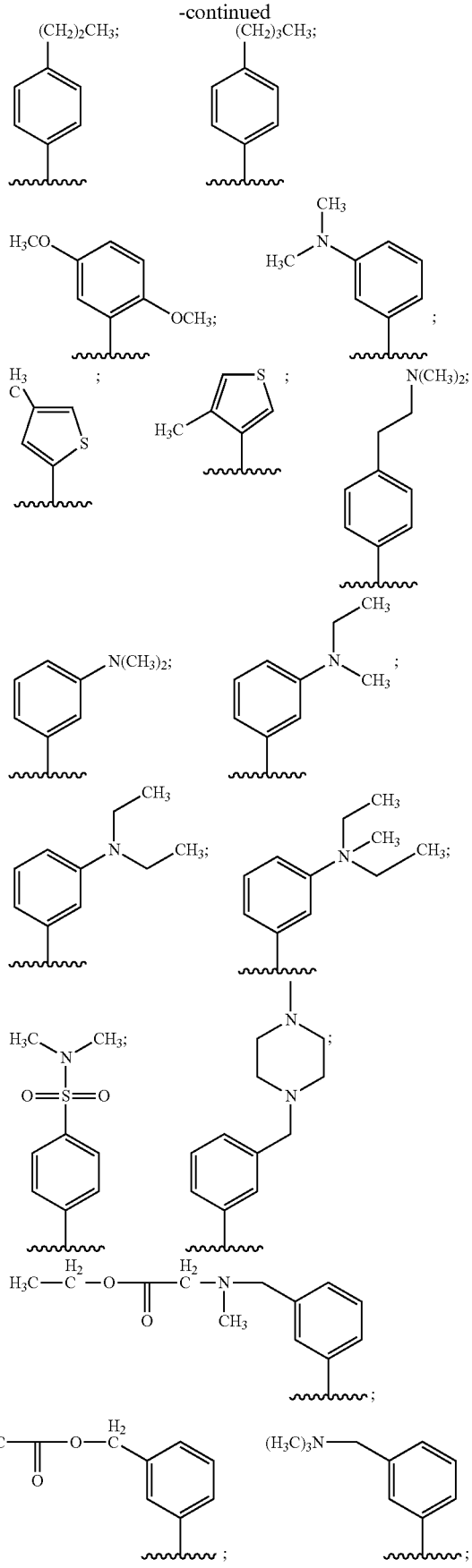
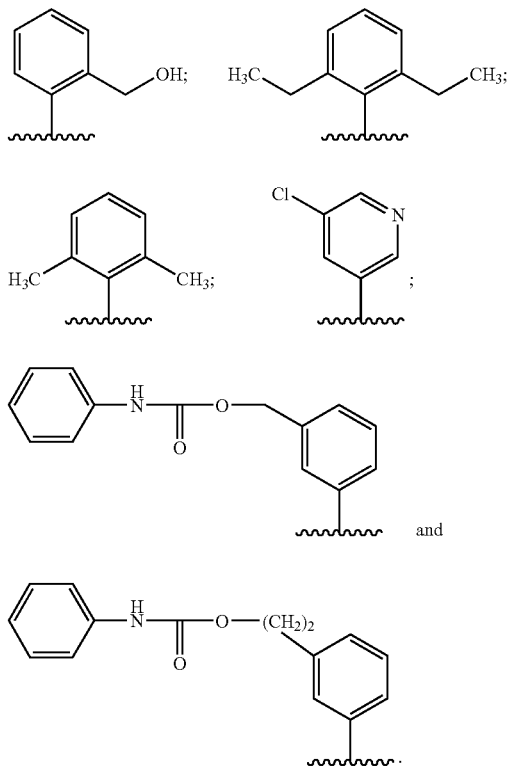

In an exemplary embodiment, $R^1$ and $R^2$ are members independently selected from H, substituted or unsubstituted alkyl, and substituted or unsubstituted aryl. In an exemplary embodiment, $R^1$ is H and $R^2$ is a member selected from H, substituted or unsubstituted alkyl, and substituted or unsubstituted aryl. In an exemplary embodiment, $R^1$ is H and $R^2$ is a member selected from H, unsubstituted alkyl, and unsubstituted phenyl. In an exemplary embodiment, $R^1$ is H and $R^2$ is a member selected from unsubstituted alkyl, and unsubstituted phenyl. In an exemplary embodiment, $R^1$ is H and $R^2$ is a member selected from methyl, ethyl, propyl, isopropyl, butyl, t-butyl, sec-butyl, isobutyl, pentyl, neopentyl, isopentyl, hexyl and isohexyl. In an exemplary embodiment, $R^1$ is H and $R^2$ is a member selected from methyl, ethyl, propyl, isopropyl, butyl and t-butyl. In an exemplary embodiment, $R^1$ is H and $R^2$ is a member selected from methyl, ethyl and propyl. In an exemplary embodiment, $R^1$ is H and $R^2$ is a member selected from H, methyl, and phenyl.

In an exemplary embodiment, the compound is according to Formula (I) and q1 is 1. In an exemplary embodiment, the compound is according to Formula (I) and q1 is 2. In an exemplary embodiment, the compound is according to Formula (II) and q1 is 1. In an exemplary embodiment, the compound is according to Formula (II) and q1 is 2. In an exemplary embodiment, the compound is according to Formula (III) and q1 is 1 and q2 is 1. In an exemplary embodiment, the compound is according to Formula (III) and q1 is 1 and q2 is 2. In an exemplary embodiment, the compound is according to Formula (III) and q1 is 2 and q2 is 3. In an exemplary embodiment, the compound is according to Formula (III) and q1 is 1 and q2 is 3. In an exemplary embodiment, the compound is according to Formula (III) and q3 is 0.

In an exemplary embodiment, the compound has a structure which is a member selected from
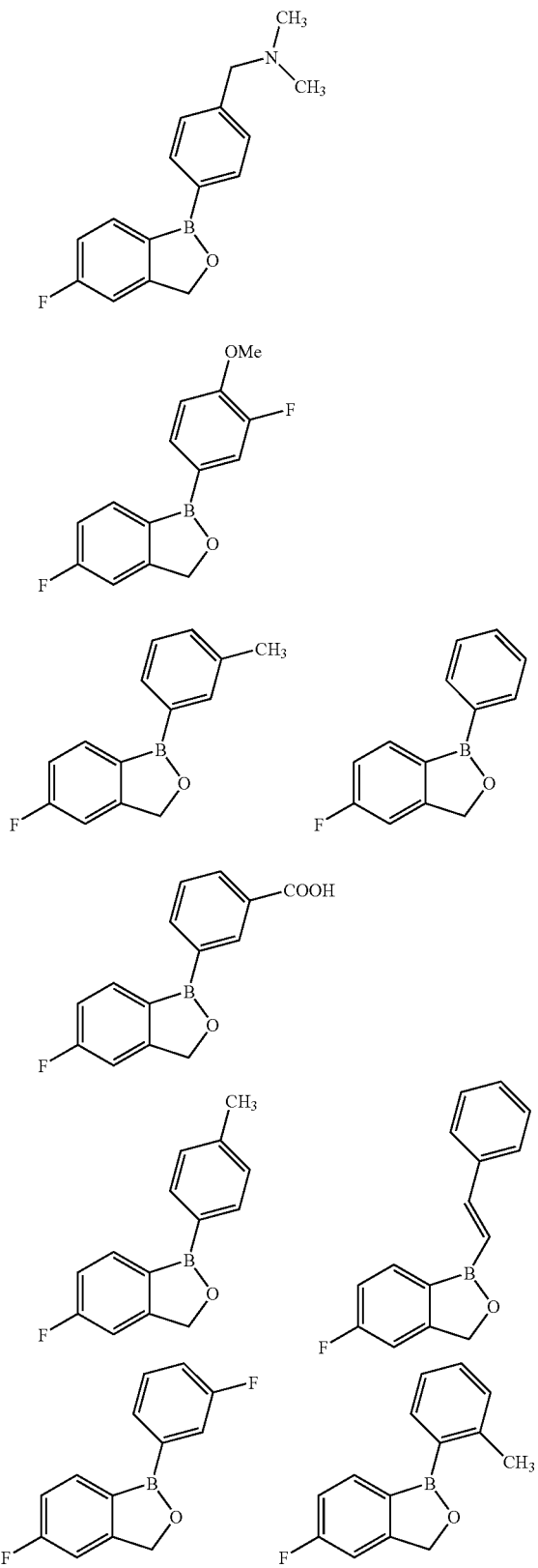
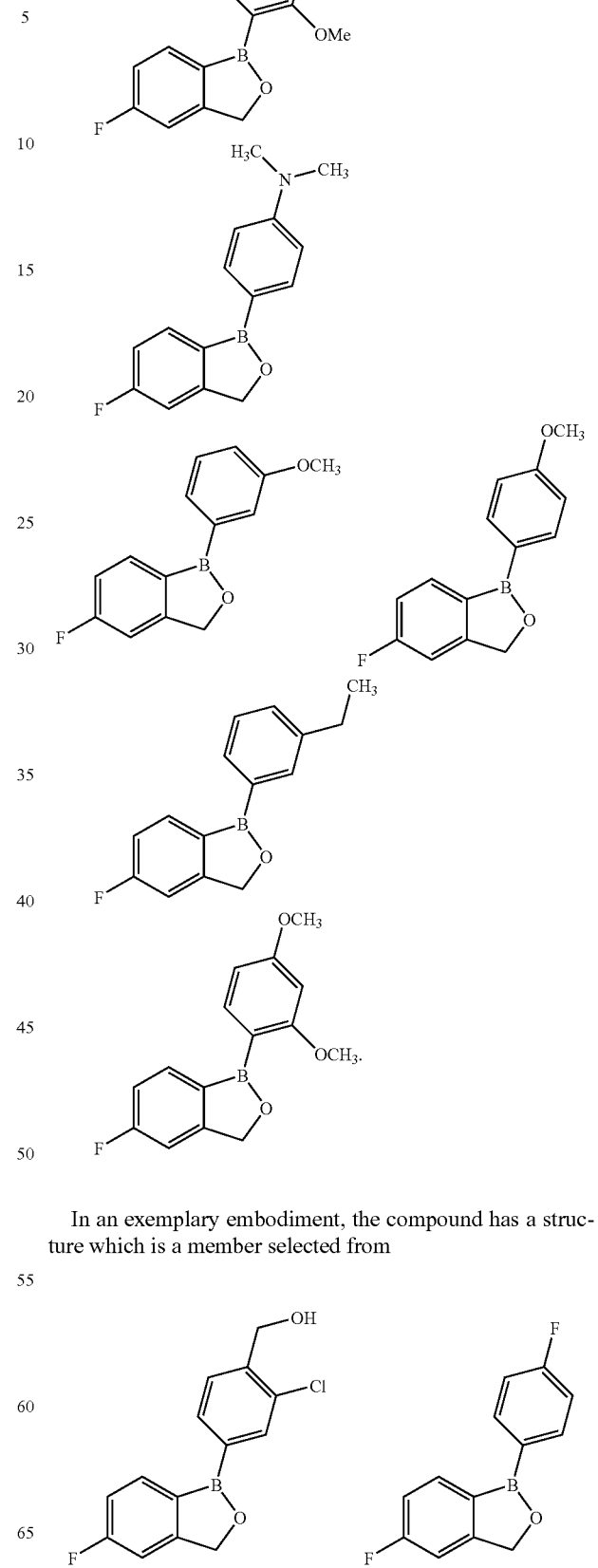
In an exemplary embodiment, the compound has a structure which is a member selected from

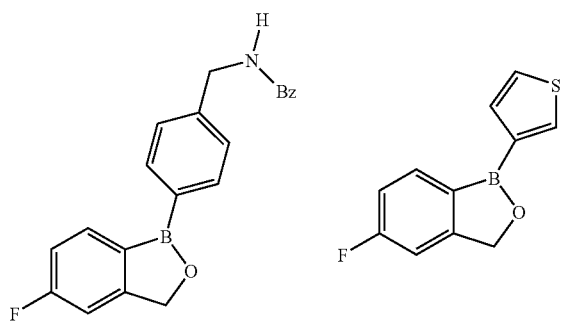
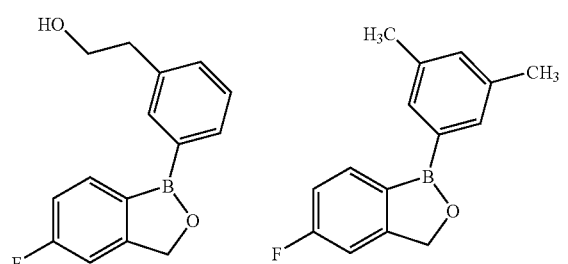
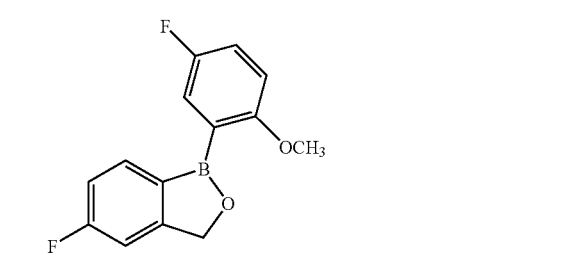
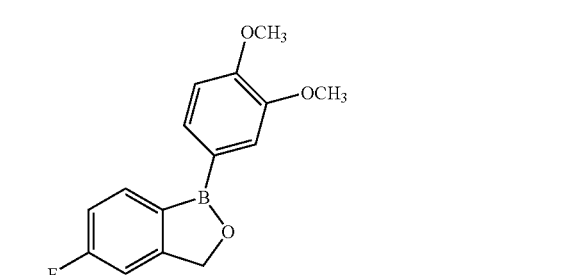
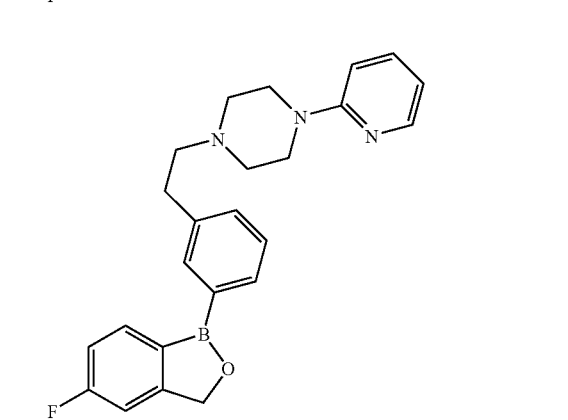
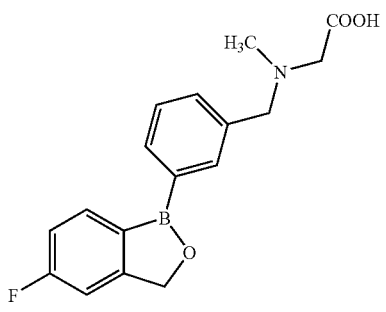
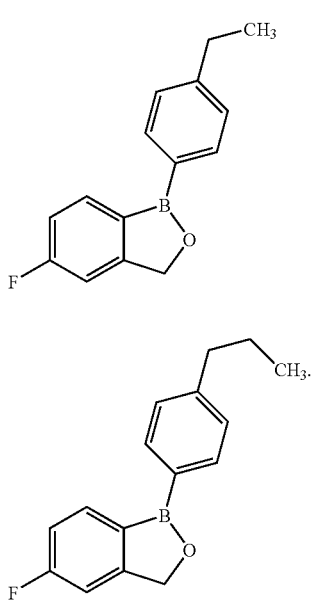
In an exemplary embodiment, the compound has a structure which is a member selected from:
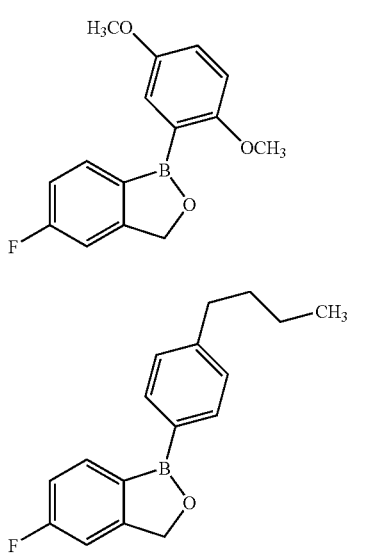

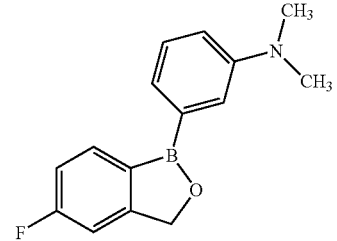
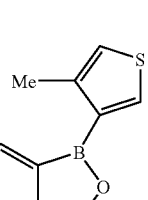
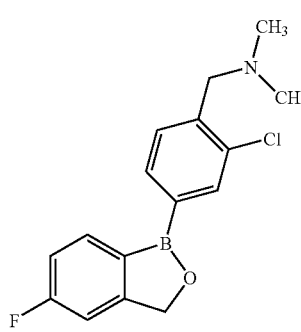
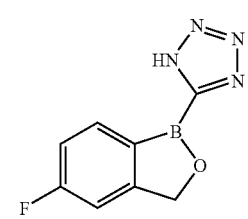
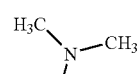
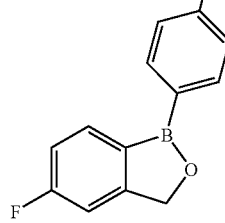
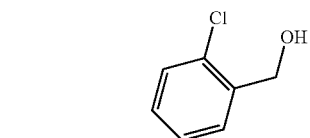
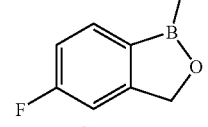
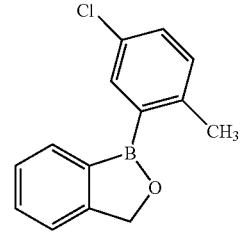
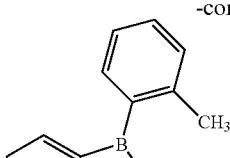
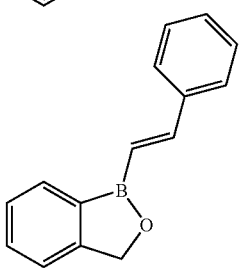
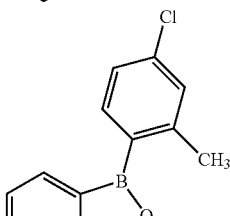
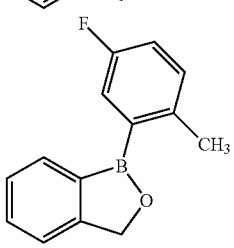
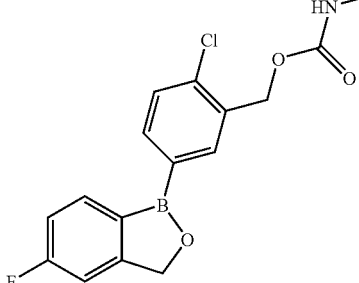
In an exemplary embodiment, the compound has a structure which is a member selected from
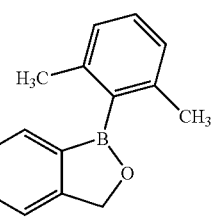

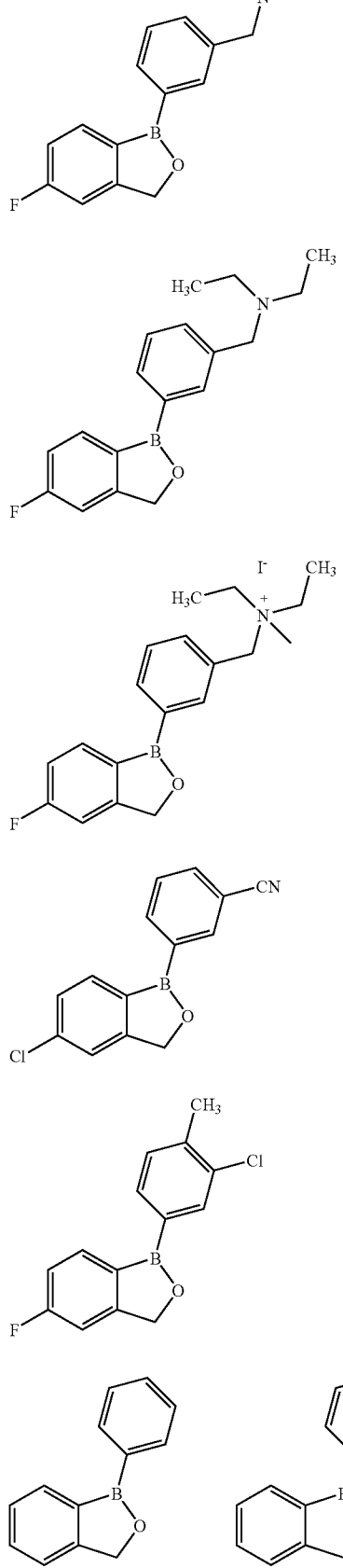
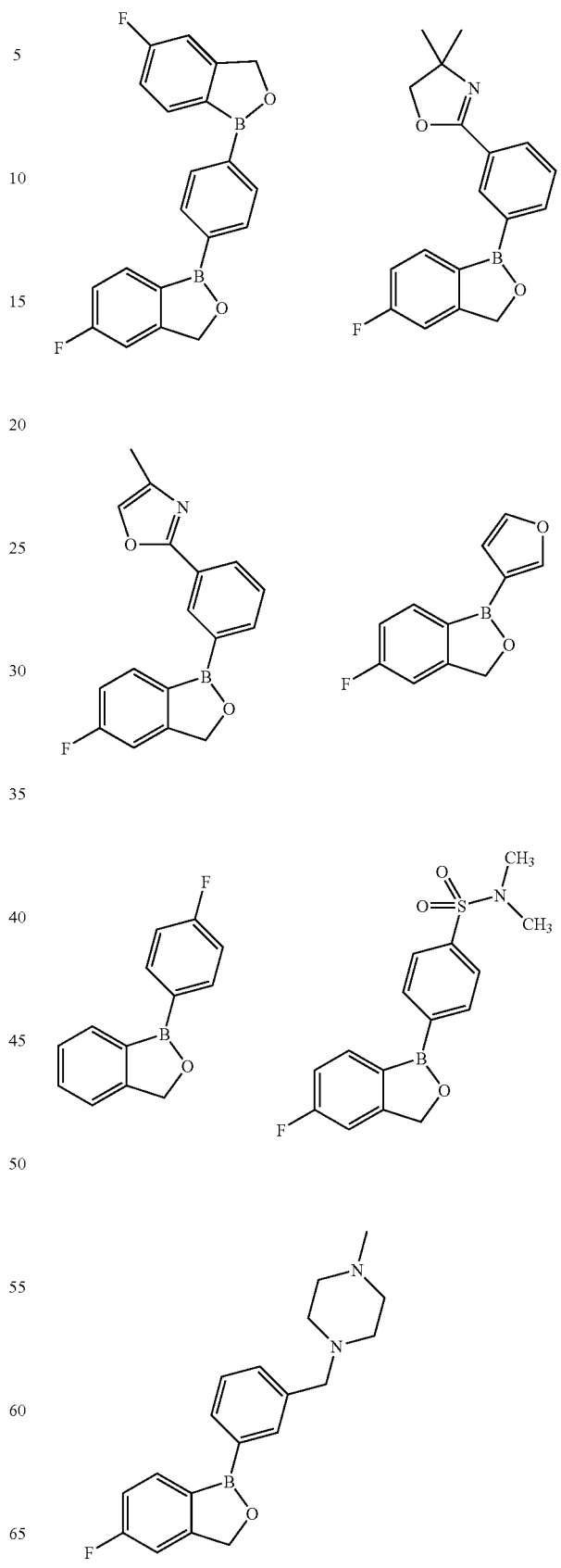

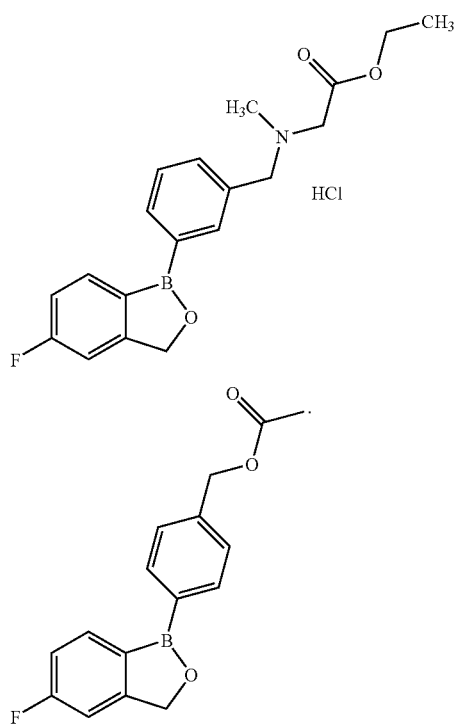
In an exemplary embodiment, the compound has a structure which is a member selected from:
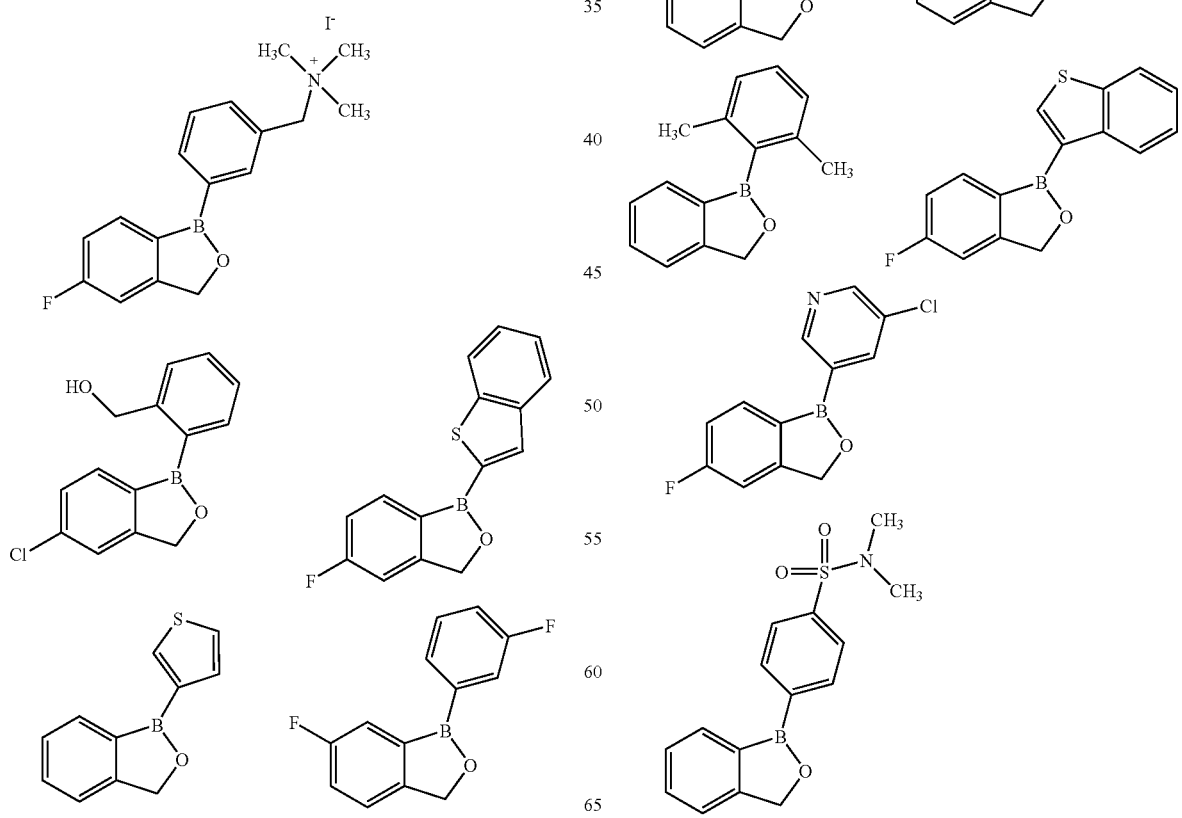
In an exemplary embodiment, the compound has a structure which is a member selected from
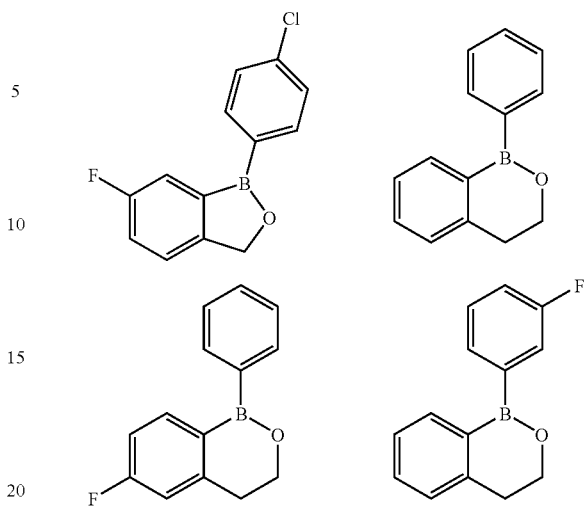

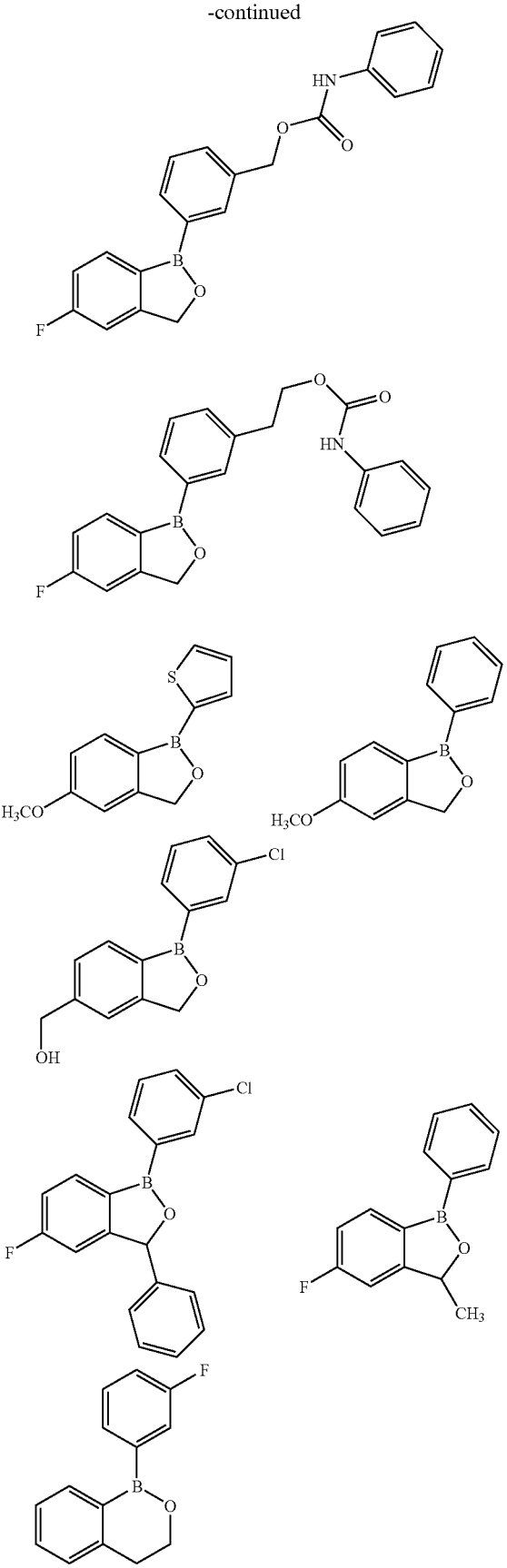
In an exemplary embodiment, the compound has a structure which is a member selected from
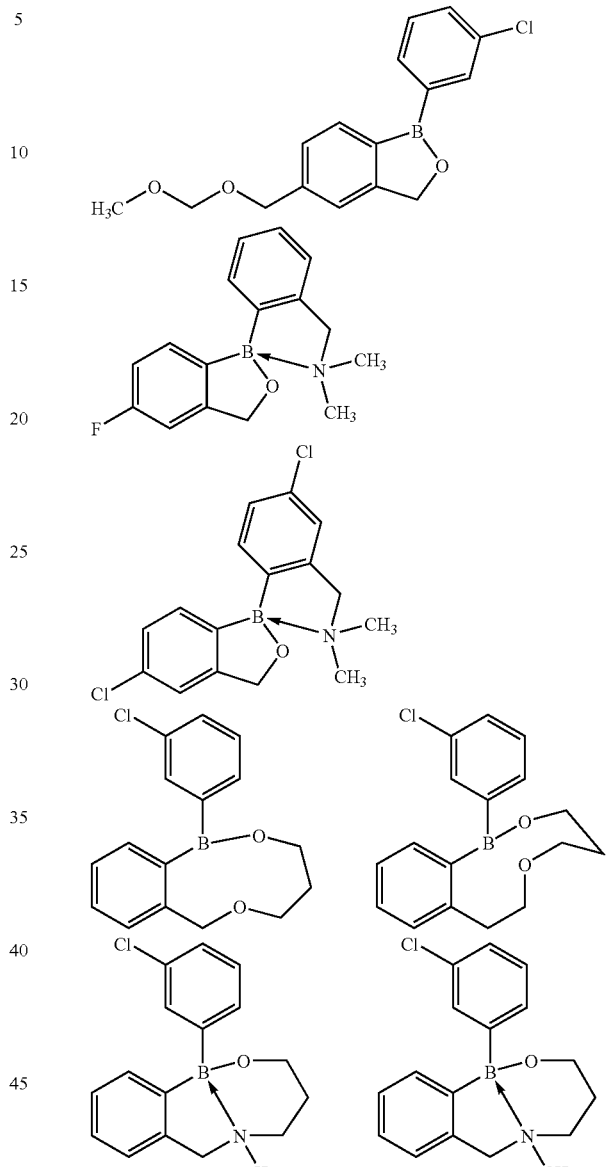
In an exemplary embodiment, the compound is
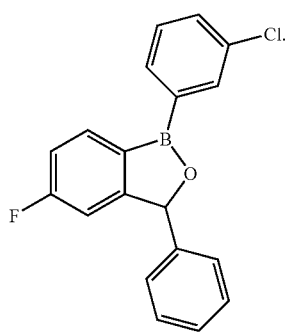

A compound described herein, such as the compounds of Formulae (I), (II) or (III), can form a hydrate with water, solvates with alcohols such as methanol, ethanol, propanol, and the like; adducts with amino compounds, such as ammonia, methylamine, ethylamine, and the like; adducts with acids, such as formic acid, acetic acid and the like; complexes with ethanolamine, quinoline, amino acids, and the like.

Preparation of Boron-containing Small Molecules

The following exemplary schemes illustrate methods of preparing boron-containing molecules of the present invention. These methods are not limited to producing the compounds shown, but can be used to prepare a variety of molecules such as the compounds and complexes described herein. The compounds of the present invention can also be synthesized by methods not explicitly illustrated in the schemes but are well within the skill of one in the art. The compounds can be prepared using readily available materials of known intermediates.

Dihydrobenzoxaboroles bearing aryl, heteroaryl, or vinyl substituents at the 1-position (9-15) were synthesized starting from 2-bromo-5-fluorobenzaldehyde (3), or 2-bromobenzyl alcohol (4a) as shown in Scheme 1. The hydroxy group of 4a,b was protected as the methoxymethyl ether to give 5a,b. Compounds 5 were treated with butyl lithium at −78° C. and the anion formed was trapped by a boronic acid ethylene glycol ester (7), prepared from the corresponding boronic acid and ethylene glycol, to give the borinic acid (8). For compounds 11 and 15, intermediate 5b was converted into the glycol ester 6, which was reacted with Grignard reagents to give 8. Finally, the protecting group was removed under acidic conditions and the free alcohol spontaneously cyclized to give the target compounds (9-15).

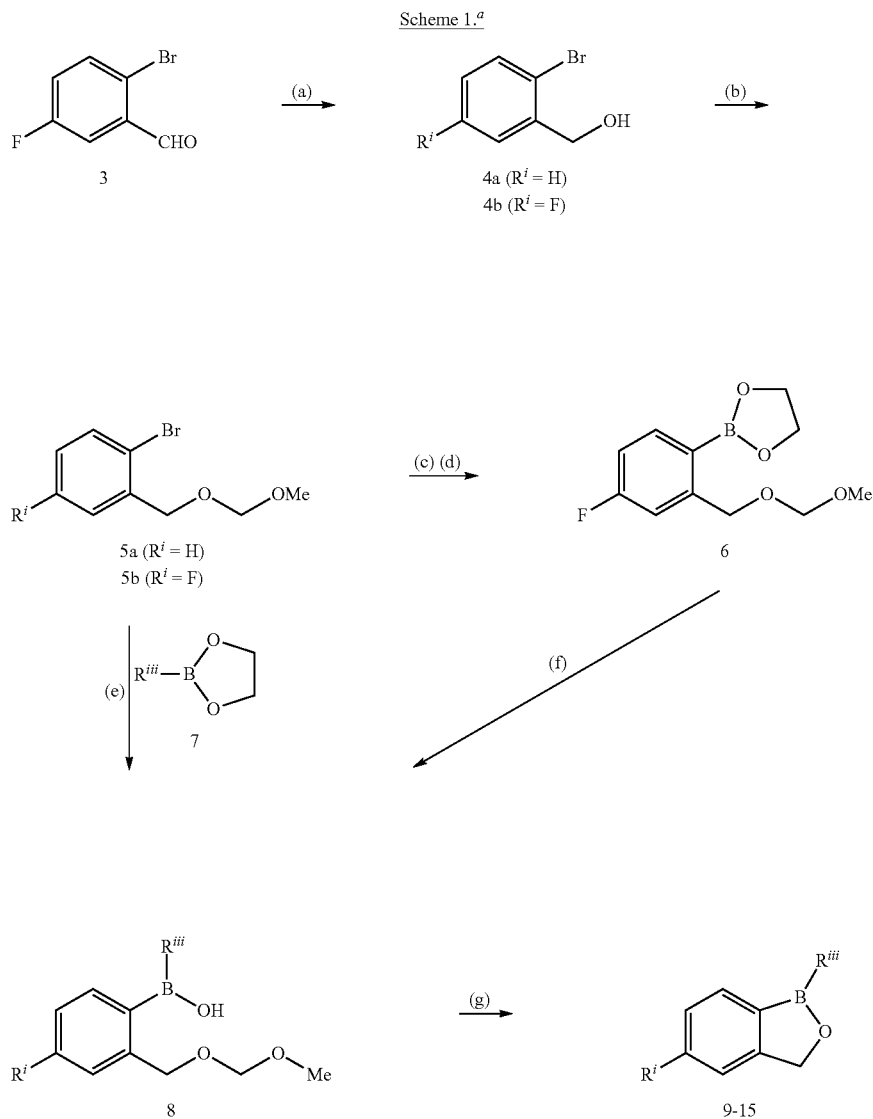

Scheme 1.$^a$

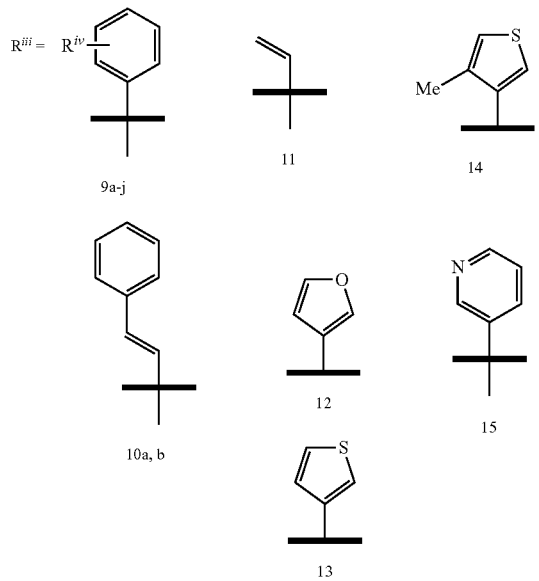

<sup>a</sup>Conditions: (a) NaBH₄, MeOH, rt; (b) MeOCH₂Cl, i-Pr₂NEt, CH₂Cl₂, rt; (c) sec-BuLi, (MeO)₃B, THF, -78° C. to rt; (d) ethylene glycol, THF or toluene, reflux; (e) n- or tert-BuLi, 7, THF, -78° C. to rt; (f) 3-bromopyridine, i-PrMgCl, THF, 0° C. (Trecourt, F.; Tetrahedron 2000, 56, 1349-1360), or vinylmagnesium bromide, THF, -78° C. to rt; (g) 6N HCl, THF, rt.

1-Hydroxy-dihydrobenzoxaboroles (19b-m) were synthesized as shown in Scheme 2. The protected o-bromobenzyl alcohol derivative (18), prepared from 16 or 17, was converted into the corresponding phenyl boronic acid. Deprotection of the methoxymethyl ether using hydrochloric acid followed by spontaneous cyclization gave the target compounds 19b-m (19c, R$^v$=Me, was prepared as a racemate). When compounds have functional groups sensitive to butyllithium, such as a nitrile group, an in-situ trap method was applied. Li, W., *J. Org. Chem.* 2002, 67, 5394-5397.

The 7-fluoro derivative (19n) was synthesized through directed ortho-metallation of 3-fluoro-benzylalcohol (20) (Scheme 3). Austin, P. W., PCT Int. Appl. WO 95/33754 (1995).

Scheme 2.<sup>a</sup>

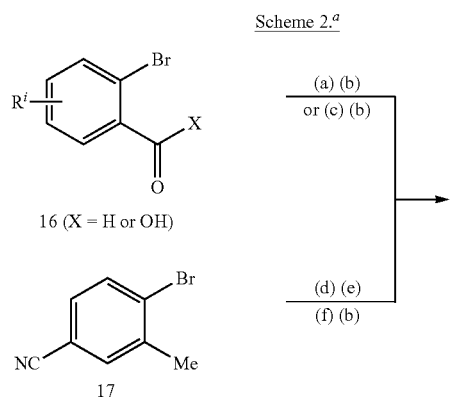

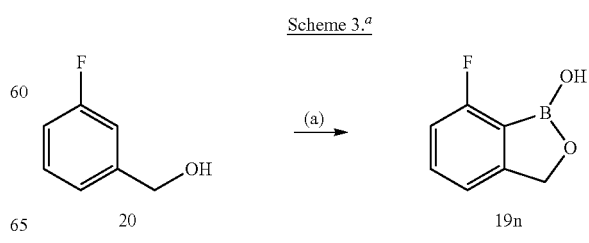

<sup>a</sup>Conditions: (a) NaBH₄, MeOH, rt, or MeMgBr, THF -78° C. to rt (when X = H), or BH₃—THF, THF, rt (when X = OH); (b) MeOCH₂Cl, i-Pr₂NEt, CH₂Cl₂, rt; (c) MeMgBr, THF, -78° C. to rt; (d) NBS, AIBN, CCl₄, reflux; (e) NaOAc, DMF, 70° C.; (f) NaOH, MeOH, reflux; (g) n-BuLi, (i-PrO)₃B, THF, -78° C. to rt; (h) 6N HCl, THF, rt.

Scheme 3.<sup>a</sup>

<sup>a</sup>Conditions: (a) sec-BuLi, (i-PrO)₃B, THF, -78° C. to rt, then HCl.

Scheme 4.[a]

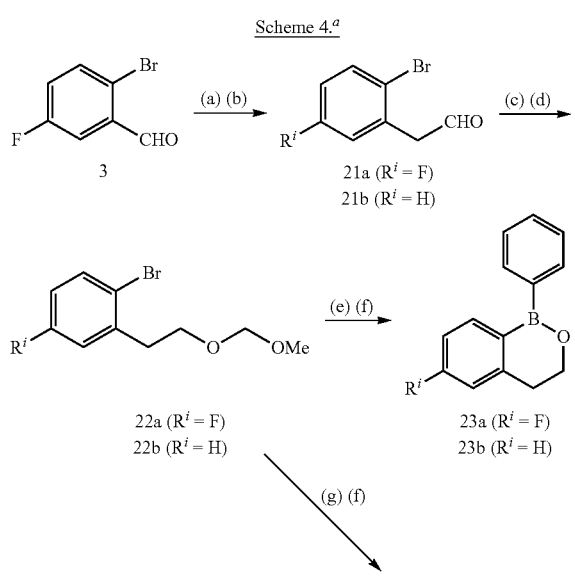

Six-membered benzoxaborin analogs were synthesized as shown in Scheme 4. For 6-fluoro analogs, the benzaldehyde (3) was subjected to a Wittig reaction and the resulting enol ether was hydrolyzed to give the phenylacetaldehyde (21a). Reduction of the carbonyl group, followed by protection of the resulting alcohol gave the methoxymethyl ether (22a), which was converted to the final products 23a and 24 using the same chemistry described previously. The unsubstituted derivative (23b) was synthesized from commercially available 2-bromophenylacetaldehyde (21b).

To determine the antifungal activity of these compounds we screened for their minimum inhibitory concentrations (MIC) against the major dermatophytes that cause onychomycosis, T. rubrum and T. mentagrophytes, and against the yeasts and molds C. albicans, C. neoformans and A. fumigatus to test for their broad spectrum activity. The antifungal agent ciclopirox, currently in use for the topical treatment of onychomycosis, was used as a reference.

Our initial lead compound was the 1-phenyl-dihydrobenzoxaborole (9a) (Table 1). This showed modest broad spectrum activity with MIC values in the range of 4-8 μg/mL. One of the first modifications made was to install a 5-fluoro-group giving compound 9b. This substitution led to a 2-8 fold increase in potency against the strains tested. Subsequently, most of the following analogs synthesized contained this fluoro substitution.

TABLE 1

Minimum inhibitory concentration (μg/mL) of boron-containing compounds compared to ciclopirox

|     | $R^i$ | Other | T. rubrum | T. mentagrophytes | C. albicans | C. neoformans | A. fumigatus |
|-----|-------|-------|-----------|-------------------|-------------|---------------|--------------|
|     | Ciclopirox | | 0.5 | 0.5 | 0.5 | 0.5 | 1 |
| 9a  | H     | $R^{iv} = H$ | 4 | 4 | 4 | 8 | 4 |
| 9b  | 5-F   | $R^{iv} = H$ | 1 | 2 | 0.5 | 2 | 2 |
| 10a | H     |       | 8 | 8 | 2 | 4 | 4 |
| 10b | 5-F   |       | ≦1 | 2 | 0.5 | 0.5 | 1 |
| 11  | 5-F   |       | 4 | 2 | 1 | 4 | 2 |
| 12  | 5-F   |       | 4 | 4 | 4 | 4 | 4 |
| 13  | 5-F   |       | 1 | 4 | 1 | 1 | 1 |
| 14  | 5-F   |       | 1 | 2 | 1 | 1 | 1 |
| 15  | 5-F   |       | 16 | 32 | 4 | 16 | 16 |
| 19a | H     | $R^v = H$ | 8 | 4 | 2 | 1 | 2 |
| 19b | 5-F   | $R^v = H$ | 1 | 1 | 0.5 | 0.25 | 0.25 |
| 19c | 5-F   | $R^v = Me$ | 32 | 16 | 16 | 32 | 16 |
| 23a | H     |       | 8 | 8 | 8 | 16 | 16 |
| 23b | 6-F   |       | 8 | 8 | 8 | 8 | 8 |
| 24  | 6-F   |       | 32 | 32 | 64 | >64 | 32 |

-continued

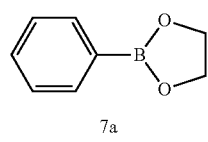

7a

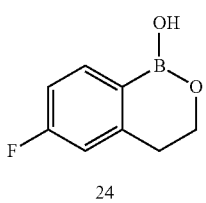

24

[a]Conditions: (a) Ph₃PCH₂OMe. Cl, tBuOK, DMF, 0° C. to rt; (b) 6N HCl, THF, reflux; (c) NaBH₄, MeOH, rt; (d) MeOCH₂Cl, i-Pr₂NEt, CH₂Cl₂, rt; (e) n-BuLi, 35, THF, -78° C. to rt; (f) 6N HCl, rt; (g) n-BuLi, (i-PrO)₃B, THF, -78° C. to rt.

We set out to determine the effect of replacing the 1-phenyl group of 9 with various substitutions. The 1-styryl-substituted dihydrobenzoxaboroles 10a and 10b led to approximately equivalent activity to our leads 9a and 9b, respectively, against all fungi tested (Table 1). Again, when $R^i$=5-F (10b) potency was improved 4-8 fold. Replacing the 1-phenyl group of 9b with 1-vinyl (11) or 1-(furan-3-yl) (12) led to an approximate 2-8 fold decrease in activity, while replacement with 1-(thiophen-3-yl) (13) or 1-(4-methylthiophen-3-yl) (14) led to approximately equal activity against all fungi except T. mentagrophytes, where there was a 4-8 fold decrease (Table 1). Interestingly, replacement of the 1-phenyl group of 9b with 1-(pyrid-3-yl) (15) showed selectivity toward non-dermatophyte strains; there was a 16-64 fold decrease in activity against the dermatophytes T. rubrum and T. mentagrophytes, but no change in activity against C. albicans and only a 4 fold reduction in activity against C. neoformans and A. fumigatus (Table 1).

In another modification to enhance hydrophilicity, we replaced the 1-phenyl group of 9a and 9b with a 1-hydroxy group to give 19a and 19b, respectively. Compounds 19a and 19b proved to have a more broad spectrum profile than 9a and 9b, respectively. They had approximately equal MIC values against all strains except *C. neoformans* where 19a and 19b showed an 8 fold increase in activity (Table 1).

In an effort to understand the effect of the 3-substitution on the oxaborole ring, we added a methyl group to the 3-position to give compound 19c. However, this modification led to an 8-32 fold decrease in activity (Table 1).

We then increased the ring size from a 5-membered oxaborole of 9a, 9b and 19b to the corresponding 6-membered oxaborin giving 23a, 23b and 24, respectively. The results of these are shown in Table 1. The 1-phenyl substituted oxaborin 23a was only approximately 2 fold less active than the oxaborole 9a. In contrast, the 5-fluoro-1-phenyl oxaborin 23b was 4-16 fold less active than the corresponding oxaborole 9b. Finally, the 1-hydroxy oxaborin 24, was 32-256 fold less active than the corresponding oxaborole 19b.

Next, we focused our attention on the 1-phenyl-dihydrobenzoxaborole scaffold (9) to determine the effect of substitutions on the 1-phenyl ring and examples of these are shown in Table 2. As before, in all cases, compounds with $R^i$=F were more potent than compounds with $R^i$=H. The lead compound 9b remained the most potent with only the 3'-Cl analog (9f) showing near equivalent activity.

In a final study, we synthesized various analogs of 5-fluoro-1,3-dihydro-1-hydroxy-2,1-benzoxaborole (19b) to determine the structure-activity relationship of this scaffold. The results of this study are shown in Table 3. We first substituted the 5-F group with other groups, giving 19d-19i, to determine the optimum substituent for this position.

TABLE 2

Minimum inhibitory concentration (μg/mL) of 1,3-dihydro-1-phenyl-2,1-benzoxaborole compounds (9)

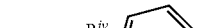

| # | $R^i$ | $R^{iv}$ | T. rubrum | T. mentagrophytes | C. albicans | C. neoformans | A. fumigatus |
|---|---|---|---|---|---|---|---|
| 9a | H | H | 4 | 4 | 4 | 8 | 4 |
| 9b | F | H | 1 | 2 | 0.5 | 2 | 2 |
| 9c | H | 3'-Cl | 16 | 8 | 8 | 4 | 8 |
| 9d | H | 3'-F | 8 | 16 | 4 | 4 | 8 |
| 9e | H | 4'-F | 8 | 4 | 4 | 2 | 2 |
| 9f | F | 3'-Cl | 4 | 8 | 0.25 | 0.5 | 2 |
| 9g | F | 3'-F | 1 | 2 | 0.5 | 1 | 1 |
| 9h | F | 4'-F | 4 | 4 | 1 | 1 | 2 |
| 9i | F | 3'-Me | 2 | 4 | 1 | 0.5 | 0.5 |
| 9j | F | 4'-Me | 2 | 2 | 0.5 | 0.5 | 0.5 |

TABLE 3

Minimum inhibitory concentration (μg/mL) of 1,3-dihydro-1-hydroxy-2,1-benzoxaborole compounds (19)

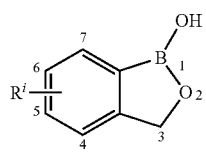

| # | $R^i$ | T. rubrum | T. mentagrophytes | C. albicans | C. neoformans | A. fumigatus |
|---|---|---|---|---|---|---|
| 19b | 5-F | 1 | 1 | 0.5 | 0.25 | 0.25 |
| 19d | 5-Cl | 1 | 2 | 1 | 2 | 1 |
| 19e | 5-Me | 8 | 4 | 2 | 8 | 2 |
| 19f | 5-$CF_3$ | 8 | 8 | 16 | 16 | 8 |
| 19g | 5-NC | 16 | 16 | 8 | 8 | 16 |
| 19h | 5-MeO | 64 | 32 | >64 | >64 | >64 |
| 19i | 5-$HOCH_2$ | 64 | 64 | >64 | >64 | >64 |
| 19j | 6,7-benzo | 4 | 2 | 32 | 32 | 32 |
| 19k | 5-F-6-F | 4 | 4 | 4 | 2 | 2 |
| 19l | 4-F | 16 | 16 | 64 | 32 | 32 |
| 19m | 6-F | 16 | 32 | 16 | 32 | 8 |
| 19n | 7-F | 16 | 16 | 32 | 32 | 4 |

In another modification, we found that addition of a second fluoro-group at the 6-position, giving 19k, effectively offset the additional potency provided by the 5-fluoro substituent. In a final modification we moved the fluoro group to other positions around the benzo ring giving compounds 19l-n, and found that the optimum position for the fluoro group remained at the 5-position.

III. Methods of Inhibiting Microorganism Growth or Killing Microorganisms

In another aspect, the invention provides a method of inhibiting the growth of a microorganism, or killing a microorganism, or both, comprising contacting the microorganism with a compound described herein. In an exemplary embodiment, the compound is according to Formulae (I), (II) and/or (III). In an exemplary embodiment, there is a proviso that when M is F, R* is not a member selected from:

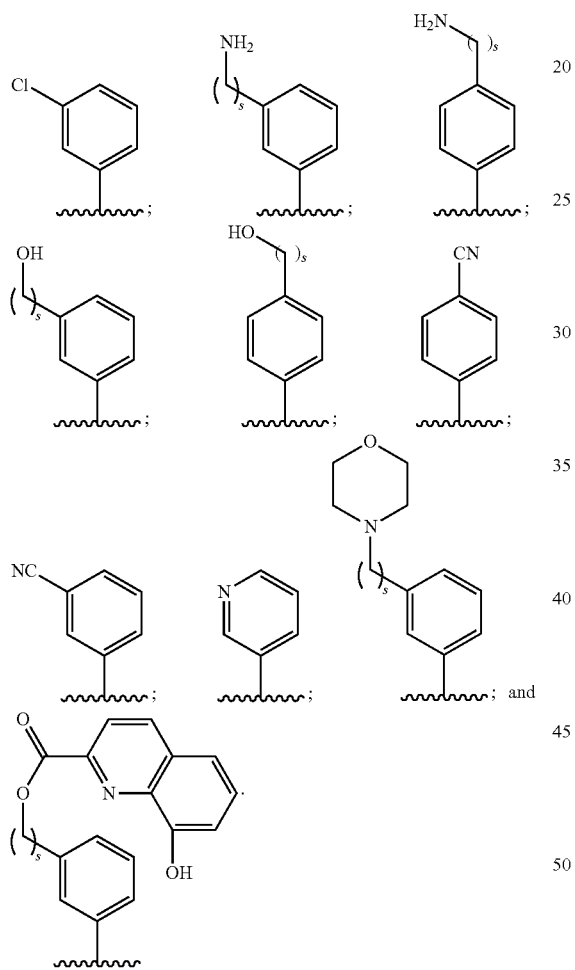

In another exemplary embodiment, there is a proviso that when M is Cl, R* is not a member selected from:

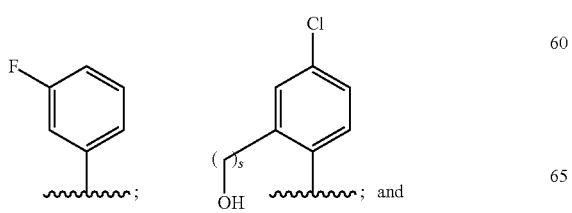

In another exemplary embodiment, there is a proviso that when M is H, R* is not a member selected from:

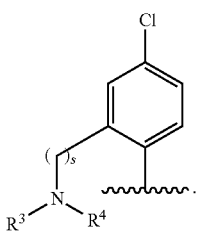

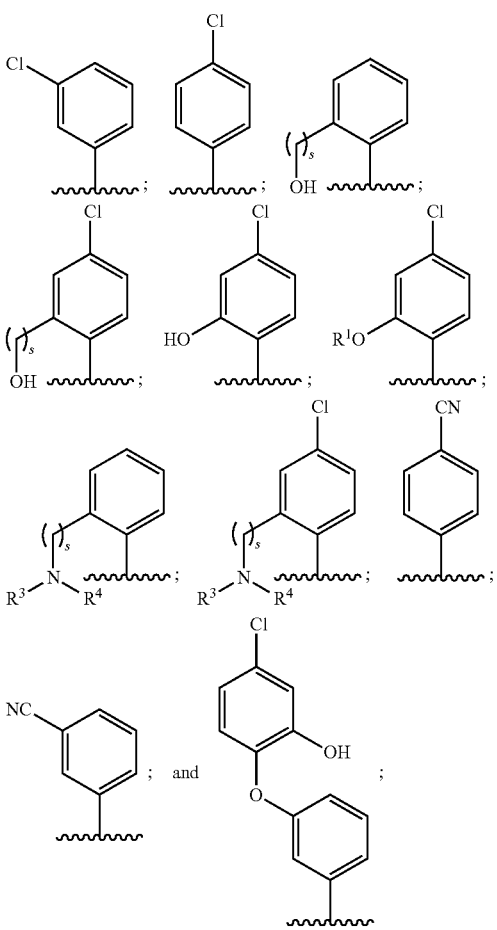

in which the index s is an integer selected from 1 and 2. $R^3$ and $R^4$ are members independently selected from methyl and ethyl.

In another exemplary embodiment, there is a proviso that when M is $OCH_3$, R* is not a member selected from:

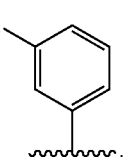

In another exemplary embodiment, there is a proviso that when M¹ is F, R* is not a member selected from:

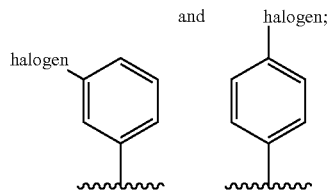

including salts thereof.

Microorganisms are members selected from fungi, yeast, viruses, bacteria and parasites. In another exemplary embodiment, the microorganism is inside, or on the surface of an animal. In an exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is a member selected from a fungus and a yeast. In another exemplary embodiment, the fungus or yeast is a member selected from *Candida* species, *Trichophyton* species, *Microsporiur* species, *Aspergillus* species, *Cryptococcus* species, *Blastomyces* species, *Cocciodiodes* species, *Histoplasma* species, *Paracoccidiodes* species, *Phycomycetes* species, *Malassezia* species, *Fusarium* species, *Epidermophyton* species, *Scytalidium* species, *Scopulariopsis* species, *Alternaria* species, *Penicillium* species, *Phialophora* species, *Rhizopus* species, *Scedosporium* species and Zygomycetes class. In another exemplary embodiment, the fungus or yeast is a member selected from *Aspergillus fumigatus* (*A. fumigatus*), *Blastomyces dermatitidis*, *Candida Albicans* (*C. albicans*, both fluconazole sensitive and resistant strains), *Candida glabrata* (*C. glabrata*), *Candida krusei* (*C. krusei*), *Cryptococcus neoformans* (*C. neoformans*), *Candida parapsilosis* (*C. parapsilosis*), *Candida tropicalis* (*C. tropicalis*), *Cocciodiodes immitis*, *Epidermophyton floccosum* (*E. floccosum*), *Fusarium solani* (*F. solani*), *Histoplasma capsulatum*, *Malassezia furfur* (*M. furfur*), *Malassezia pachydermatis* (*M. pachydermatis*), *Malassezia sympodialis* (*M. sympodialis*), *Microsporum audouinii* (*M. audouinii*), *Microsporu canis* (*M. canis*), *Microsporum gypseum* (*M. gypseum*), *Paracoccidiodes brasiliensis* and *Phycomycetes* spp, *Trichophyton rentagrophytes* (*T. mentagrophytes*), *Trichophyton rubrum* (*T. rubrum*), *Trichophyton tonsurans* (*T. tonsurans*). In another exemplary embodiment, the fungus or yeast is a member selected from *Trichophyton concentricum*, *T. violaceum*, *T. schoenleinii*, *T. verrucosum*, *T. soudanense*, *Microsporum gypseum*, *M. equinum*, *Candida guilliermondii*, *Malassezia globosa*, *M. obtuse*, *M. restricta*, *M. slooffiae*, and *Aspergillus flavus*. In another exemplary embodiment, the fungus or yeast is a member selected from dermatophytes, *Trichophyton*, *Microsporum*, *Epidermophyton* and yeast-like fungi.

In an exemplary embodiment, the microorganism is a bacteria. In an exemplary embodiment, the bacteria is a gram-positive bacteria. In another exemplary embodiment, the gram-positive bacteria is a member selected from *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species and *Streptomyces* species. In another exemplary embodiment, the bacteria is a gram-negative bacteria. In another exemplary embodiment, the gram-negative bacteria is a member selected from *Acinetobacter* species, *Neisseria* species, *Pseudomonas* species, *Brucella* species, *Agrobacterium* species, *Bordetella* species, *Escherichia* species, *Shigelia* species, *Yersinia* species, *Salmonella* species, *Klebsiella* species, *Enterobacter* species, *Haemophilus* species, *Pasteurella* species, *Streptobacillus* species, spirochetal species, *Campylobacter* species, *Vibrio* species and *Helicobacter* species. In another exemplary embodiment, the bacterium is a member selected from *Propionibacterium acnes*; *Staphylococcus aureus*; *Staphylococcus epidermidis*, *Staphylococcus saprophyticus*; *Streptococcus pyogenes*; *Streptococcus agalactiae*; *Streptococcus pneumoniae*; *Enterococcus faecalis*; *Enterococcus faecium*; *Bacillus anthracis*; *Mycobacterium avium-intracellulare*; *Mycobacterium tuberculosis*, *Acinetobacter baumanii*; *Corynebacterium diphtheria*; *Clostridium perfringens*; *Clostridium botulinum*; *Clostridium tetani*; *Neisseria gonorrhoeae*; *Neisseria meningitidis*; *Pseudomonas aeruginosa*; *Legionella pneumophila*; *Escherichia coli*; *Yersinia pestis*; *Haemophilus influenzae*; *Helicobacter pylori*; *Campylobacter fetus*; *Campylobacter jejuni*; *Vibrio cholerae*; *Vibrio parahemolyticus*; *Trepomena pallidum*; *Actinomyces israelii*; *Rickettsia prowazekii*; *Rickettsia rickettsii*; *Chlamydia trachomatis*; *Chlamydia psittaci*; *Brucella abortus*; *Agrobacterium tumefaciens*; and *Francisella tularensis*.

In an exemplary embodiment, the microorganism is a bacteria, which is a member selected from acid-fast bacterium, including *Mycobacterium* species; bacilli, including *Bacillus* species, *Corynebacterium* species (also *Propionibacterium*) and *Clostridium* species; filamentous bacteria, including *Actinomyces* species and *Streptomyces* species; bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species; spirochetal species, *Campylobacter* species, *Vibrio* species; and intracellular bacteria including *Rickettsiae* species and *Chlamydia* species.

The compounds of the invention are useful as antibiotics for the treatment of diseases of both animals and humans, including but not limited to actinomycosis, anthrax, bacterial dysentery, botulism, brucellosis, cellulitis, cholera, conjunctivitis, cystitis, diphtheria, bacterial endocarditis, epiglottitis, gangerene, gastroenteritis, glanders, gonorrhea, Legionnaire's disease, leptospirosis, bacterial meningitis, plague, bacterial pneumonia, otitis media, puerperal sepsis, pyronephritis, rheumatic fever, Rocky Mountain spotted fever, scarlet fever, sinusitis, streptococcal pharyngitis, syphilis, tetanus, toxic shock syndrome, tuberculosis, tularemia, typhoid fever, typhus, and pertussis.

In an exemplary embodiment, the microorganism is a virus. In an exemplary embodiment, the virus is a member selected from hepatitis A-B, human rhinoviruses, Yellow fever virus, human respiratory coronaviruses, Severe acute respiratory syndrome (SARS), respiratory syncytial virus, influenza viruses, parainfluenza viruses 1-4, human immunodeficiency virus 1 (HIV-1), human immunodeficiency virus 2 (HIV-2), Herpes simplex virus 1 (HSV-1), Herpes simplex virus 2 (HSV-2), human cytomegalovirus (HCMV), Varicella zoster virus, Epstein-Barr (EBV), polioviruses, coxsackieviruses, echoviruses, rubella virus, neuroderma-tropic virus, variola virus, papoviruses, rabies virus, dengue virus, West Nile virus and SARS virus. In another exemplary embodiment, the virus is a member selected from *picornaviridae, flaviviridae, coronaviridae, paramyxoviridae, orthomyxoviridae, retroviridae, herpesviridae* and *hepadnaviridae*. In another exemplary embodiment, the virus is a member selected from a virus included in the following table:

TABLE A

| Virus Category | Pertinent Human Infections |
|---|---|
| RNA Viruses | |
| Picornaviridae | Polio |
| | Human hepatitis A |
| | Human rhinovirus |
| Togaviridae and | Rubella - German measles |
| Flaviviridae | Yellow fever |
| Coronaviridae | Human respiratory coronavirus (HCV) |
| | Severe acute respiratory syndrome (SAR) |
| Rhabdoviridae | Lyssavirus - Rabies |
| Paramyxoviridae | Paramyxovirus - Mumps |
| | Morbillvirus - measles |
| | Pneumovirus - respiratory syncytial virus |
| Orthomyxoviridae | Influenza A-C |
| Bunyaviridae | Bunyavirus - Bunyamwera (BUN) |
| | Hantavirus - Hantaan (HTN) |
| | Nairevirus - Crimean-Congo hemorrhagic fever (CCHF) |
| | Phlebovirus - Sandfly fever (SFN) |
| | Uukuvirus - Uukuniemi (UUK) |
| | Rift Valley Fever (RVFN) |
| Arenaviridae | Junin - Argentine hemorrhagic fever |
| | Machupo - Bolivian hemorrhagic fever |
| | Lassa - Lassa fever |
| | LCM - aseptic lymphocyctic choriomeningitis |
| Reoviridae | Rotovirus |
| | Reovirus |
| | Orbivirus |
| Retroviridae | Human immunodeficiency virus 1 (HIV-1) |
| | Human immunodeficiency virus 2 (HIV-2) |
| | Simian immunodeficiency virus (SIV) |
| DNA Viruses | |
| Papovaviridae | Pediatric viruses that reside in kidney |
| Adenoviridae | Human respiratory distress and some deep-seated eye infections |
| Parvoviridae | Human gastro-intestinal distress (Norwalk Virus) |
| Herpesviridae | Herpes simplex virus 1 (HSV-1) |
| | Herpes simplex virus 2 (HSV-2) |
| | Human cytomegalovirus (HCMV) |
| | Varicella zoster virus (VZV) |
| | Epstein-Barr virus (EBV) |
| | Human herpes virus 6 (HHV6) |
| Poxviridae | Orthopoxvirus is sub-genus for smallpox |
| Hepadnaviridae | Hepatitis B virus (HBV) |
| | Hepatitis C virus (HCV) |

In another exemplary embodiment, the microorganism is a parasite. In an exemplary embodiment, the parasite is a member selected from *Plasmodium falciparum, P. vivax, P. ovale P. malariae, P. berghei, Leishmania donovani, L. infantum, L. chagasi, L. mexicana, L. amazonensis, L. venezuelensis, L. tropics, L. major, L. minor, L. aethiopica, L. Biana braziliensis, L. (V.) guyanensis, L. (V.) panamensis, L. (V.) peruviana, Trypanosoma brucei rhodesiense, T. brucei gambiense, T. cruzi, Giardia intestinalis, G. lambda, Toxoplasma gondii, Entamoeba histolytica, Trichomonas vaginalis, Pneumocystis carinii,* and *Cryptosporidium parvum.*

IV. Methods of Treating or Preventing Infections

In another aspect, the invention provides a method of treating or preventing an infection, or both. The method includes administering to the animal a therapeutically effective amount of a compound described herein, sufficient to treat or prevent said infection. In an exemplary embodiment, the compound of the invention is according to Formulae (I), (II) and/or (III). In an exemplary embodiment, there is a proviso that when M is F, R* is not a member selected from:

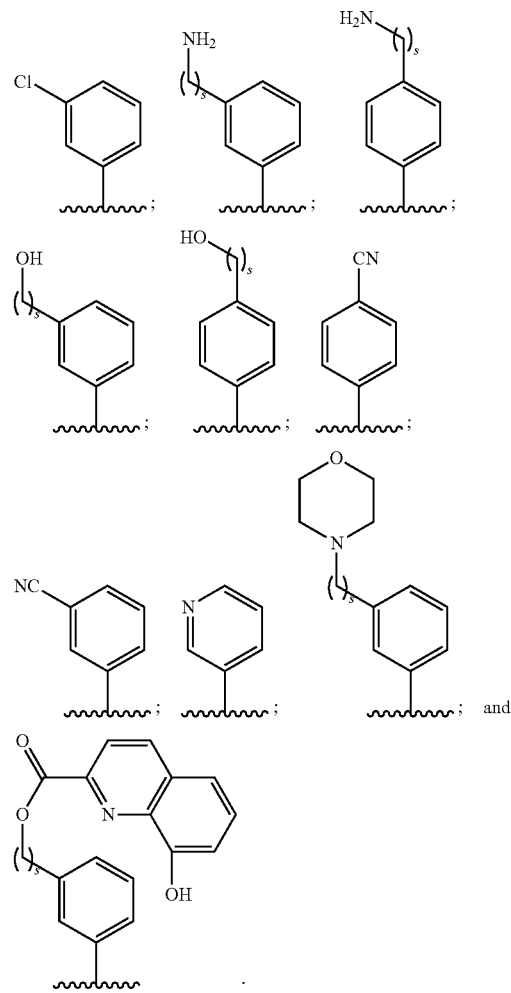

In another exemplary embodiment, there is a proviso that when M is Cl, R* is not a member selected from:

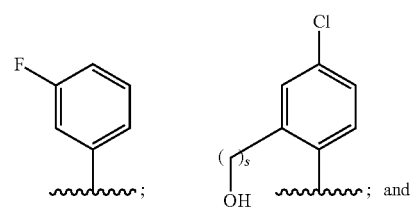

-continued

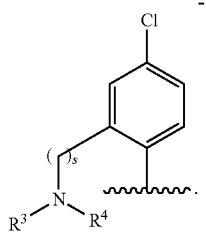

In another exemplary embodiment, there is a proviso that when M is H, R* is not a member selected from:

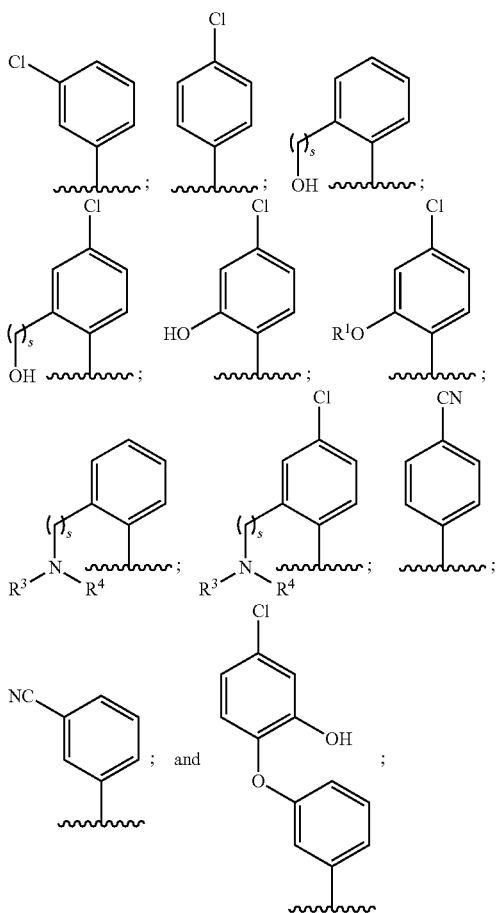

in which the index s is an integer selected from 1 and 2. $R^3$ and $R^4$ are members independently selected from methyl and ethyl.

In another exemplary embodiment, there is a proviso that when M is $OCH_3$, R* is not a member selected from:

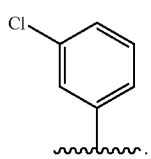

In another exemplary embodiment, there is a proviso that when $M^1$ is F, R* is not a member selected from:

including salts thereof. In another exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a member selected from a human, cattle, goat, pig, sheep, horse, cow, bull, dog, guinea pig, gerbil, rabbit, cat, chicken and turkey. In another exemplary embodiment, the infection is a member selected from a systemic infection, a cutaneous infection, and an ungual or periungual infection.

IV. a) Methods of Treating of Preventing Ungual and/or Periungual Infections

In another aspect, the invention provides a method of treating or preventing an ungual and/or periungual infection. The method includes administering to the animal a therapeutically effective amount of a compound described herein, sufficient to treat or prevent said infection. In another exemplary embodiment, the method includes administering the compound of the invention at a site which is a member selected from the skin, nail, hair, hoof, claw and the skin surrounding the nail, hair, hoof and claw.

IV. a) 1) Onychomycosis

Onychomycosis is a disease of the nail caused by yeast, dermatophytes, or other molds, and represents approximately 50% of all nail disorders. Toenail infection accounts for approximately 80% of onychomycosis incidence, while fingernails are affected in about 20% of the cases. Dermatophytes are the most frequent cause of nail plate invasion, particularly in toenail onychomycosis. Onychomycosis caused by a dermatophyte is termed Tinea unguium. *Trichophyton rubrum* is by far the most frequently isolated dermatophyte, followed by *T. mentagrophytes*. Distal subungual onychomycosis is the most common presentation of tinea unguium, with the main site of entry through the hyponychium (the thickened epidermis underneath the free distal end of a nail) progressing in time to involve the nail bed and the nail plate. Discoloration, onycholysis, and accumulation of subungual debris and nail plate dystrophy characterize the disease. The disease adversely affects the quality of life of its victims, with subject complaints ranging from unsightly nails and discomfort with footwear, to more serious complications including secondary bacterial infections.

Many methods are known for the treatment of fungal infections, including the oral and topical use of antibiotics (e.g., nystatin and amphotericin B), imidazole anti-fungal agents such as miconazole, clotrimazole, fluconazole, econazole and sulconazole, and non-imidazole fungal agents such as the allylamine derivatives terbinafine and naftifine, and the benzylamine butenafine.

However, onychomycosis has proven to be resistant to most treatments. Nail fungal infections reside in an area difficult to access by conventional topical treatment and antifungal drugs cannot readily penetrate the nail plate to reach the infection sites under the nail. Therefore, onychomycosis has traditionally been treated by oral administration of anti-fungal drugs; however, clearly this is undesirable due to the potential for side effects of such drugs, in particular those caused by the more potent anti-fungal drugs such as itraconazole and ketoconazole. An alternative method of treatment of onychomycosis is by removal of the nail before treating with a topically active anti-fungal agent; such a method of treatment is equally undesirable. Systemic antimycotic agents require prolonged use and have the potential for significant side effects. Topical agents have usually been of little benefit, primarily because of poor penetration of the anti-fungal agents into and through the nail mass.

In an exemplary embodiment, the invention provides a method of treating or preventing onychomycosis. The method includes administering to the animal a therapeutically effective amount of a pharmaceutical formulation of the invention, sufficient to treat or prevent onychomycosis. In another exemplary embodiment, the method includes administering the pharmaceutical formulation of the invention at a site which is a member selected from the skin, nail, hair, hoof, claw and the skin surrounding the nail, hair, hoof and claw.

IV. a) 2) Other Unugal and Periungual Infections

In an exemplary embodiment, the invention provides a method of treating or preventing an ungual or periungual infection in an animal, such as a mammal. This method comprising administering to the mammal a therapeutically effective amount of a compound of the invention, thereby treating or preventing the ungual or periungual infection. In an exemplary embodiment, the ungual or periungual infection is a member selected from: chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, nail dystrophy (trachyonychia), and dermatological diseases with an effect on the nails, such as psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, pityriasis rubra pilaris, palmoplantar keratoderma, contact eczema, polymorphic erythema, scabies, Bazex syndrome, systemic scleroderma, systemic lupus erythematosus, chronic lupus erythematosus, dermatomyositus.

The compounds and pharmaceutical formulations of the invention useful for ungual and periungual applications also find application in the cosmetics field, in particular for the treatment of irregularities of the nails, koilonychias, Beau's lines, longitudinal ridging, ingrown nails.

In an exemplary embodiment, the infection is of the skin, nail, hair, claw or hoof, hair, ear and eye and is a member selected from Sporotrichosis, Mycotic keratitis, Extension oculomycosis, Endogenous oculomycosis, Lobomycosis, Mycetoma, Piedra, Pityriasis versicolor, Tinea corporis, Tinea cruris, Tinea pedis, Tinea barbae, Tinea capitis, Tinea nigra, Otomycosis, Tinea favosa, Chromomycosis, and Tinea Imbricata.

IV. b) Methods of Treating Systemic Diseases

In another aspect, the invention provides a method of treating a systemic disease. The method involves contacting an animal with a compound described herein. The method of delivery for treatment of systemic diseases can be oral, intravenous or transdermal.

In an exemplary embodiment, the infection is systemic and is a member selected from candidiasis, aspergillosis, coccidioidomycosis, cryptococcosis, histoplasmosis, blastomycosis, paracoccidioidomycosis, zygomycosis, phaeohyphomycosis and rhinosporidiosis.

IV. c) Methods of Treating Diseases Involving Viruses

The compounds of the invention are useful for the treatment of diseases of both animals and humans, involving viruses. In an exemplary embodiment, the disease is a member selected from hepatitis A-B-C, yellow fever, respiratory syncytial, influenza, AIDS, herpes simplex, chicken pox, varicella zoster, and Epstein-Barr disease.

IV. d) Methods of Treating Diseases Involving Parasites

The compounds of the invention are useful for the treatment of diseases of both animals and humans, involving parasites. In an exemplary embodiment, the disease is a member selected from malaria, Chagas' disease, Leishmaniasis, African sleeping sickness (African human trypanosomiasis), giardiasis, toxoplasmosis, amebiasis and cryptosporidiosis.

V. Methods of Nail Penetration

It is believed that poor penetration of the active agent through the hoof or nail plate and/or excessive binding to keratin, (the major protein in nails and hair) are the reasons for the poor efficacy of 8% ciclopirox w/w in commercial lacquer and other topical treatments that have failed in clinical trials. In mild cases of onychomycosis, the pathogenic fungi reside in the nail plate only. In moderate to severe cases the pathogenic fungi establish a presence in the nail plate and in the nail bed. If the infection is cleared from the nail plate but not from the nail bed, the fungal pathogen can re-infect the nail plate. Therefore, to effectively treat onychomycosis, the infection must be eliminated from the nail plate and the nail bed. To do this, the active agent must penetrate and disseminate substantially throughout the nail plate and nail bed.

It is believed that in order for an active agent to be effective once disseminated throughout the infected area, it must be bioavailable to the fungal pathogen and cannot be so tightly and/or preferentially bound to keratin that the drug is rendered inactive.

An understanding of the morphology of the nail plate suggests certain physicochemical properties of an active agent that would facilitate penetration of the nail plate. The desired physicochemical properties are described throughout. The tested compounds of the present invention are able to penetrate the nail plate and were also active against *Trichophyton rubrum* and mentagrophytes and other species. In addition, the tested compounds are also active against *Trichophyton rubrum* in the presence of 5% keratin powder.

In another aspect, the invention provides a method of delivering a compound described herein from the dorsal layer of the nail plate to the nail bed. In an exemplary embodiment, the compound has a structure according to Formulae (I), (II)

and/or (III). In an exemplary embodiment, there is a proviso that when M is F, R* is not a member selected from:

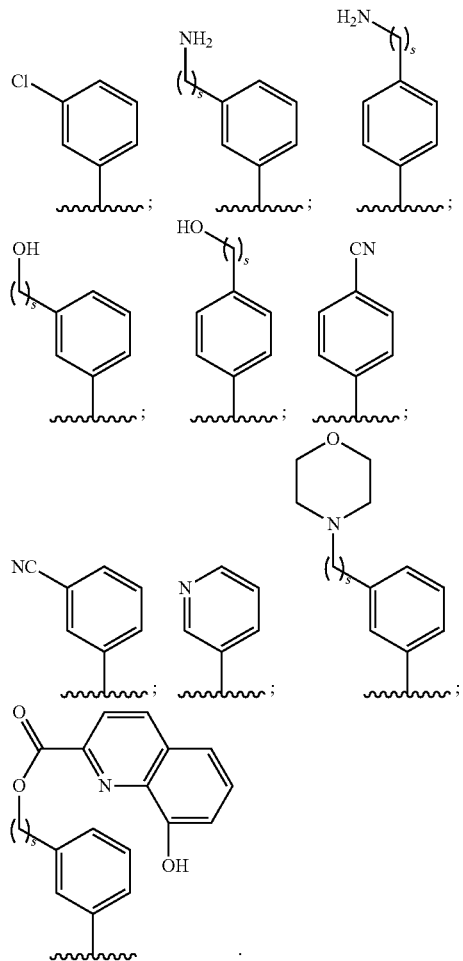

In another exemplary embodiment, there is a proviso that when M is Cl, R* is not a member selected from:

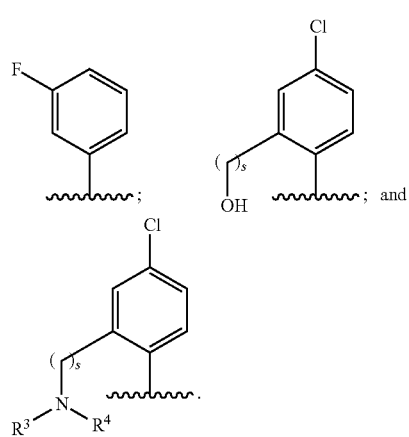

In another exemplary embodiment, there is a proviso that when M is H, R* is not a member selected from:

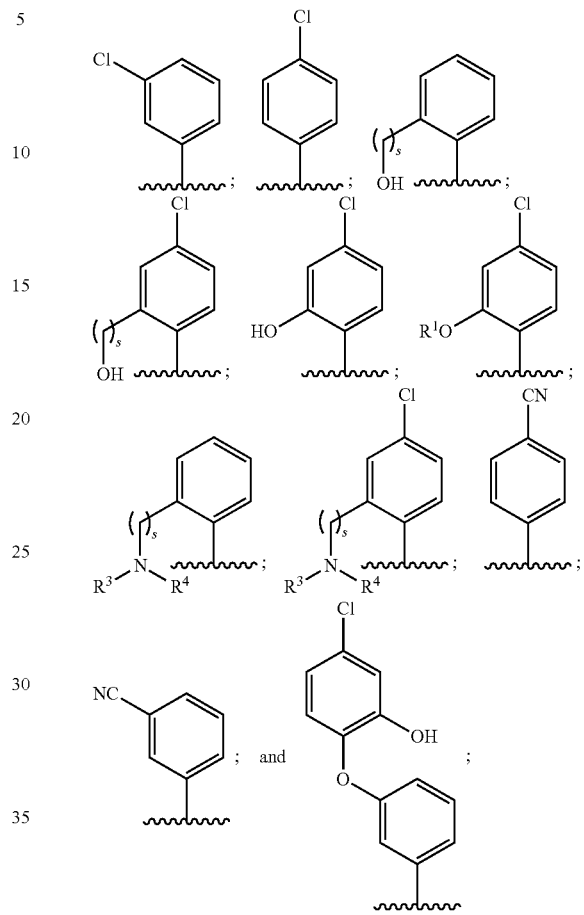

in which the index s is an integer selected from 1 and 2. $R^3$ and $R^4$ are members independently selected from methyl and ethyl.

In another exemplary embodiment, there is a proviso that when M is $OCH_3$, R* is not a member selected from:

Cl—⟨benzene⟩—.

In another exemplary embodiment, there is a proviso that when $M^1$ is F, R* is not a member selected from:

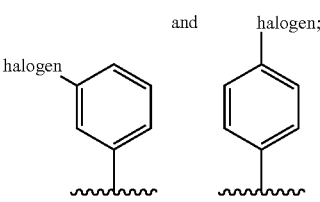

including salts thereof. This method comprises contacting the cell with a compound capable of penetrating the nail plate, under conditions sufficient to penetrate the nail. The compound has a molecular weight of between about 100 and about 200 Da. The compound also has a log P value of between about 1.0 and about 2.6. The compound additionally has a water solubility between about 0.1 mg/mL and 1 g/mL octanol/saturated water, thereby delivering said compound.

In a preferred embodiment, the physicochemical properties of the compound of the invention, described by quantities predictive for migration of the compound through the nail plate, including, but not limited to, molecular weight, log P and solubility in water, and the like, are effective to provide substantial penetration of the nail plate.

Compounds with a molecular weight of less than 200 Da penetrate the nail plate in a manner superior to the commercially available treatment for onychomycosis. In one embodiment of the present invention the compound has a molecular weight of between 130 and 200. In another embodiment of this invention, the compound has a molecular weight of from about 140 to about 200 Da. In another embodiment of this invention, the compound has a molecular weight of from about 170 to about 200 Da. In another embodiment of this invention, the compound has a molecular weight of from about 155 to about 190 Da. In another embodiment of this invention, the compound has a molecular weight of from about 165 to about 185 Da. In another embodiment of this invention, the compound has a molecular weight of from about 145 to about 170 Da. In yet another embodiment the molecular weight is either 151.93 or 168.39 Da.

In one embodiment of the present invention the compound has a Log P value of between about −3.5 to about 2.5. In another exemplary embodiment, the compound has a Log P value of from about −1.0 to about 2.5. In another exemplary embodiment, the compound has a Log P value of from about −1.0 to about 2.0. In another exemplary embodiment, the compound has a Log P value of from about −0.5 to about 2.5. In another exemplary embodiment, the compound has a Log P value of from about −0.5 to about 1.5. In another exemplary embodiment, the compound has a Log P value of from about 0.5 to about 2.5. In another exemplary embodiment, the compound has a Log P value of from about 1.0 to about 2.5. In yet another exemplary embodiment, the compound has a Log P value of 1.9 or 2.3.

Also contemplated by the present invention is a compound with a Log P value less then 2.5, with a molecular weight less than 200 Da, that are still able to penetrate the nail plate.

In one embodiment of the present invention the compound has a water solubility between about 0.1 mg/mL to 1 g/mL in octanol saturated water. In one embodiment of the present invention the compound has a water solubility of between 0.1 mg/mL and 100 mg/mL. In another embodiment of this invention, the compound has a water solubility of from about 0.1 mg/mL and 10 mg/mL. In another embodiment of this invention, the compound has a water solubility of from about 0.1 mg/mL and 1 mg/mL. In another embodiment of this invention, the compound has a water solubility of from about 5 mg/mL and 1 g/mL. In another embodiment of this invention, the compound has a water solubility of from about 10 mg/mL and 500 g/mL. In another embodiment of this invention, the compound has a water solubility of from about 80 mg/mL and 250 mg/mL.

In an exemplary embodiment, the present invention provides a compound with a Log P value selected from a range above, with a molecular weight selected from a range above, that are still able to penetrate the nail plate.

In an exemplary embodiment, the present invention provides compounds with a molecular weight selected from a range above, with a water solubility selected from a range above, that are still able to penetrate the nail plate.

In an exemplary embodiment, the present invention provides compounds with a log P selected from a range above, with a water solubility selected from a range above, that are still able to penetrate the nail plate.

In an exemplary embodiment, the present invention provides compounds with a molecular weight selected from a range above, with a log P selected from a range above, and with a water solubility selected from a range above, that are still able to penetrate the nail plate.

Penetration of the nail by the active ingredient may be effected by the polarity of the formulation. However, the polarity of the formulation is not expected have as much influence on nail penetration as some of the other factors, such as the molecular weight or the Log P of the active ingredient. The presence of penetration enhancing agents in the formulation is likely to increase penetration of the active agent when compared to similar formulations containing no penetration enhancing agent Some examples of molecules with optimal physicochemical properties are given in the table below.

| Structure: | 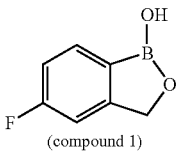 (compound 1) | 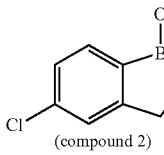 (compound 2) |
|---|---|---|
| Formula: | $C_7H_6BFO_2$ | $C_7H_6BClO_2$ |
| Molecular weight (Da): | 151.93 | 168.39 |
| Plasma protein binding (%): | 66 | 83 |
| LogP: | 1.9 | 2.3 |
| Water solubility (μg/mL): | >100 | >100 |

Compound 3 below is an example of a compound similar in molecular weight to ciclopirox, and like ciclopirox, penetrates the nail plate poorly.

| Structure: | 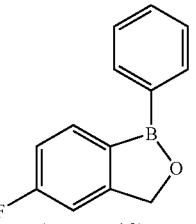 (compound 3) |
|---|---|
| Formula: | $C_{13}H_{10}BFO$ |
| Molecular weight (Da): | 212.03 |
| Plasma protein binding (%): | 100 |
| eLogP: | 3.55 |
| Water solubility (μg/mL): | not determined |

In a preferred embodiment the topical formulations including a compound described herein, such as according to Formulae (I), (II) and/or (III), has a total molecular weight of less than 200 Da, has a Log P of less than 2.5, and a minimum inhibitory concentration against *Trichophyton rubrum* that is substantially unchanged in the presence of 5% keratin.

This invention is still further directed to methods for treating a viral infection mediated at least in part by dermatophytes, *Trichophyton, Microsporum* or *Epidermophyton* species, or a yeast-like fungi including *Candida* species, in mammals, which methods comprise administering to a mammal, that has been diagnosed with said viral infection or is at risk of developing said viral infection, a pharmaceutical composition comprising a pharmaceutically acceptable diluent and a therapeutically effective amount of a compound described herein or mixtures of one or more of such compounds. In one embodiment the infection is onychomycosis.

Compounds contemplated by the present invention may have broad spectrum antifungal activity and as such may be candidates for use against other cutaneous fungal infections.

The methods provided in this aspect of the invention are useful in the penetration of nails and hoofs, as well as the treatment of ungual and periungual conditions.

Further discussion, and assays for testing log P, molecular weight and water solubility are described in U.S. patent application Ser. Nos. 11/357,687 and 11/505,591, which are incorporated herein by reference.

VI. Pharmaceutical Formulations

In another aspect, the invention is a pharmaceutical formulation which includes: (a) a pharmaceutically acceptable excipient; and (b) a compound described herein. In an exemplary embodiment, the compound has a structure according to Formulae (I), (II) and/or (III). In an exemplary embodiment, there is a proviso that when M is F, R* is not a member selected from:

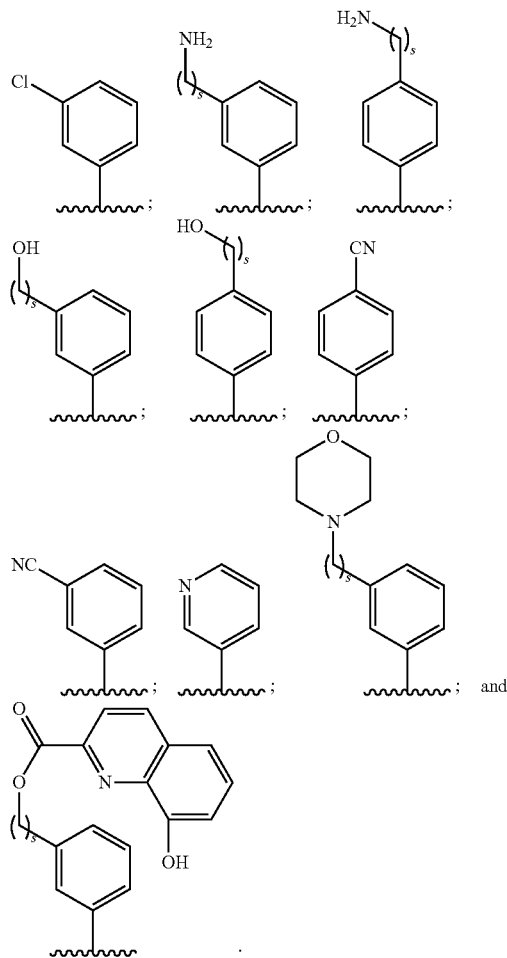

In another exemplary embodiment, there is a proviso that when M is Cl, R* is not a member selected from:

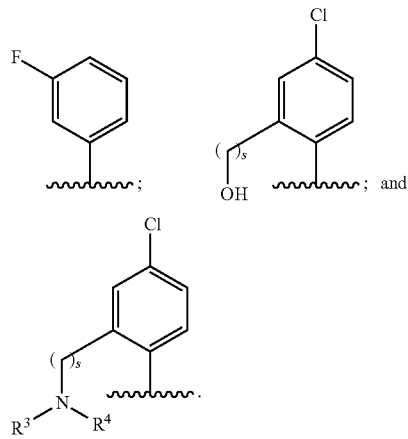

In another exemplary embodiment, there is a proviso that when M is H, R* is not a member selected from:

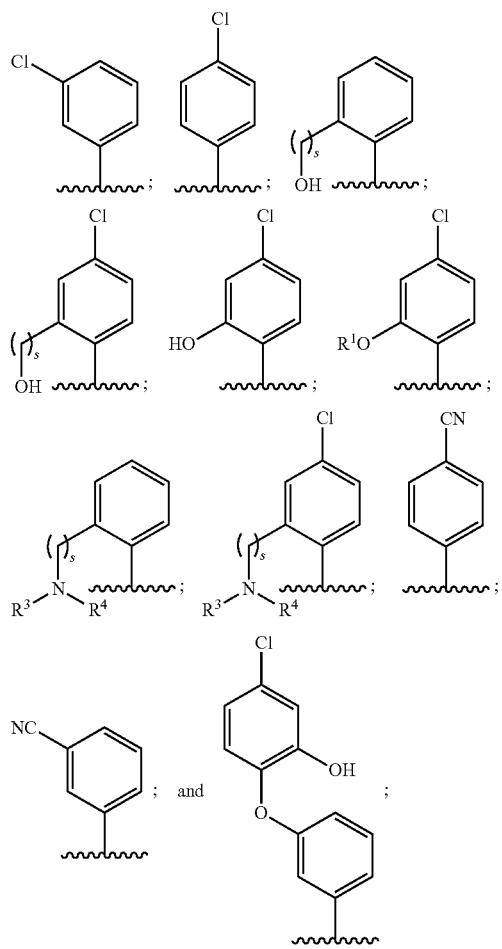

in which the index s is an integer selected from 1 and 2. $R^3$ and $R^4$ are members independently selected from methyl and ethyl.

In another exemplary embodiment, there is a proviso that when M is OCH₃, R* is not a member selected from:

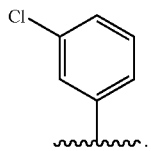

In another exemplary embodiment, there is a proviso that when M¹ is F, R* is not a member selected from:

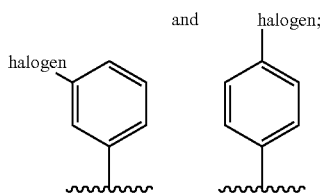

including salts thereof.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The compositions of the invention may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient. The compositions may contain from 0.1% to 99% by weight, preferably 10-60% by weight, of the active ingredient, depending on the method of administration.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al., *J. Chrom. B*, 677: 1-27 (1996).

Compound half-life is inversely proportional to the frequency of dosage of a compound. In vitro half-lives of compounds may be predicted from assays of microsomal half-life as described by Kuhnz and Gieschen, *Drug Metabolism and Disposition*, 26: 1120-1127 (1998).

The amount of the composition required for use in treatment will vary not only with the particular compound selected but also with the route of administration, the nature of the condition being treated and the age and condition of the patient and will ultimately be at the discretion of the attendant physician or clinician.

Exemplary procedures for delivering an antibacterial, antifungal and antimycoplasmal agent are described in U.S. Pat. No. 5,041,567, issued to Rogers et al. and in PCT patent application number EP94/02552 (WO 95/05384), the entire contents of which documents are incorporated in their entirety herein by reference. In general, the methods of the invention for delivering the inhibitors utilize art-recognized protocols for delivering the agent with the only substantial procedural modification being the substitution of the inhibitors, e.g., a compound described herein, such as a compound of Formulae (I), (II) and/or (III), for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of a compound described herein, such as a compound of Formulae (I), (II) and/or (III) for the agents used in the art-recognized protocols.

VI. a) Topical Formulations

In a preferred embodiment, the methods of the invention can be used employed through the topical application of the compounds described herein.

The compositions of the present invention comprises fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The solvent or mixed solvent system is important to the formation because it is primarily responsible for dissolving the drug. The best solvent or mixed solvent systems are also capable of maintaining clinically relevant levels of the drug in solution despite the addition of a poor solvent to the formulation. The topical compositions useful in the subject invention can be made into a wide variety of product types. These include, but are not limited to, lotions, creams, gels, sticks, sprays, ointments, pastes, foams, mousses, and cleansers. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in *Remington: The Science and Practice of Pharmacy*, supra. The formulation can be selected to maximize delivery to a desired target site in the body.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethyl-cellulose, or the like.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in *Remington: The Science and Practice of Pharmacy*, supra, is generally a nonionic, anionic, cationic or amphoteric surfactant.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in *Remington: The Science and Practice of Pharmacy*, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to *Remington: The Science and Practice of Pharmacy*, supra, for further information.

Useful formulations of the invention also encompass sprays. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

Preferred for use herein are high molecular weight alcohols such as cetearyl alcohol, cetyl alcohol, stearyl alcohol, emulsifying wax, glyceryl monostearate. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. More preferred for use herein are one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.; Spectrum Chemicals; and BASF. When the topical formulations of the present invention contain at least one emulsifying agent, each emulsifying agent is present in amount from about 0.5 to about 2.5 wt %, preferably 0.5 to 2.0%, more preferably 1.0% or 1.8%. Preferably the emulsifying agent comprises a mixture of steareth 21 (at about 1.8%) and steareth 2 (at about 1.0%).

The topical pharmaceutical compositions may also comprise suitable emollients. Emollients are materials used for the prevention or relief of dryness, as well as for the protection of the skin, nail, hair, claw or hoof. Useful emollients include, but are not limited to, cetyl alcohol, isopropyl myristate, stearyl alcohol, and the like. A wide variety of suitable emollients are known and can be used herein. See e.g., Sagarin, *Cosmetics, Science and Technology*, 2nd Edition, 1: 32-43 (1972), and Deckner et al., (U.S. Pat. No. 4,919,934, issued Apr. 24, 1990), both of which are incorporated herein by reference in their entirety. These materials are available from Ruger Chemical Co, (Irvington, N.J.).

When the topical formulations of the present invention contain at least one emollient, each emollient is present in an amount from about 0.1 to 15%, preferably 0.1 to about 3.0, more preferably 0.5, 1.0, or 2.5 wt %. Preferably the emollient is a mixture of cetyl alcohol, isopropyl myristate and stearyl alcohol in a 1/5/2 ratio. The emollient may also be a mixture of cetyl alcohol and stearyl alcohol in a 1/2 ratio.

According to this aspect of the invention, the editing domain inhibitors are placed in a pharmaceutically-acceptable carrier and are delivered to a recipient subject (preferably a human) in accordance with known methods of drug delivery. Exemplary procedures for delivering an antibacterial, antifungal and antimycoplasmal agent are described in U.S. Pat. No. 5,041,567, issued to Rogers et al. and in PCT patent application number EP94/02552 (WO 95/05384), the entire contents of which documents are incorporated in their entirety herein by reference. In general, the methods of the invention for delivering the inhibitors utilize art-recognized protocols for delivering the agent with the only substantial procedural modification being the substitution of the inhibitors, e.g., a compound described herein, such as a compound of Formulae (I), (II) and/or (III), for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of a compound described herein, such as a compound of Formulae (I), (II) and/or (III), for the agents used in the art-recognized protocols.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.).

When the topical formulations of the present invention contain at least one antioxidant, the total amount of antioxidant present is from about 0.001 to 0.5 wt %, preferably 0.05 to about 0.5 wt %, more preferably 0.1%.

The topical pharmaceutical compositions may also comprise suitable preservatives. Preservatives are compounds added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., *Develop. Biol Standard*, 24:9-28 (1974) (S. Krager, Basel). Preferably, the preservative is selected from methylparaben, propylparaben and mixtures thereof. These materials are available from Inolex Chemical Co (Philadelphia, Pa.) or Spectrum Chemicals.

When the topical formulations of the present invention contain at least one preservative, the total amount of preservative present is from about 0.01 to about 0.5 wt %, preferably from about 0.1 to 0.5%, more preferably from about 0.03 to about 0.15. Preferably the preservative is a mixture of methylparaben and proplybarben in a 5/1 ratio. When alcohol is used as a preservative, the amount is usually 15 to 20%.

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N', N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid. These materials are available from Spectrum Chemicals.

When the topical formulations of the present invention contain at least one chelating agent, the total amount of chelating agent present is from about 0.005% to 2.0% by weight, preferably from about 0.05% to about 0.5 wt %, more preferably about 0.1% by weight.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid. Such materials are available from are available from Spectrum Chemicals (Gardena, Calif.).

When the topical formulations of the present invention contain at least one neutralizing agent, the total amount of neutralizing agent present is from about 0.1 wt to about 10 wt %, preferably 0.1 wt % to about 5.0 wt %, and more preferably about 1.0 wt %. The neutralizing agent is generally added in whatever amount is required to bring the formulation to the desired pH.

The topical pharmaceutical compositions may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Noveon Chemicals, Cleveland, Ohio.

When the topical formulations of the present invention contain at least one viscosity increasing agent, the total amount of viscosity increasing agent present is from about 0.25% to about 5.0% by weight, preferably from about 0.25% to about 1.0 wt %, and more preferably from about 0.4% to about 0.6% by weight.

The topical pharmaceutical compositions may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., *J. Pharm. Sci.*, 91:2, 312-323 (2002), which is incorporated herein by reference in its entirety.

The topical pharmaceutical compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into topical formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some compounds in the invention in water is less than 0.00025% wt/wt. The solubility of the same compounds in the invention can be less than about 2% wt/wt in either propylene glycol or isopropyl myristate. In one embodiment of the present invention, diethylene glycol monoethyl ether (DGME) is the solvent used to dissolve the compounds of Formulae (I), (II) and/or (III). The compounds in the invention useful in the present formulation are believed to have a solubility of from about 10% wt/wt to about 25% wt/wt in DGME. In another embodiment a DGME water cosolvent system is used to dissolve the compounds described herein, such as the compounds of Formulae (I), (II) and/or (III). The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt, in the as-applied topical formulations. Because DGME is less volatile than water, as the topical formulation evaporates upon application, the active agent becomes more soluble in the cream formulation. This increased solubility reduces the likelihood of reduced bioavailability caused by the drug precipitating on the surface of the skin, nail, hair, claw or hoof.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Additionally, the compounds can be delivered using a sustained-release system, such as semipermeable matrices of solid hydrophobic polymers containing the therapeutic agent. Various sustained-release materials have been established and are well known by those skilled in the art.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the pharmaceutical formulation includes a simple solution. In an exemplary embodiment, the simple solution includes an alcohol. In an exemplary embodiment, the simple solution includes alcohol and water. In an exemplary embodiment, the alcohol is ethanol, ethylene glycol, propanol, polypropylene glycol, isopropanol or butanol. In another exemplary embodiment, the simple solution is a member selected from about 10% polypropylene glycol and about 90% ethanol; about 20% polypropylene glycol and about 80% ethanol; about 30% polypropylene glycol and about 70% ethanol; about 40% polypropylene glycol and about 60% ethanol; about 50% polypropylene glycol and about 50% ethanol; about 60% polypropylene glycol and about 40% ethanol; about 70% polypropylene glycol and about 30% ethanol; about 80% polypropylene glycol and about 20% ethanol; about 90% polypropylene glycol and about 10% ethanol.

In an exemplary embodiment, the pharmaceutical formulation is a lacquer. Please see *Remington's*, supra, for more information on the production of lacquers.

In an exemplary embodiment, the compound is present in said pharmaceutical formulation in a concentration of from about 0.5% to about 15%. In an exemplary embodiment, the compound is present in said pharmaceutical formulation in a concentration of from about 0.1% to about 12.5%. In an exemplary embodiment, the compound is present in said pharmaceutical formulation in a concentration of from about 1% to about 10%. In an exemplary embodiment, the compound is present in said pharmaceutical formulation in a concentration of from about 1% to about 5%. In an exemplary embodiment, the compound is present in said pharmaceutical formulation in a concentration of from about 2% to about 8%. In an exemplary embodiment, the compound is present in said pharmaceutical formulation in a concentration of from about 4% to about 9%.

VI. b) Additional Active Agents

The following are examples of the cosmetic and pharmaceutical agents that can be added to the topical pharmaceutical formulations of the present invention. The following agents are known compounds and are readily available commercially.

Anti-inflammatory agents include, but are not limited to, bisabolol, mentholatum, dapsone, aloe, hydrocortisone, and the like.

Vitamins include, but are not limited to, Vitamin B, Vitamin E, Vitamin A, Vitamin D, and the like and vitamin derivatives such as tazarotene, calcipotriene, tretinoin, adapalene and the like.

Anti-aging agents include, but are not limited to, niacinamide, retinol and retinoid derivatives, AHA, Ascorbic acid, lipoic acid, coenzyme Q 10, beta hydroxy acids, salicylic acid, copper binding peptides, dimethylaminoethyl (DAEA), and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA).

Psoriasis-treating agents and/or acne-treating agents include, but are not limited to, salicylic acid, benzoyl peroxide, coal tar, selenium sulfide, zinc oxide, pyrithione (zinc and/or sodium), tazarotene, calcipotriene, tretinoin, adapalene and the like.

Agents that are effective to control or modify keratinization, including without limitation: tretinoin, tazarotene, and adapalene.

The compositions comprising a compound/active agent described herein, such as those of Formulae (I), (II) and/or (III), and optionally at least one of these additional agents, are to be administered topically. In a primary application, this leads to the compounds of the invention and any other active agent working upon and treating the skin, nail, hair, claw or hoof. Alternatively, any one of the topically applied active agents may also be delivered systemically by transdermal routes.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or preferably from about 0.01% to about 10% by weight) with the remainder being various vehicles or carriers and processing aids helpful for forming the desired dosing form.

VI. c) Testing

Preferred compounds for use in the present topical formulations will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (*J. Chromat.* B 677: 1-27 (1996)). Compound half-life is inversely proportional to the frequency of dosage of a compound. In vitro half-lives of compounds may be predicted from assays of microsomal half-life as described by Kuhnz and Gleschen (*Drug Metabolism and Disposition,* 26:1120-1127 (1998)).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. d) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain bacterial cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

The invention is further illustrated by the Examples that follow. The Examples are not intended to define or limit the scope of the invention.

EXAMPLES

General: Melting points were obtained using a MeI-Temp-II melting point apparatus and are uncorrected. $^1$H NMR spectra were recorded on Oxford 300 (300 MHz) spectrometer (Varian). Mass spectra were determined on API 3000 (Applied Biosystems). Purity by HPLC (relative area) was determined using ProStar Model 330 (PDA detector, Varian), Model 210 (pump, Varian), and a BetaBasic-18 4.6×150 mm column (Thermo Electron Corporation) with a linear gradient of 0 to 100% MeCN in 0.01% $H_3PO_4$ over 10 min followed by 100% MeCN for another 10 min at 220 nm.

Example 1

Precursors to CBOs and CBEs

1.1 2-Bromo-5-fluoro-[1-(methoxymethoxy)methyl]benzene (5b)

To a solution of 3 (62.0 g, 293 mmol) in MeOH (400 mL) was added $NaBH_4$ (5.57 g, 147 mmol) portionwise at 0° C., and the mixture was stirred at room temperature for 1 h. Water was added, and the solvent was removed under reduced pressure to about a half volume. The mixture was poured into EtOAc and water. The organic layer was washed with brine and dried over anhydrous $Na_2SO_4$. The solvent was removed under reduced pressure to afford 4b, which was used for the next step without purification. To a solution of 4b (60.8 g, 293 mmol) and i-$Pr_2NEt$ (61 mL, 0.35 mol) in $CH_2Cl_2$ was added chloromethyl methyl ether (27 mL, 0.35 mmol) at 0° C., and the mixture was stirred at room temperature overnight. Water was added, and the mixture was extracted with $CHCl_3$. The organic layer was washed with brine and dried over anhydrous $Na_2SO_4$. The solvent was removed under reduced pressure to afford 5b (73.2 g, quant). $^1$H NMR (300 MHz, $CDCl_3$) δ (ppm) 3.43 (s, 3H), 4.62 (s, 2H), 4.78 (s, 2H), 6.88 (td, J=8.5, 3.2 Hz, 1H), 7.25 (dd, J=9.6, 3.1 Hz, 1H), 7.48 (dd, J=8.8, 5.3 Hz, 1H).

1.2 2-Bromo-[1-(methoxymethoxy)methyl]benzene (5a)

This compound was made from 2-bromobenzylalcohol in the same manner as compound 5b and used for the next step without purification.

1.3 2-[4-Fluoro-2-[(methoxymethoxy)methyl]phenyl]-[1,3,2]dioxaborolane (6)

To a solution of 5b (16.2 g, 65.1 mmol) in THF (130 mL) were added sec-BuLi (1.4 M, 56 mL) and $(MeO)_3B$ (14.5 mL, 130 mmol) at −78° C. under nitrogen atmosphere, and the mixture was allowed to warm to room temperature and stirred for 2 h. Water and 1 N NaOH were added to the mixture, which was washed with $Et_2O$. Then the pH was adjusted to 4 with 1 N HCl, and the mixture was extracted with EtOAc. The organic layer was washed with brine and dried over anhydrous $Na_2SO_4$. Then the solvent was removed under reduced pressure to give boronic acid, which was used for the next step without purification. To a solution of the boronic acid in toluene (300 mL) was added ethylene glycol (3.29 g, 53 mmol), and the mixture was refluxed for 3 h with a Dean-Stark trap. The solvent was removed under reduced pressure to afford 6 (12.1 g, 77%). $^1$H-NMR (300 MHz, $CDCl_3$) δ (ppm) 3.42 (s, 3H), 4.36 (s, 4H), 4.76 (s, 2H), 4.87 (s, 2H), 6.96 (td, J=8.2, 2.6 Hz, 1H), 7.26 (dd, J=10.6, 2.6 Hz, 1H), 7.83 (dd, J=8.2, 6.4 Hz, 1H).

1.4 2-(3-Chlorophenyl)[1,3,2]dioxaborolane (7b; $R^{iii}$=3-Cl-Ph)

3-Chlorophenylboronic acid (3.041 g, 19.4 mmol) was dissolved in 75 mL of dry THF under nitrogen atmosphere. Ethylene glycol (1.32 g, 21.3 mmol) was added and the solution was refluxed for 18 h. The solution was allowed to cool and the THF was removed under reduced pressure to give 7b (3.55 g, 100%) as a brown oil that solidified upon cooling in the freezer. $^1$H NMR (300 MHz, $CDCl_3$) δ (ppm) 4.39 (s, 4H), 7.32 (t, J=7.9 Hz, 1H), 7.45 (dd, J=8.2, 1.2 Hz, 1H), 7.67 (d, J=7.0 Hz, 1H), 7.78 (br s, 1H).

Compounds 7a and 7c-k were synthesized in a similar manner to 7b.

1.5 2-Phenyl[1,3,2]dioxaborolane (7a; $R^{iii}$=Ph)

$^1$H NMR (300 MHz, DMSO-$d_6$) δ (ppm) 4.30 (s, 4H), 7.35-7.41 (t, J=8.2 Hz, 2H), 7.46-7.52 (m, 1H), 7.68-7.72 (dd, J=6.2, 2.6 Hz, 2H).

1.6 2-(4-Chlorophenyl) [1,3,2]dioxaborolane (7c; $R^{iii}$=4-Cl-Ph)

$^1$H NMR (300 MHz, $CDCl_3$) δ (ppm) 4.38 (s, 4H), 7.36 (d, J=6.7 Hz, 2H), 7.74 (d, J=7.0 Hz, 2H).

1.7 2-(3-Fluorophenyl)[1,3,2]dioxaborolane (7d; $R^{iii}$=3-F-Ph)

$^1$H NMR (300 MHz, $CDCl_3$) δ (ppm) 4.39 (s, 4H), 7.1-7.2 (m, 1H), 7.36 (td, J=8.2, 5.6 Hz, 1H), 7.48 (dd, J=9.1, 2.6 Hz, 1H), 7.58 (d, J=7.0 Hz, 1H).

1.8 2-(4-Fluorophenyl) [1,3,2]dioxaborolane (7e; $R^{iii}$=4-F-Ph)

$^1$H NMR (300 MHz, DMSO-$d_6$) δ (ppm) 4.29 (s, 4H), 7.17-7.23 (t, J=8.5 Hz, 2H), 7.71-7.76 (dd, J=8.5, 6.1 Hz, 2H).

1.9 2-(3-Methylphenyl)[1,3,2]dioxaborolane (7f; $R^{iii}$=3-Me-Ph)

$^1$H NMR (300 MHz, DMSO-$d_6$) δ (ppm) 2.31 (s, 3H), 4.31 (s, 4H), 7.29-7.32 (m, 2H), 7.50-7.53 (m, 2H).

1.10 2-Styryl[1,3,2]dioxaborolane (7h; $R^{iii}$=styryl)

$^1$H NMR (300 MHz, DMSO-$d_6$) δ (ppm) 4.20 (s, 4H), 6.15 (d, J=18.5 Hz, 1H), 7.31-7.39 (m, 4H), 7.56 (dd, J=1.5, 7.6 Hz, 2H).

1.11 2-(Thiophen-3-yl) [1,3,2]dioxaborolane (7j; $R^{iii}$=thiophen-3-yl)

$^1$H NMR (300 MHz, DMSO-$d_6$) δ (ppm) 4.27 (s, 4H), 7.30 (dd, J=4.8, 0.9 Hz, 1H), 7.58 (dd, J=4.5, 2.4 Hz, 1H), 8.03 (dd, J=2.7, 1.2 Hz, 1H).

1.12 2-(4-Methylthiophen-3-yl)[1,3,2]dioxaborolane (7k; $R^{iii}$=4-methylthiophen-3-yl)

$^1$H NMR (300 MHz, DMSO-$d_6$) δ (ppm) 2.31 (s, 3H), 4.25 (s, 4H), 7.13-7.14 (m, 1H), 7.93 (d, J=3.0 Hz, 1H).

Example 2

CBEs

2.1 1-(3-Chlorophenyl)-1,3-dihydro-5-fluoro-2,1-benzoxaborole (9f)

Compound 5b (1.06 g, 4.20 mmol) was dissolved in 50 mL of dry THF under nitrogen atmosphere and cooled to −78° C. tert-BuLi (1.7M in pentane, 5.3 mL) was slowly added to the solution. After stirring for 10 minutes at −78° C., compound 7b (764 mg, 4.20 mmol) in 10 mL of dry THF was added and the solution was stirred for further 0.5 h. The solution was then allowed to warm to room temperature and stirred for 18 h. The solvent was removed under reduced pressure, and the residue was partitioned between 40 ml of $H_2O$ and 80 mL of diethyl ether. The solution was vigorously stirred for several minutes then neutralized (pH 7) with 6 N HCl. The organic layer was separated and the aqueous solution extracted again with ether (2×80 mL). The ether extracts were combined, dried over $MgSO_4$, filtered and evaporated to give crude 8f (1.22 g) as a yellow oil, which was used for the next step without purification. Compound 8f (700 mg, 2.30 mmol) was dissolved in 46 mL of THF and 4 mL of concentrated HCl. The solution was stirred at room temperature for 12 h. Water (10 mL) was then added and the THF was removed under reduced pressure. This gave a suspension. The precipitates were filtered under vacuum and washed with water (10 mL) then with hexanes (5 mL) and dried to give compound 9f (334 mg, 59%) as a white solid: mp 112-114° C.; $^1$H NMR (300 MHz, DMSO-$d_6$) δ (ppm) 5.15 (s, 2H), 7.02-7.08 (t, J=8.8 Hz, 1H), 7.14-7.17 (d, J=8.8 Hz, 1H), 7.23-7.33 (m, 2H), 7.65-7.72 (m, 3H); ESI-MS m/z 247.08, 249.03 (M−H)$^−$; HPLC purity: 97.1%; Anal. ($C_{13}H_9ClFO$)C, H.

Compounds 9a-e, 9g-j, 10a,b, and 12-15 were synthesized in a similar manner to 9f.

2.1 1,3-Dihydro-1-phenyl-2,1-benzoxaborole (9a)

Colorless oil; $^1$H NMR (300 MHz, DMSO-$d_6$) δ (ppm) 5.41 (s,2H), 7.43-7.61 (m, 6H), 8.11 (d, J=9.4 Hz, 2H), 8.18 (d, J=8.2 Hz, 1H); ESI-MS m/z not observed; HPLC purity: 95.5%.

2.2 1,3-Dihydro-5-fluoro-1-phenyl-2,1-benzoxaborole (9b)

mp 90-99° C.; $^1$H NMR (300 MHz, DMSO-$d_6$) δ (ppm) 5.37 (s,2H), 7.22 (dt, J=2.3, 8.9 Hz, 1H), 7.38 (dd, J=2.1, 9.4 Hz, 1H), 7.45-7.57 (m, 3H), 8.06 (dd, J=1.8, 7.9 Hz, 2H), 8.16 (dd, J=5.9, 8.2 Hz, 1H); ESI-MS m/z 213 (M+H)$^+$; HPLC purity: 95.1%.

2.3 1-(3-Chlorophenyl)-1,3-dihydro-2,1-benzoxaborole (9c)

colorless oil; $^1$H NMR (300 MHz, DMSO-$d_6$) δ (ppm) 5.26 (s, 2H), 7.29-7.45 (m, 5H), 7.77-7.86 (m, 3H); ESI-MS m/z Not observed; HPLC purity: 96.0%; Anal ($C_{13}H_{10}BClO$) C, H.

2.4 1,3-Dihydro-1-(3-fluorophenyl)-2,1-benzoxaborole (9d)

colorless oil; $^1$H NMR (300 MHz, DMSO-$d_6$) δ (ppm) 5.28 (s, 2H), 7.23 (m, 1H), 7.34 (m, 1H), 7.41-7.48 (m, 3H), 7.57-7.61 (dd, J=9.6, 2.6 Hz, 1H), 7.74-7.77 (d, J=7.3 Hz, 1H), 7.93-7.95 (d, J=7.3 Hz, 1H); ESI-MS m/z Not observed; HPLC purity: 98.3%; Anal ($C_{13}H_{10}BFO$)C, H.

2.5 1,3-Dihydro-1-(4-fluorophenyl)-2,1-benzoxaborole (9e)

mp 53-55° C.; $^1$H NMR (300 MHz, DMSO-$d_6$) δ (ppm) 5.37 (s, 2H), 7.26-7.32 (m, 2H), 7.42 (m, 1H), 7.53-7.55 (m, 2H), 8.11-8.16 (m, 3H); ESI-MS m/z not observed; HPLC purity: 99.3%; Anal. ($C_{13}H_{10}BFO$)C, H.

2.6 1,3-Dihydro-5-fluoro-1-(3-fluorophenyl)-2,1-benzoxaborole (9g)

mp 80-82° C.; $^1$H NMR (300 MHz, DMSO-$d_6$) δ (ppm) 5.20 (s, 2H), 7.06-7.18 (m, 2H), 7.22 (dd, J=9.6, 1.8 Hz, 1H), 7.39 (td, J=7.8, 5.4 Hz, 1H), 7.49 (dd, J=9.9, 2.7 Hz, 1H), 7.63 (dd, J=6.9, 0.9 Hz, 1H), 7.83 (dd, J=8.1, 5.7 Hz, 1H); ESI-MS m/z not observed; HPLC purity: 98.5%; Anal. ($C_{13}H_9BF_2O$) C, H.

2.7 1,3-Dihydro-5-fluoro-1-(4-fluorophenyl)-2,1-benzoxaborole (9h)

mp 75-77° C.; $^1$H NMR (300 MHz, DMSO-$d_6$) δ (ppm) 5.33 (s, 2H), 7.19-7.30 (m, 3H), 7.36 (dd, J=9.9, 2.1 Hz, 1H), 8.05-8.14 (m, 3H).; ESI-MS m/z not observed; HPLC purity: 99.0%; Anal. ($C_{13}H_9BF_2O$)C, H.

2.8 1,3-Dihydro-5-fluoro-1-(3-methylphenyl)-2,1-benzoxaborole (9l)

mp 48-49° C.; $^1$H NMR (300 MHz, DMSO-$d_6$) δ (ppm) 2.37 (s, 3H), 5.36 (s, 2H), 7.25 (m, 1H), 7.3-7.5 (m, 3H), 7.8-7.9 (m, 2H), 8.20 (dd, J=7.9, 5.9 Hz, 1H); ESI-MS m/z 227 (M+H)$^+$; HPLC purity: 99.8%; Anal. ($C_{14}H_{12}BFO$)C, H.

2.9 1,3-Dihydro-5-fluoro-1-(4-methylphenyl)-2,1-benzoxaborole (9j)

mp 48-49° C.; $^1$H NMR (300 MHz, DMSO-$d_6$) δ (ppm) 2.36 (s, 3H), 5.35 (s, 2H), 7.25 (m, 1H), 7.29 (d, J=7.6 Hz, 2H), 7.40 (dd, J=9.4, 1.5 Hz, 1H), 7.99 (d, J=7.6 Hz, 2H), 8.20 (dd, J=7.9, 5.6 Hz, 1H); ESI-MS m/z 227 (M+H)$^+$; HPLC purity: 98.9%; Anal. ($C_{14}H_{12}BFO$)C, H.

2.10 1,3-Dihydro-1-styryl-2,1-benzoxaborole (10a)

mp 57-59° C.; $^1$H NMR (300 MHz, DMSO-$d_6$) δ (ppm) 5.33 (s,2H), 6.85 (d, J=18.8 Hz, 1H), 7.38-7.46 (m, 4H), 7.56 (d, J=4.7 Hz, 2H), 7.64 (d, J=7.9 Hz, 2H), 7.83 (d, J=18.8 Hz, 1H), 8.14 (d, J=7.3 Hz, 1H); ESI-MS m/z 221 (M+H)$^+$; HPLC purity: 98.5%; Anal. ($C_{13}H_{10}BFO$ $0.1H_2O$)C, H.

2.11 1,3-Dihydro-5-fluoro-1-styryl-2,1-benzoxaborole (10b)

mp 84-86° C.; $^1$H NMR (300 MHz, DMSO-$d_6$) δ (ppm) 5.32 (s,2H), 6.86 (d, J=18.8 Hz, 1H), 7.24 (td, J=2.3, 10.6 Hz, 1H), 7.38-7.47 (m, 4H), 7.74 (d, J=7.0 Hz, 2H), 7.83 (d, J=18.8 Hz, 1H), 8.19 (dd, J=5.9, 8.2 Hz, 1H); ESI-MS m/z 239 (M+H)$^+$; HPLC purity: 99.1%; Anal. ($C_{13}H_{10}BFO$)C, H.

2.12 1,3-Dihydro-5-fluoro-1-(furan-3-yl)-2,1-benzoxaborole (12)

colorless oil; $^1$H NMR (300 MHz, DMSO-$d_6$) δ (ppm) 5.34 (s, 2H), 6.84 (m, 1H), 7.24 (m, 1H), 7.37-7.40 (d, J=9.4 Hz, 1H), 7.83 (m, 1H), 8.14-8.18 (dd, J=8.2, 5.9 Hz, 1H), 8.49 (m, 1H); ESI-MS m/z 203 (M+H)$^+$; HPLC purity: 96.9%; Anal. ($C_{11}H_8BFO_2$) C, H.

2.13 1,3-Dihydro-5-fluoro-1-(thiophen-3-yl)-2,1-benzoxaborole (13)

mp 33-35° C.; $^1$H NMR (300 MHz, DMSO-$d_6$) δ (ppm) 5.33 (s, 2H), 7.24 (m, 1H), 7.35-7.38 (d, J=9.3 Hz, 1H), 7.65

(m, 2H), 8.17-8.22 (dd, J=8.4, 6.3 Hz, 1H), 8.48 (m, 1H); ESI-MS m/z 219 (M+H)$^+$; HPLC purity: 97.8%; Anal. ($C_{11}H_8BFOS$)C, H.

2.14 1,3-Dihydro-5-fluoro-1-(4-methylthiophen-3-yl)-2,1-benzoxaborole (14)

mp 51-53° C.; $^1$H NMR (300 MHz, DMSO-d$_6$) δ (ppm) 2.46 (s, 3H), 5.36 (s, 2H), 7.20-7.27 (m, 2H), 7.37-7.40 (dd, J=9.4, 2.1 Hz, 1H), 8.14-8.19 (dd, J=8.2, 5.9 Hz, 1H), 8.48-8.49 (d, J=2.6 Hz, 1H); ESI-MS m/z 233 (M+H)$^+$; HPLC purity: 100%; Anal. ($C_{12}H_{10}BFOS$)C, H.

2.15 1,3-Dihydro-5-fluoro-1-vinyl-2,1-benzoxaborole (11)

Compound 5b (2.0 g, 8.0 mmol) in THF (30 mL) was cooled to −78° C. and tert-butyllithium (9.9 mL, 16.8 mmol) as 1.7 M solution in pentane was added slowly. After stirring at −78° C. for 30 min, dibutyl ester of vinyl boronic acid was added dropwise. The mixture was stirred at −78° C. for 1 h, then was warmed up to room temperature and stirred overnight. Concentrated HCl (4 mL) was added and was stirred at room temperature for 4 h. Water (10 mL) was added and THF was removed under reduced pressure. The residue was extracted with ethyl ether, washed with brine, dried over magnesium sulfate, and concentrated under reduced pressure. The crude product was purified by flash column chromatography (9:1 hexane/ethyl acetate) to give 11 (383 mg, 30%) as a yellowish oil; $^1$H NMR (300 MHz, DMSO-d$_6$) δ (ppm) 5.27 (s, 2H), 6.25 (t, J=8.5 Hz, 1H), 6.50 (d, J=9.4 Hz, 2H), 7.06-7.15 (m, 2H), 7.89 (dd, J=5.6, 7.9 Hz, 1H); ESI-MS m/z (M+H)$^+$; HPLC purity: 98.7%; Anal. ($C_9H_8BFO$ 0.1H$_2$O)C, H.

2.16 3-(1,3-Dihydro-5-fluoro-2,1-benzoxaborol-1-yl) pyridine (15)

To a solution of 3-bromopyridine (731 mg, 4.63 mmol) in THF (5 mL) was added isopropylmagnesium chloride (1 M in THF; 2.3 mL) at room temperature under nitrogen atmosphere, and the mixture was stirred for 1 h. To the mixture was added compound 6 (1.11 g, 4.63 mmol) in THF (4 mL), and the mixture was stirred at room temperature overnight. Water was added and the pH was adjusted to 7 with 1 N HCl. Then the mixture was extracted with ethyl acetate. The solvent was removed under reduced pressure, and the residue was dissolved in THF (30 mL). To the mixture was added 1 N HCl (10 mL), and the mixture was refluxed overnight. The pH was adjusted to 7 with aqueous NaHCO$_3$ and the mixture was extracted with ethyl acetate. The organic layer was washed with brine and dried over anhydrous Na$_2$SO$_4$. The solvent was removed under reduced pressure and the residue was recrystallized from i-Pr$_2$O to afford compound 15 (76 mg, 7.7%): mp 210-212° C.; $^1$H NMR (300 MHz, DMSO-d$_6$) δ 4.94 (s, 2H), 6.9-7.1 (m, 2H), 7.36 (br s, 1H), 7.66 (dd, J=6.7, 5.3 Hz, 1H), 8.19 (d, J=6.7 Hz, 1H), 8.24 (br s, 1H), 8.64 (d, J=5.3 Hz, 1H): ESI-MS m/z 214 (M+H)$^+$; Anal ($C_{12}H_9BFNO.0.6H_2O$)C, H, N.

Example 3

Precursors for CBOs

3.1 2-Bromo-5-fluoro-[1-(methoxymethoxy)ethyl]benzene (18c)

To a solution of compound 3 (4.23 g, 20.0 mmol) in THF (30 mL) was added MeMgBr (1.4 mol/L in THF; 18 mL) at −78° C. under nitrogen atmosphere, and the mixture was stirred for 2 h while allowing to warm to room temperature. The reaction was quenched with 2 N HCl, and the mixture was extracted with EtOAc. The organic layer was washed with brine and dried over anhydrous Na$_2$SO$_4$. The solvent was removed under reduced pressure. To a solution of the residue (4.62 g) in CH$_2$Cl$_2$ (100 mL) were added i-Pr$_2$NEt (5.2 mL, 30 mmol) and chloromethyl methyl ether (2.0 mL, 26 mmol) at 0° C., and the reaction mixture was stirred at room temperature overnight. Water was added, and the mixture was extracted with CHCl$_3$. The organic layer was washed with brine and dried over anhydrous Na$_2$SO$_4$. The solvent was removed under reduced pressure. The residue was purified by silica gel column chromatography (15:1 hexane/ethyl acetate) to give 18c (4.97 g, 2 steps 94%): $^1$H NMR (300 MHz, CDCl$_3$) δ (ppm) 1.43 (d, J=6.5 Hz, 3H), 3.38 (s, 3H), 4.55 (d, J=6.5 Hz, 1H), 4.63 (d, J=6.5 Hz, 1H), 5.07 (q, J=6.5 Hz, 1H), 6.85 (m, 1H), 7.25 (dd, J=9.7, 2.6 Hz, 1H), 7.46 (dd, J=8.8, 5.3 Hz, 1H).

3.2 2-Bromo-5-chloro-1-(methoxymethoxymethyl)benzene (18d)

To a solution of 2-bromo-5-chlorobenzoic acid (5.49 g, 23.3 mmol) in anhydrous THF (70 mL) under nitrogen was added dropwise a BH$_3$ THF solution (1.0 M, 55 mL) at 0° C. and the reaction mixture was stirred overnight at room temperature. Then the mixture was cooled on an ice bath and MeOH (20 mL) was added dropwise to decompose excess BH$_3$. The resulting mixture was stirred until no bubble was released and then 10% NaOH (10 mL) was added. The mixture was concentrated and the residue was mixed with water (200 mL) and extracted with EtOAc. The residue from rotary evaporation was purified by silica gel column chromatography (5:1 hexane/EtOAc) to give 2-bromo-5-chlorobenzyl alcohol as a white solid (4.58 g, 88%): $^1$H NMR (300 MHz, DMSO-d$_6$): δ (ppm) 7.57 (d, J=8.7 Hz, 1H), 7.50-7.49 (m, 1H), 7.28-7.24 (m, 1H), 5.59 (t, J=6.0 Hz, 1H), 4.46 (d, J=6.0 Hz, 2H).

2-Bromo-5-chlorobenzyl alcohol obtained above was dissolved in CH$_2$Cl$_2$ (150 mL) and cooled to 0° C. on an ice bath. To this solution under nitrogen were added in sequence i-Pr$_2$NEt (5.4 mL, 31 mmol) and chloromethyl methyl ether (2.0 mL, 26 mmol). The reaction mixture was stirred overnight at room temperature and washed with NaHCO$_3$-saturated water and then brine. The residue after rotary evaporation was purified by silica gel column chromatography (5:1 hexane/EtOAc) to give 18d (4.67 g, 85%) as a colorless oil: $^1$H NMR (300 MHz, DMSO-d$_6$): δ (ppm) 3.30 (s, 3H), 4.53 (s, 2H), 4.71 (s, 2H), 7.32 (dd, J=8.4, 2.4 Hz, 1H), 7.50 (dd, J=2.4, 0.6 Hz, 1H), 7.63 (d, J=8.7 Hz, 1H).

3.3 4-Bromo-3-(methoxymethoxymethyl)toluene (18e)

This compound was made from 2-bromo-5-methylbenzoic acid in the same manner as compound 18d: $^1$H NMR (300

MHz, DMSO-$d_6$) δ (ppm) 2.27 (s, 3H), 3.30 (s, 3H), 4.51 (s, 2H), 4.68 (s, 2H), 7.05 (dd, J=7.9, 2.3 Hz, 1H), 7.30 (d, J=1.5 Hz, 1H), 7.46 (d, J=8.2 Hz, 1H).

3.4
2-Bromo-5-methoxy-1-(methoxymethoxymethyl)benzene (18g)

This compound was made from 2-bromo-5-methoxybenzoic acid in the same manner as compound 18d: $^1$H NMR (300 MHz, DMSO-$d_6$): δ 3.30 (s, 1H), 3.74 (s, 3H), 4.50 (s, 2H), 4.69 (s, 2H), 6.83 (dd, J=8.8, 2.9 Hz, 1H), 7.40 (d, J=2.9 Hz, 1H), 7.48 (d, J=8.8 Hz, 1H).

3.5
2-Bromo-1,5-bis(methoxymethoxymethyl)benzene (18h)

This compound was made from 4-bromo-1,3-phthalic acid in the same manner as compound 18d: $^1$H NMR (300 MHz, CDCl$_3$) δ (ppm) 3.28 (s, 3H), 3.30 (s, 3H), 4.50 (s, 2H), 4.54 (s, 2H), 4.64 (s, 2H), 4.69 (s, 2H), 7.20 (dd, J=8.8, 2.5 Hz, 1H), 7.46 (d, J=2.5 Hz, 1H), 7.58 (d, J=8.8 Hz, 1H).

3.6 2-Bromo-4,5-difluoro-1-(methoxymethoxymethyl)benzene (18k)

This compound was made from 2-bromo-4,5-difluorobenzoic acid in the same manner as compound 18d: $^1$H NMR (300 MHz, CDCl$_3$) δ (ppm) 3.42 (s, 3H), 4.57 (d, J=1.2 Hz, 2H), 4.76 (s, 2H), 7.3-7.5 (m, 2H).

3.7
2-Bromo-6-fluoro-1-(methoxymethoxymethyl)benzene (18l)

This compound was made from 2-bromo-6-fluorobenzoic acid in the same manner as compound 18d: $^1$H NMR (300 MHz, CDCl$_3$) δ (ppm) 3.43 (s, 3H), 4.74 (s, 2H), 4.76 (d, J=2.1 Hz, 2H), 7.05 (t, J=9.1 Hz, 1H), 7.18 (td, J=8.2, 5.9 Hz, 1H), 7.40 (d, J=8.2 Hz, 1H).

3.8
2-Bromo-4-fluoro-1-(methoxymethoxymethyl)benzene (18m)

This compound was made from 2-bromo-4-fluorobenzoic acid in the same manner as compound 18d and was used for the next step without purification.

3.9
4-Bromo-3-(methoxymethoxymethyl)benzonitrile (18f)

To a solution of 17 (10.0 g, 49.5 mmol) in carbon tetrachloride (200 mL) were added N-bromosuccinimide (8.81 g, 49.5 mmol) and 2,2'-azobis(isobutyronitrile) (414 mg, 5 mol %), and the mixture was refluxed for 3 h. Water was added, and the mixture was extracted with chloroform. The organic layer was washed with brine and dried over anhydrous sodium sulfate. The solvent was removed under reduced pressure. To the residue were added dimethylformamide (150 mL) and sodium acetate (20.5 g, 250 mmol), and the mixture was stirred at 80° C. overnight. Water was added, and the mixture was extracted with ether. The organic layer was washed with water and brine, and dried over anhydrous sodium sulfate. The solvent was removed under reduced pressure. To the residue was added methanol (150 mL) and 1 mol/L sodium hydroxide (50 mL), and the mixture was stirred at room temperature for 1 h. The reaction mixture was concentrated to about a third of volume under reduced pressure. Water and hydrochloric acid were added, and the mixture was extracted with ethyl acetate. The organic layer was washed with water and brine, and dried over anhydrous sodium sulfate. The solvent was removed under reduced pressure, and the residue was purified by silica gel column chromatography (3:1 hexane/ethyl acetate) followed by trituration with dichloromethane to give 2-bromo-5-cyanobenzyl alcohol (4.63 g, overall 44%): $^1$H NMR (300 MHz, DMSO-$d_6$) δ (ppm) 4.51 (d, J=5.9 hz, 2H), 5.67 (t, J=5.6 Hz, 1H), 7.67 (dd, J=8.2, 2.0 Hz, 1H), 7.80 (s, J=8.2 Hz, 1H), 7.83 (d, J=2.0 Hz, 1H).

To a solution of 2-bromo-5-cyanobenzyl alcohol (4.59 g, 21.7 mmol) in dichloromethane (80 mL) were added diisopropylethylamine (5.6 mL, 32 mmol) and chloromethyl methyl ether (2.3 mL, 30 mmol) at 0° C., and the reaction mixture was stirred at room temperature overnight. Water was added, and the mixture was extracted with chloroform. The organic layer was washed with brine and dried over anhydrous sodium sulfate. The solvent was removed under reduced pressure. The residue was purified by silica gel column chromatography (6:1 hexane/ethyl acetate) to give 18f (4.08 g, 71%): $^1$H NMR (300 MHz, CDCl$_3$) δ (ppm) 3.43 (s, 3H), 4.65 (s, 2H), 4.80 (s, 2H), 7.43 (dd, J=8.2, 4.1 Hz, 1H), 7.66 (d, J=8.2 Hz, 1H), 7.82 (d, J=4.1 Hz, 1H).

3.10 2-Bromo-5-trifluoromethyl-1-(methoxymethoxymethyl)benzene (18l)

This compound was made from 2-bromo-5-trifluoromethylbenzaldehyde in the same manner as compound 5b and used for the next step without purification.

3.11
1-Bromo-2-(methoxymethoxymethyl)naphthalene (18j)

This compound was made from 1-bromonaphthaldehyde in the same manner as compound 5b: $^1$H NMR (300 MHz, CDCl$_3$) δ (ppm) 3.42 (s, 3H), 4.75 (s, 2H), 4.81 (s, 2H), 7.5-7.7 (m, 3H), 7.99 (d, J=7.7 Hz, 2H), 8.22 (d, J=7.7 Hz, 1H).

3.12 1,3-Dihydro-1-hydroxy-2,1-benzoxaborole (19a)

This compound was purchased from Lancaster Synthesis.

3.13
1,3-Dihydro-5-fluoro-1-hydroxy-2,1-benzoxaborole (19b)

To a solution of 5b (73.2 g, 293 mmol) in dry THF (400 mL) was added n-butyllithium (1.6 M in hexanes; 200 mL) over 45 min at −78° C. under nitrogen atmosphere. Anion precipitated. After 5 min, (i-PrO)$_3$B (76.0 mL, 330 mmol) was added over 10 min, and the mixture was allowed to warm to room temperature over 1.5 h. Water and 6 N HCl (55 mL) were added, and the solvent was removed under reduced pressure to about a half volume. The mixture was poured into ethyl acetate and water. The organic layer was washed with brine and dried over anhydrous Na$_2$SO$_4$. The solvent was removed under reduced pressure. To a solution of the residue in tetrahydrofuran (360 mL) was added 6 N HCl (90 mL), and the mixture was stirred at 30° C. overnight. The solvent was removed under reduced pressure to about a half volume. The mixture was poured into ethyl acetate and water. The organic layer was washed with brine and dried over anhydrous Na$_2$SO$_4$. The solvent was removed under reduced pressure, and the residue was treated with i-Pr$_2$O/hexane to give 19b (26.9 g, 60%) as a white powder: mp 118-120° C.; $^1$H NMR (300 MHz, DMSO-d$_6$) δ (ppm) 4.95 (s, 2H), 7.15 (m, 1H), 7.24 (dd, J=9.7, 1.8 Hz, 1H), 7.74 (dd, J=8.2, 6.2 Hz, 1H), 9.22 (s, 1H); ESI-MS m/z 151 (M−H)$^−$; HPLC purity 97.8%; Anal (C$_7$H$_6$BFO$_2$) C, H.

3.14 1,3-Dihydro-5-fluoro-1-hydroxy-3-methyl-2,1-benzoxaborolane (19c)

This compound was made from 18c in the same manner as compound 19b: mp 72-76° C. $^1$H NMR (300 MHz, DMSO-d$_6$) δ (ppm) 1.37 (d, J=6.4 Hz, 3H), 5.17 (q, J=6.4 Hz, 1H), 7.14 (m, 1H), 7.25 (dd, J=9.7, 2.3 Hz, 1H), 7.70 (dd, J=8.2, 5.9 Hz, 1H), 9.14 (s, 1H). ESI-MS m/z 165 (M−H)$^−$; HPLC purity 95.2%; Anal (C$_8$H$_8$BFO$_2$) C, H.

3.15 5-Chloro-1,3-dihydro-1-hydroxy-2,1-benzoxaborole (19d)

This compound was made from 18d in the same manner as compound 19b: mp 142-144° C. $^1$H NMR (300 MHz, DMSO-d$_6$) δ (ppm) 4.96 (s, 2H), 7.38 (d, J=7.8 Hz, 1H), 7.49 (s, 1H), 7.71 (d, J=7.8 Hz, 1H), 9.30 (s, 1H); ESI-MS m/z 167 (M−H)$^−$; HPLC purity 99.0%; Anal (C$_7$H$_6$ClO$_2$·0.1H$_2$O)C, H.

3.16 1,3-Dihydro-1-hydroxy-5-methyl-2,1-benzoxaborole (19e)

This compound was made from 18e in the same manner as compound 19b: mp 124-128° C.; $^1$H NMR (300 MHz, DMSO-d$_6$) δ (ppm) 2.33 (s, 3H), 4.91 (s, 2H), 7.13 (d, J=7.2 Hz, 1H), 7.18 (s, 1H), 7.58 (d, J=7.2 Hz, 1H), 9.05 (s, 1H); ESI-MS m/z 147 (M−H)$^−$; HPLC purity 99.0%; Anal (C$_8$H$_8$BO$_2$) C, H.

3.17 1,3-Dihydro-1-hydroxy-5-methoxy-2,1-benzoxaborole (19g)

This compound was made from 18g in the same manner as compound 19b: mp 102-104° C.; $^1$H NMR (300 MHz, DMSO-d$_6$) δ (ppm) 3.77 (s,3H), 4.91 (s, 2H), 6.88 (d, J=8.1 Hz, 1H), 6.94 (s, 1H), 7.60 (d, J=8.1 Hz, 1H), 8.95 (s, 1H); ESI-MS m/z 163 (M−H)$^−$; HPLC purity 100%; Anal (C$_8$H$_8$BO$_3$) C, H.

3.18 1,3-Dihydro-1-hydroxy-5-hydroxymethyl-2,1-benzoxaborole (19h)

This compound was made from 18h in the same manner as compound 19b: mp 124-128° C.; $^1$H NMR (300 MHz, DMSO-d$_6$) δ (ppm) 4.53 (d, 2H), 4.94 (s, 2H), 5.24 (t, 1H), 7.26 (d, 1H), 7.33 (s, 1H), 7.64 (d, 1H), 9.08 (s, 1H); ESI-MS m/z 163 (M−H)$^−$; HPLC purity 100%.

3.19 1,3-Dihydro-1-hydroxy-5-trifluoromethoxy-benzoxaborole (19i)

This compound was made from 18l in the same manner as compound 19b: mp 113-118° C.; $^1$H NMR (300 MHz, DMSO-d$_6$) δ (ppm) 5.05 (s, 2H), 7.65-7.68 (d, J=7.5 Hz, 1H), 7.78 (s, 1H), 7.90-7.93 (d, J=7.8 Hz, 1H), 9.47 (s, 1H); ESI-MS m/z 201 (M−H)$^−$; HPLC purity 100%.

3.20 1,3-Dihydro-1-hydroxy-2,1-naphtho[2,1-d]oxaborole (19j)

This compound was made from 18j in the same manner as compound 19b: mp 139-143° C.; $^1$H NMR (300 MHz, DMSO-d$_6$) δ (ppm) 5.09 (s, 2H), 7.59-7.47 (m, 3H), 7.95 (d, J=7.5 Hz, 1H), 7.99 (d, J=8.1 Hz, 1H), 8.28 (dd, J=6.9, 0.6 Hz, 1H), 9.21 (s, 1H); ESI-MS m/z 185 (M+H)$^+$; Anal (C$_{11}$H$_9$BO$_2$) C, H.

3.21 1,3-Dihydro-4-fluoro-1-hydroxy-2,1-benzoxaborole (19l)

This compound was made from 18L in the same manner as compound 19b: $^1$H NMR (300 MHz, DMSO-d$_6$) δ (ppm) 5.06 (s, 2H), 7.26 (ddd, J=9.7, 7.9, 0.6 Hz, 1H), 7.40 (td, J=8.2, 4.7 Hz, 1H), 7.55 (d, J=7.0 Hz, 1H), 9.41 (s, 1H); ESI-MS m/z 151 (M−H)$^−$; HPLC purity 98.7%; Anal (C$_7$H$_6$BFO$_2$) C, H.

3.22 1,3-Dihydro-6-fluoro-1-hydroxy-2,1-benzoxaborole (19m)

This compound was made from 18m in the same manner as compound 19b: $^1$H NMR (300 MHz, DMSO-d$_6$) δ (ppm) 4.95 (s, 2H), 7.29 (td, J=9.0, 2.7 Hz, 1H), 7.41-7.46 (m, 2H), 9.29 (s, 1H); ESI-MS m/z 151 (M−H)$^−$; HPLC purity 100%; Anal (C$_7$H$_6$BFO$_2$) C, H.

3.23 5,6-Difluoro-1,3-dihydro-1-hydroxy-2,1-benzoxaborolane (19k)

To a solution of 18k (2.97 g, 11.1 mmol) and (i-PrO)$_3$B (2.8 mL, 12 mmol) in THF (30 mL) was added n-BuLi (1.6 mol/L in hexane; 7.5 mL) over 30 min at −78° C. under nitrogen atmosphere, and the mixture was stirred for 2 h while allowing to warm to room temperature. The reaction was quenched with 2 N HCl, and the mixture was extracted with EtOAc. The organic layer was washed with brine and dried over anhydrous Na$_2$SO$_4$. The solvent was removed under reduced pressure. To a solution of the residue in THF (25 mL) was added 6 N HCl (5 mL), and the mixture was stirred at room temperature overnight. Water was added and the mixture was extracted with EtOAc. The organic layer was washed with brine and dried over anhydrous Na$_2$SO$_4$. The solvent was removed under reduced pressure. Recrystallization from EtOAc/i-Pr$_2$O gave 19k (1.14 g, 60%) as a white powder: mp 134-140° C. $^1$H NMR (300 MHz, DMSO-d$_6$) δ (ppm) 4.94 (s, 2H), 7.50 (dd, J=10.7, 6.8 Hz, 1H), 7.62 (dd, J=9.7, 8.2 Hz, 1H), 9.34 (s, 1H). ESI-MS m/z 169 (M−H)$^−$; HPLC purity 96.6%; Anal (C$_7$H$_5$BF$_2$O$_2$) C, H.

3.24 5-Cyano-1,3-dihydro-1-hydroxy-2,1-benzoxaborolane (19f)

This compound was made from 18f in the same manner as compound 19k: mp 98-101° C. $^1$H-NMR (300 MHz, DMSO-d$_6$) δ (ppm) 5.03 (s, 2H), 7.76 (d, J=8.2 Hz, 1H), 7.89 (d, J=8.2 Hz, 1H), 7.90 (s, 1H), 9.53 (s, 1H); ESI-MS m/z 158 (M−H)$^-$; HPLC purity 97.7%.

3.25
1,3-Dihydro-7-fluoro-1-hydroxy-2,1-benzoxaborolane (19n)

To a solution of 20 (2.00 g, 15.9 mmol) and TMEDA (5.70 mL, 38.0 mmol) in THF (100 mL) was added sec-butyllithium (25 mL, 35.0 mmol) as 1.4 M solution at −78° C. The mixture was stirred at −78° C. for 1 h before (i-PrO)$_3$B (8.10 mL, 35.0 mmol) was added. The reaction was warmed up to room temperature very slowly, then was stirred overnight. Water was added, and the pH was adjusted to 12, then it was washed with ethyl ether. The aqueous layer was acidified to pH 2 using 6 N HCl, then extracted with ethyl ether, washed with brine, dried over Na$_2$SO$_4$ and concentrated under reduced pressure. The crude product was purified by flash column chromatography (2:1 hexane/ethyl acetate) to give 19n (270 mg) as a white solid: mp 120-124° C. $^1$H NMR (300 MHz, DMSO-d$_6$) δ (ppm) 4.99 (s,2H), 7.00 (t, J=8.7 Hz, 1H), 7.21 (d, J=7.8 Hz, 1H), 7.48 (td, J=5.1, 7.8 Hz, 1H), 9.25 (s, 1H); ESI-MS m/z 151 (M−H)$^-$; HPLC purity 97.4%; Anal (C$_8$H$_6$BNO$_2$) C, H.

Example 4

Benzoxaborin

4.1 2-Bromo-5-fluorophenylacetaldehyde (21a)

A mixture of compound 3 (4.23 g, 20.0 mmol), (methoxymethyl)triphenylphosphonium chloride (8.49 g, 24.0 mmol), and potassium tert-butoxide (2.83 g, 24.0 mol) in N,N-dimethylformamide (50 mL) was stirred at room temperature overnight. The reaction was quenched with 6 N hydrochloric acid, and the mixture was extracted with ethyl acetate. The organic layer was washed with water twice and brine, and dried over anhydrous sodium sulfate. The solvent was removed under reduced. To the residue were added tetrahydrofuran (60 mL) and 6 N hydrochloric acid, and the mixture was heated at reflux for 8 h. Water was added, and the mixture was extracted with ether. The organic layer was washed with brine and dried over anhydrous sodium sulfate. The solvent was removed under reduced pressure to afford 21a (3.60 g, 83%): $^1$H NMR (300 MHz, CDCl$_3$) δ (ppm) 3.86 (d, J=1.5 Hz, 2H), 6.9-7.1 (m, 2H), 7.57 (dd, J=8.8, 5.3 Hz, 1H), 9.76 (t, J=1.5 Hz, 1H).

4.2 1-Bromo-4-fluoro-2-[2-(methoxymethoxy)ethyl]benzene (22a)

To a solution of 21a (3.60 g, 16.6 mmol) in methanol (40 mL) was added sodium borohydride (640 mg, 16.6 mmol) at 0° C., and the mixture was stirred at room temperature for 1 h. Water was added, and the mixture was extracted with ethyl acetate. The organic layer was washed with brine and dried over anhydrous sodium sulfate. The solvent was removed under reduced pressure. To the residue were added dichloromethane (50 mL), diisopropylethylamine (3.5 mL, 20 mmol) and chloromethyl methyl ether (1.5 mL, 20 mmol) at 0° C., and the reaction mixture was stirred at room temperature overnight. Water was added, and the mixture was extracted with chloroform. The organic layer was washed with brine and dried over anhydrous sodium sulfate. The solvent was removed under reduced pressure. The residue was purified by silica gel column chromatography (15:1 hexane/ethyl acetate) to give 22a (2.99 g, 2 steps 68%) as a colorless oil: $^1$H NMR (300 MHz, CDCl$_3$) δ (ppm) 3.04 (t, J=6.7 Hz, 2H), 3.31 (s, 3H), 3.77 (t, J=6.7 Hz, 2H), 4.62 (s, 2H), 6.82 (td, J=8.2, 3.2 Hz, 1H), 7.04 (dd, J=9.4, 2.9 Hz, 1H), 7.48 (dd, J=8.8, 5.3 Hz, 1H).

4.3 1-Bromo-2-[2-(methoxymethoxy)ethyl]benzene (22b)

This compound was synthesized from 21b in a similar manner to 22a and used for the next step without purification.

4.4 6-Fluoro-1-phenyl-1,2,3,4-tetrahydro-2,1-benzoxaborine (23a)

This compound was synthesized from 22a and 7a in a similar manner to compound 9f: colorless oil; $^1$H NMR (300 MHz, CDCl$_3$) δ (ppm) 3.02 (t, J=6.1 Hz, 2H), 4.34 (t, J=6.1 Hz, 2H), 6.9-7.1 (m, 2H), 7.4-7.6 (m, 3H), 7.8-7.9 (m, 3H); ESI-MS m/z 227 (M+H)$^+$; HPLC purity 95.3%; Anal (C$_{14}$H$_{12}$BFO 0.1H$_2$O)C, H.

4.5 1-Phenyl-1,2,3,4-tetrahydro-2,1-benzoxaborine (23b)

This compound was synthesized from 22b and 7a in a similar manner to compound 9f: colorless oil; $^1$H NMR (300 MHz, DMSO-d$_6$) δ (ppm) 2.94 (t, J=5.9 Hz, 2H), 4.21 (t, J=5.9 Hz, 2H), 7.28 (t, J=7.9 Hz, 2H), 7.3-7.5 (m, 4H), 7.66 (d, J=7.0 Hz, 1H), 7.75 (d, J=7.6 Hz, 2H); ESI-MS m/z not observed; HPLC purity 96.0%; Anal (C$_{14}$H$_{13}$BO) C. H.

4.6 6-Fluoro-1-hydroxy-1,2,3,4-tetrahydro-2,1-benzoxaborine (24)

This compound was synthesized from 22a in a similar manner to compound 19b. Silica gel column chromatography (2:1 hexane/ethyl acetate) followed by trituration with pentane 24 as a white powder: mp 77-82° C.; $^1$H NMR (300 MHz, DMSO-d$_6$) δ (ppm) 2.86 (t, J=5.9 Hz, 2H), 4.04 (t, J=5.9 Hz, 2H), 7.0-7.1 (m, 2H), 7.69 (dd, J=8.2, 7.2 Hz, 1H), 8.47 (s, 1H); ESI-MS m/z 165 (M−H)$^-$; HPLC purity 99.0%; Anal (C$_8$H$_8$BFO$_2$) C, H.

Example 5

Determination of Minimum Inhibitory Concentration (MIC) Against Fungi

All MIC testing against *Trichophyton rubrum, Trichophyton mentagrophytes, Candida albicans, Cryptococcus neoformans* and *Aspergillus fumigatus* were determined following the National Committee for Clinical Laboratory Standards (NCCLS) guidelines for antimicrobial testing of yeasts and filamentous fungi.[i,ii]

Briefly, compounds were dissolved in DMSO and diluted in sterile water to give a working stock. Two-fold serial dilutions of the test compounds were prepared in 96-well plates. The plates were inoculated with the fungal suspensions to give a final inoculum size of 0.5–2.5×10$^3$ cells/mL for yeasts or 0.4–5×10$^4$ CFU/mL for filamentous fungi and then incubated for 24-168 h at 35° C. The final concentration of DMSO did not exceed 5%. The MIC was defined as the lowest concentration that resulted in over 90% reduction of growth, as compared to a drug-free control.

i. Pfaller M A, Chaturvedi V, Espinel-Ingroff A, Ghannoum M A, Gosey L L, Odds F C, Rex J H, Rinaldi M G, Sheehan D J, Walsh T J, Warnock D W. NCCLS publication M27-A2—Reference Method for Broth Dilution Antifungal Susceptibility Testing of Yeasts; Approved Standard—Second Edition. Wayne, P A: NCCLS; 2002 (Vol. 22, No. 15).

ii. Pfaller M A, Chaturvedi V, Espinel-Ingroff A, Ghannoum M A, Gosey L L, Odds F C, Rex J H, Rinaldi M G, Sheehan D J, Walsh T J, Warnock D W. NCCLS publication M38-A—Reference Method for Broth Dilution Antifungal Susceptibility Testing of Filamentous Fungi; Approved Standard. Wayne, P A: NCCLS; 2002 (Vol. 22, No. 16).

Elemental Analysis Data

| Compound | Formula | Calcd | Found |
|---|---|---|---|
| 9c | $C_{13}H_{10}BClO$ | C, 68.34; H, 4.41 | C, 68.62; H, 4.52 |
| 9d | $C_{13}H_{10}BFO$ | C, 73.64; H, 4.75 | C, 73.62; H, 4.78 |
| 9e | $C_{13}H_{10}BFO$ | C, 73.64; H, 4.75 | C, 73.45; H, 4.89 |
| 9f | $C_{13}H_9BClFO$ | C, 63.35; H, 3.68 | C, 63.13; H, 3.68 |
| 9g | $C_{13}H_9BF_2O$ | C, 67.88; H, 3.94 | C, 68.06; H, 4.11 |
| 9h | $C_{13}H_9BF_2O$ | C, 67.88; H, 3.94 | C, 67.56; H, 4.00 |
| 9i | $C_{14}H_{12}BFO$ | C, 74.38; H, 5.35 | C, 74.28; H, 5.48 |
| 9j | $C_{14}H_{12}BFO$ | C, 74.38; H, 5.35 | C, 74.40; H, 5.60 |
| 10a | $C_{15}H_{13}BO \cdot 0.1H_2O$ | C, 81.20; H, 6.00 | C, 81.14; H, 6.07 |
| 10b | $C_{15}H_{12}BFO$ | C, 75.68; H, 5.08 | C, 75.61; H, 4.64 |
| 11 | $C_9H_8BFO \cdot 0.1H_2O$ | C, 66.00; H, 5.05 | C, 65.98; H, 4.98 |
| 12 | $C_{11}H_8BFO_2$ | C, 65.41; H, 3.99 | C, 65.39; H, 4.10 |
| 13 | $C_{11}H_8BFOS$ | C, 60.59; H, 3.70 | C, 60.63; H, 3.62 |
| 14 | $C_{12}H_{10}BFOS$ | C, 62.10; H, 4.34 | C, 62.19; H, 4.22 |
| 15 | $C_{12}H_9BFNO \cdot 0.6H_2O$ | C, 64.39; H, 4.59; N, 6.26 | C, 64.43; H, 4.25; N, 6.48 |
| 19b | $C_7H_6BFO_2$ | C, 55.34; H, 3.98 | C, 55.15; H, 3.80 |
| 19c | $C_8H_8BFO_2$ | C, 57.90; H, 4.86 | C, 58.12; H, 4.82 |
| 19d | $C_7H_6BClO_2 \cdot 0.1H_2O$ | C, 49.40; H, 3.67 | C, 49.28; H, 3.50 |
| 19e | $C_8H_9BO_2$ | C, 64.94; H, 6.13 | C, 65.14; H, 6.33 |
| 19g | $C_8H_9BO_3$ | C, 58.60; H, 5.53 | C, 58.71; H, 5.71 |
| 19j | $C_{11}H_9BO_2$ | C, 71.80; H, 4.93 | C, 72.00; H, 4.89 |
| 19k | $C_7H_5BF_2O_2$ | C, 49.48; H, 2.97 | C, 49.17; H, 2.81 |
| 19L | $C_7H_6BFO_2$ | C, 55.34; H, 3.98 | C, 55.24; H, 3.94 |
| 19m | $C_7H_6BFO_2$ | C, 55.34; H, 3.98 | C, 55.17; H, 3.89 |
| 19n | $C_7H_6BFO_2$ | C, 55.34; H, 3.98 | C, 55.19; H, 3.93 |
| 23a | $C_{14}H_{12}BFO \cdot 0.1H_2O$ | C, 73.80; H, 5.40; | C, 73.93; H, 5.68 |
| 23b | $C_{14}H_{13}BO$ | C, 80.82; H, 6.30 | C, 80.98; H, 5.60 |
| 24 | $C_8H_8BFO_2$ | C, 57.90; H, 4.86 | C, 58.03; H, 4.87 |

The disclosures in this application of all articles and references, including patents, are incorporated herein by reference.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The invention is described in more detail in the following non-limiting examples. It is to be understood that these methods and examples in no way limit the invention to the embodiments described herein and that other embodiments and uses will no doubt suggest themselves to those skilled in the art.

The compounds of this invention are evaluated for their antibacterial activity as per the guidelines and procedures prescribed by the National Committee for Clinical Laboratory Standards (NCCLS) (cf., NCCLS Document M7-A3, 1993—Antimicrobial Susceptibility Testing).

Protocol for MIC Determination

A useful protocol for MIC determination is as follows:
1. Approximately 2.5 mg of the compounds to be tested was weighed into cryovials.
2. 5 mg/ml stock solutions were made by adding DMSO to the samples accordingly.
3. 256 µg/ml working solutions were made by using the 5 mg/ml stock solutions and adding sterile distilled water accordingly.
4. A Beckman 2000 Automated Workstation was programmed to load 96 well plates with broth and compounds as follows:
   100 µl of the appropriate broth was added to columns 1-11
   200 µl of the appropriate broth was added to column 12
   100 µl of compounds at the 256 µg/ml working solution were added to column 1 (one compound per row)
   Two-fold serial dilutions were done from column 1 to 10
   Column 11 served as the growth control
5. The 10 organism panel was plated from stock vials stored at −80° C. and incubated for 24 hours at 34° C. The organisms were then sub-cultured and incubated for 24 hours at 34° C.
   The inoculums were first prepared in sterile distilled water with a target of 0.09-0.11 absorbance at 620 nm wavelength
   A 1/100 dilution was made into the appropriate broth
   100 µl of broth with organism was added to columns 1-11
   Column 12 served as the blank control
6. The completed 96 well plates were incubated for 24 hours at 34° C. The 96 well plates were then read using a Beckman Automated Plate Reader at 650 nm wavelength. The MIC was determined through calculations involving the growth control (column 11) and blank control (column 12).

Calculations

The absorbance readings from the Biomek Automated Plate Reader are used to determine the percent inhibition for each test well. The formula used is as follows:

$$\% \text{ Inhibition} = [1-(ABS_{test}-ABS_{blank})/(ABS_{mean\ growth}-ABS_{blank})] \times 100\%$$

$ABS_{test}$: Absorbance of the test well
$ABS_{blank}$: Absorbance of the blank well in the same row as the test well (column 12)
$ABS_{mean\ growth}$: Mean absorbance of the growth control wells (column 11)

The minimum inhibitory concentration (MIC) is found at the lowest concentration of compound where percent inhibition is greater than or equal to 80%.

These procedures were used to obtain the representative microbiological data for the compounds 10 to 19 shown in Table 1 as MIC (Minimum Inhibitory Concentration) with the values expressed as micrograms per ml.

The compounds of this invention are evaluated for their antiviral activity as per the guidelines and procedures prescribed.

Protocols for Antiviral Determination

Yellow Fever (YFV) antiviral assay was performed with HeLa cells which were used in order to allow for a 7 day assay endpoint. HeLa cells were passaged in T-75 flasks. On the day preceding the assay, the cells were trypsinized, pelleted, counted and resuspended at $1 \times 10^4$/well in tissue culture medium in 96-well flat bottom tissue culture plates in a volume of 100 µl per well. One day following plating of cells, the wells were washed and the medium was replaced with complete medium (2% serum) containing various concentrations of test compound diluted in medium in a half-log series. A pretitered aliquot of 17D strain YFV virus was removed from the freezer (−80° C.) just before each experiment. The virus was diluted into tissue culture medium such that the amount of virus added to each well would give complete cell killing at 7 days post-infection.

HepG2 2.15 Antiviral Evaluation Assay—HepG2 2.2.15 cells, which produce HBV aywl strain, were plated in 96-well collagen coated microtiter plates at a density of $2.5 \times 10^4$/well with DMEM medium supplemented with 2% fetal bovine serum. One day following plating of cells, the wells were washed and the medium was replaced with complete medium containing the test compound diluted in the medium in a half-log series.

The medium was replaced once with the fresh medium containing the freshly diluted compound three days post the initial addition of the lamivudine, a positive control compound. Cell viability was determined using CellTiter 96® Reagent (Promega, Madison, Wis.) according to the manufacturer's protocol, using a Vmax plate reader (Molecular Devices, Sunnyvale, Calif.). The mixture is metabolized by the mitochondrial enzymes of metabolically active cells to a soluble formazan product, allowing the rapid quantitative analysis of cell numbers. The media was removed and replaced with 100 µg of fresh media and 10 µg of Cell Titer 96. Plates were reincubated for 4 hours at 37° C. and read spectrophotometrically at 490 and 650 nm with a Molecular Devices Vmax plate reader. Percent cell viability of compound treated wells compared to no compound controls was calculated using an in-house computer program which graphs the percent reduction in viral cytopathic effects and the cell numbers at each drug concentration relative to control values. The program interpolates the inhibitory concentration of drug that reduces cytopathic effects by 50% (IC50) and the toxic concentration that kills 50% of cells (TC50).

HCV RNA Replicon Antiviral Evaluation Protocol

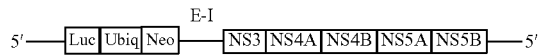

The cell line ET (luc-ubi-neo/ET), a new HCV RNA replicon that contains a stable luciferase (LUC) reporter, was used. The composition of the replicon is shown diagrammatically above (ref. Krieger, N., V. Lohmann, and R. Bartenschlager. 2001. Enhancement of hepatitis C virus RNA replicon replication by cell culture-adaptive mutations. J. Virol. 75:4614-4624). The HCV RNA replicon ET contains the 5' NTR (IRES) of HCV (5') which drives the production of a firefly luciferase (Luc), ubiquitin (Ubiq), and neomycin phosphotransferase (Neo) fusion protein. Ubiquitin cleavage releases the LUC and Neo genes. The EMCV IRES element (E-I) controls the translation of the HCV structural proteins NS3-NS5.

The NS3 protein cleaves the HCV polyprotein to release the mature NS3, NS4A, NS4B, NS5A and NS5B proteins that are required for HCV replication. At the 3' end of the replicon is the authentic 3' NTR of HCV. The LUC reporter is used as an indirect measure of HCV replication. The activity of the LUC reporter is directly proportional to HCV RNA levels and positive control antiviral compounds behave comparably using either LUC or RNA endpoints. The use of the LUC endpoint is more economical than HCV RNA and can be used for high-throughput applications to screen libraries of compounds.

The HCV RNA replicon antiviral evaluation assay examines the effects of compounds at five half-log concentrations each. Human interferon alpha-2b is included in each run as a positive control compound. Subconfluent cultures of the ET line are plated out into 96-well plates that are dedicated for the analysis of cell numbers (cytotoxicity) or antiviral activity and the next day drugs are added to the appropriate wells. Cells are processed 72 hr later when the cells are still subconfluent. Compound IC50 and IC90 values are derived from HCV RNA levels assessed as either HCV RNA replicon-derived LUC activity or as HCV RNA using TaqMan RT-PCR. Compound TC50 and TC90 values are calculated using a calorimetric assay as an indicator of cell numbers and cytotoxicity when the LUC assay system is employed, while ribosomal (rRNA) levels determined via TaqMan RTPCR are used as an indication of cell numbers in the RNA-based assay. Compound T150 and T190 values are calculated from spreadsheets.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound of Formula (I)

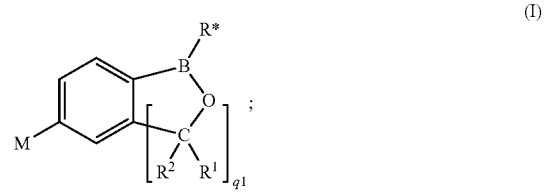

wherein

B is boron;

q1 is an integer selected from 1 to 3;

M is a member selected from halogen, —OCH$_3$, and —CH$_2$—O—CH$_2$—O—CH$_3$;

R$^1$ and R$^2$ are members independently selected from H, OH, NH$_2$, SH, CN, NO$_2$, OSO$_2$OH, OSO$_2$NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

R* is a member selected from:

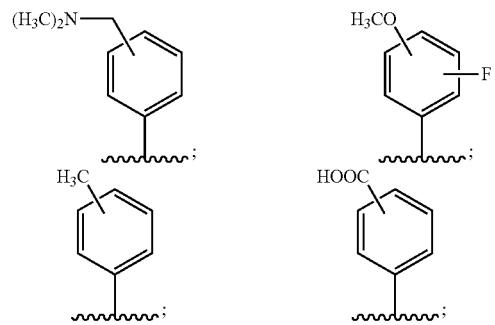

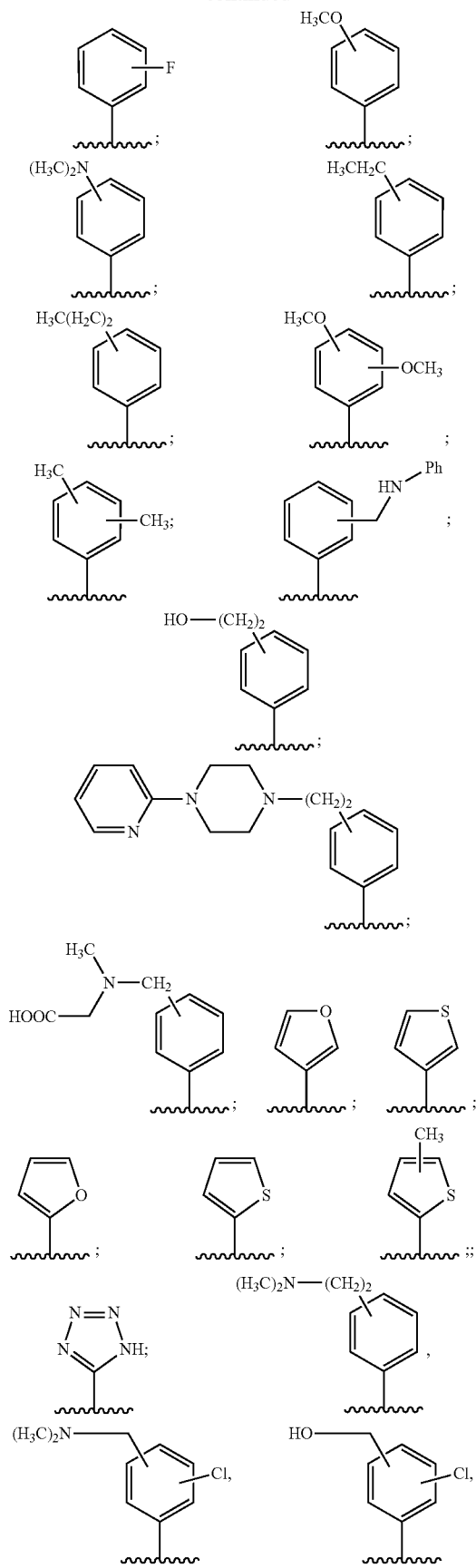
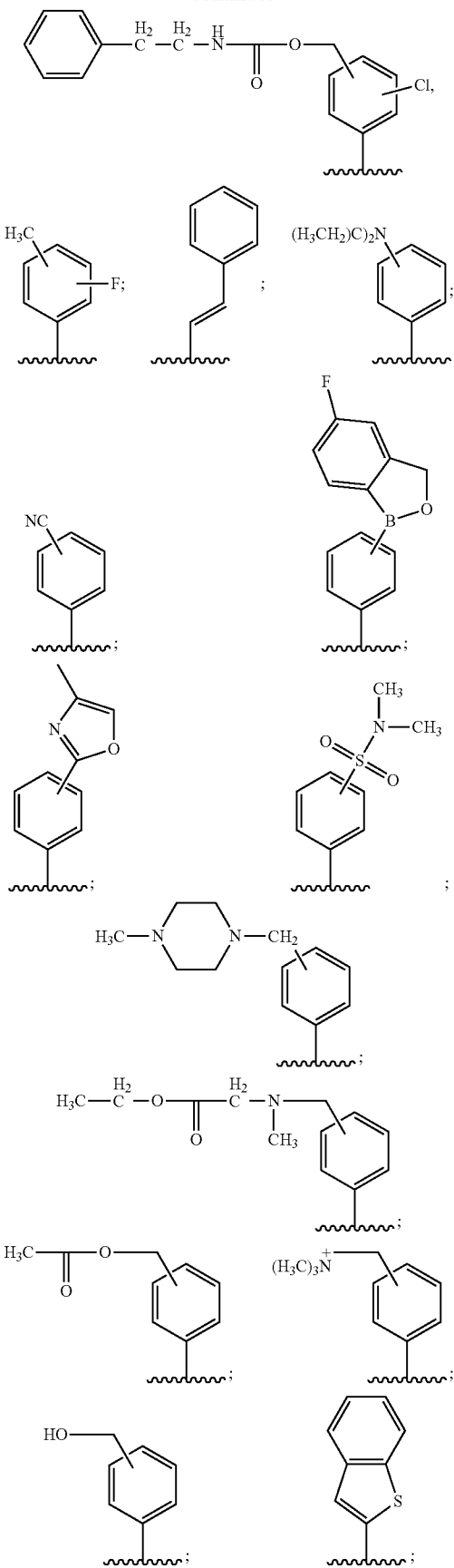

-continued

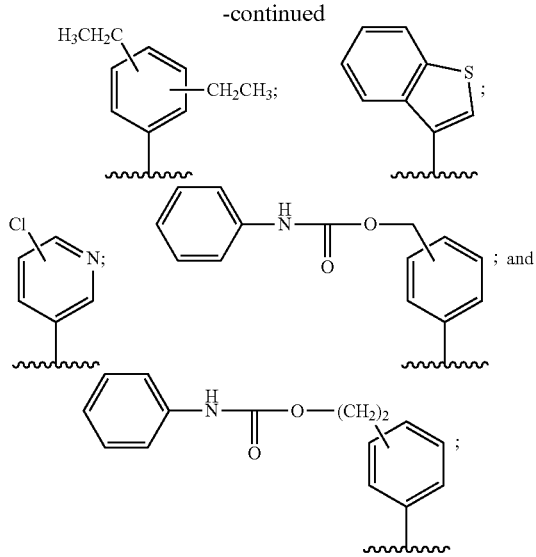

with the proviso that when M is F, R* is not a member selected from:

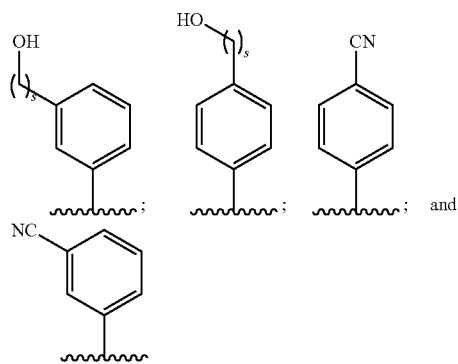

wherein s is an integer selected from 1 and 2;
and with the proviso that when M is Cl, R* is not a member selected from:

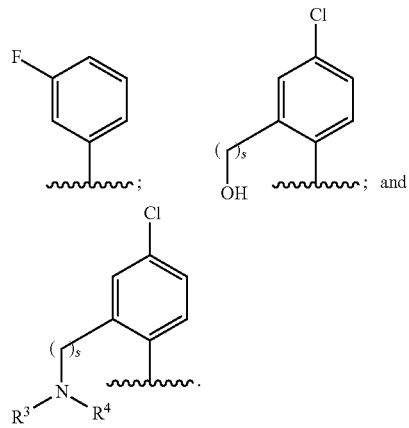

wherein s is 1; and
$R^3$ and $R^4$ are methyl;
including salts thereof.

2. A compound of Formula (I)

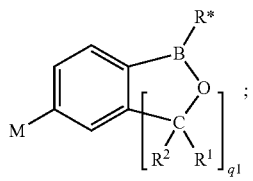

(I)

wherein
B is boron;
q1 is an integer selected from 1 to 3;
M is a member selected from halogen, —OCH$_3$, and —CH$_2$—O—CH$_2$—O—CH$_3$;
$R^1$ and $R^2$ are members independently selected from H, OH, NH$_2$, SH, CN, NO$_2$, OSO$_2$OH, OSO$_2$NH$_2$, substituted or unsubstituted alkyl, substituted or unsubstituted hetcroalkyl, substituted or unsubstituted cycloalkyl, substituted or unsubstituted heterocycloalkyl, substituted or unsubstituted aryl and substituted or unsubstituted heteroaryl;
R* is a member selected from

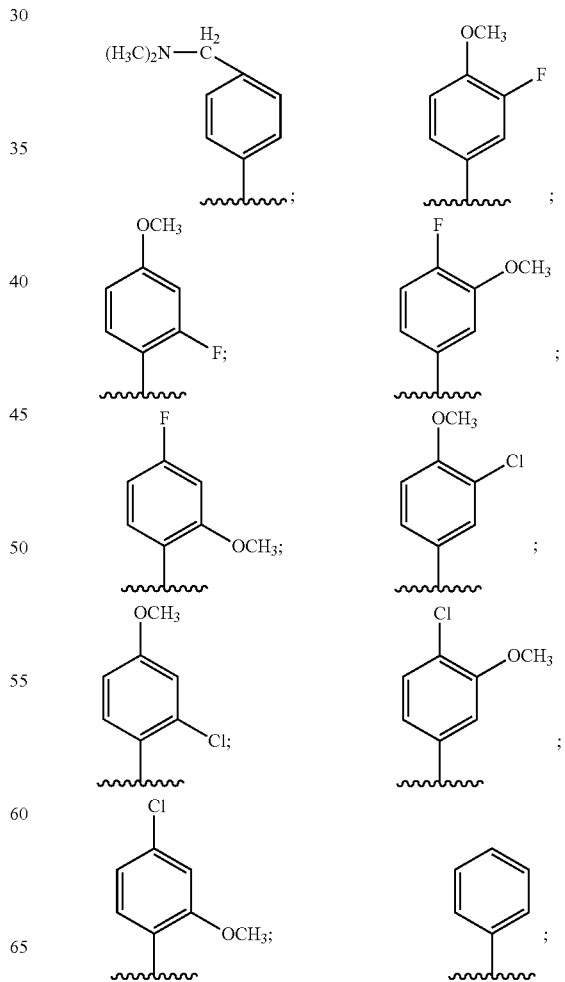

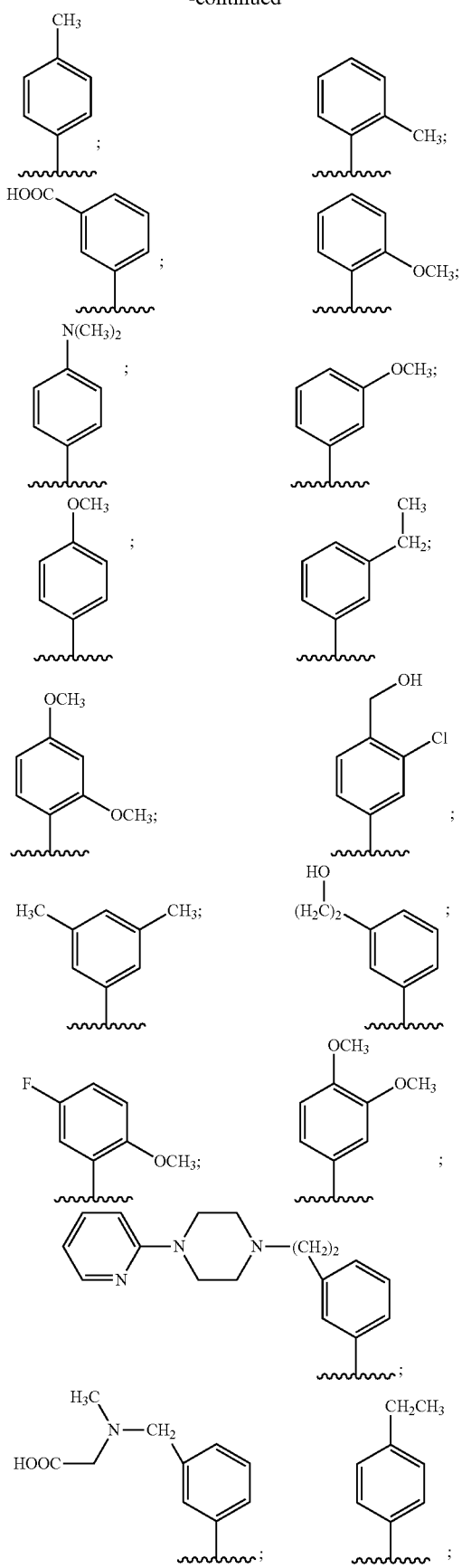
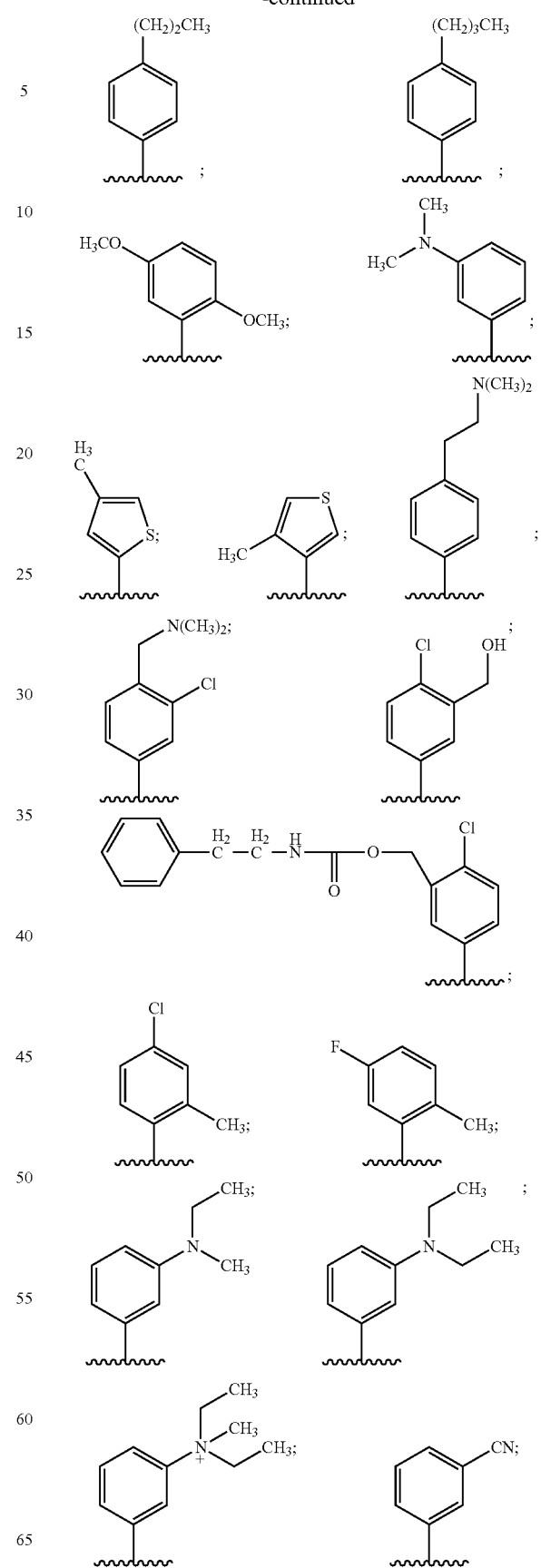

-continued
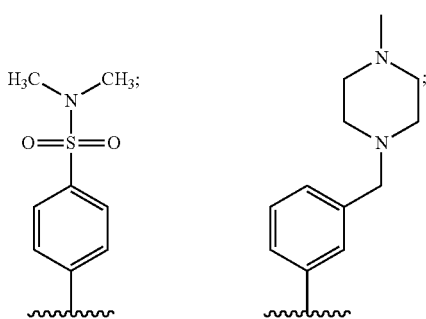
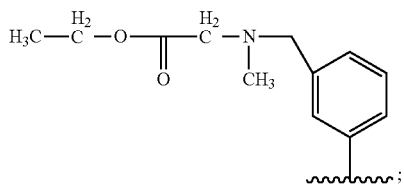
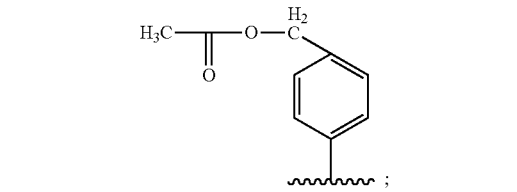
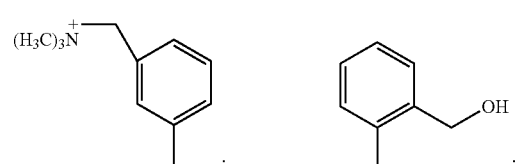
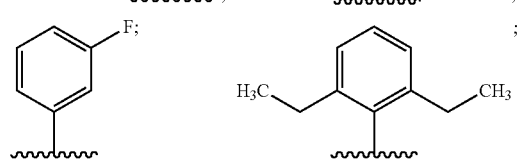
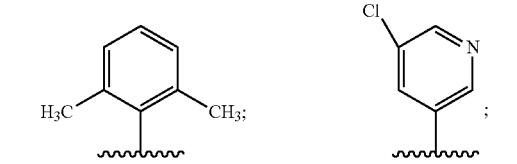
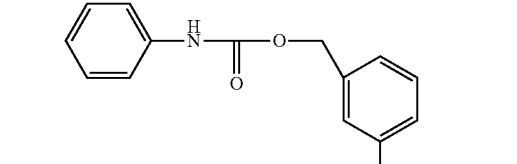
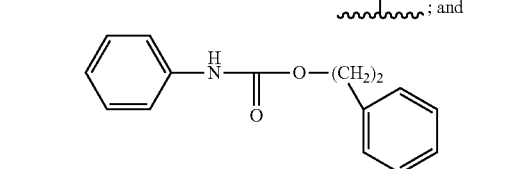
with the proviso that when M is F, R* is not a member selected from:
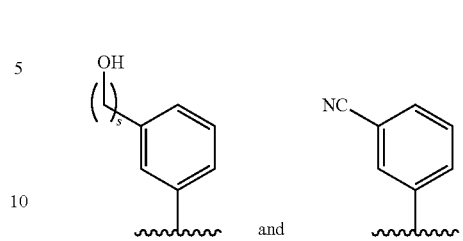
wherein s is 2;
and with the proviso that when M is Cl, R* is not:
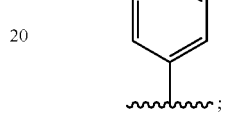
including salts thereof.
3. The compound of claim 1, wherein M is Cl or F.
4. The compound of claim 2, wherein M is F, and R* is a member selected from:
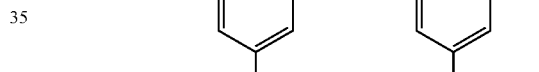

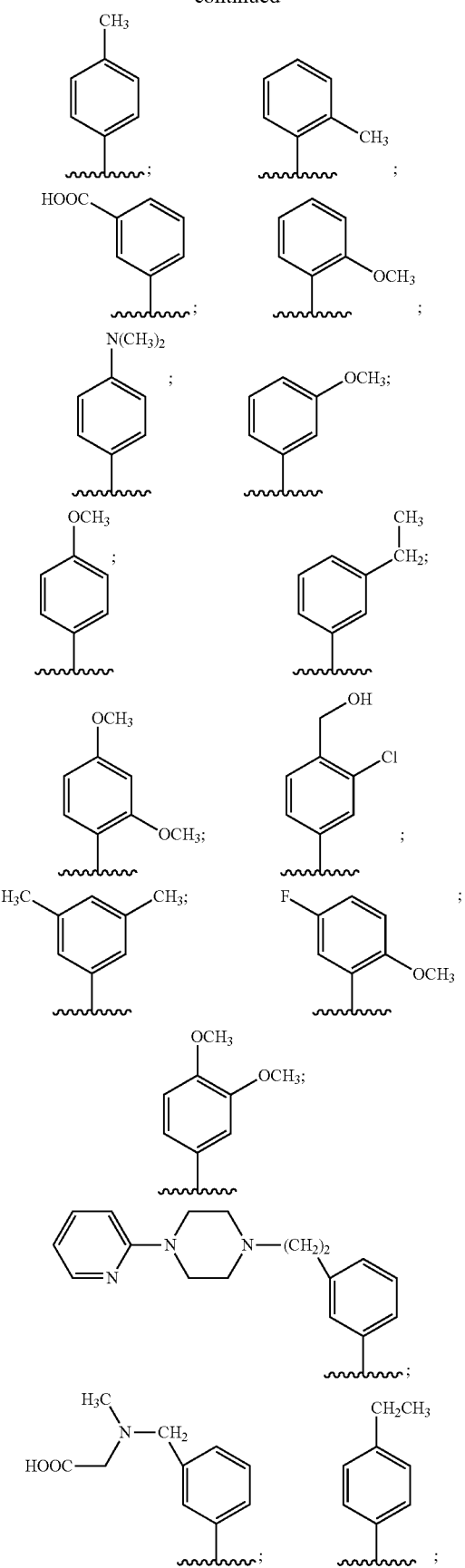
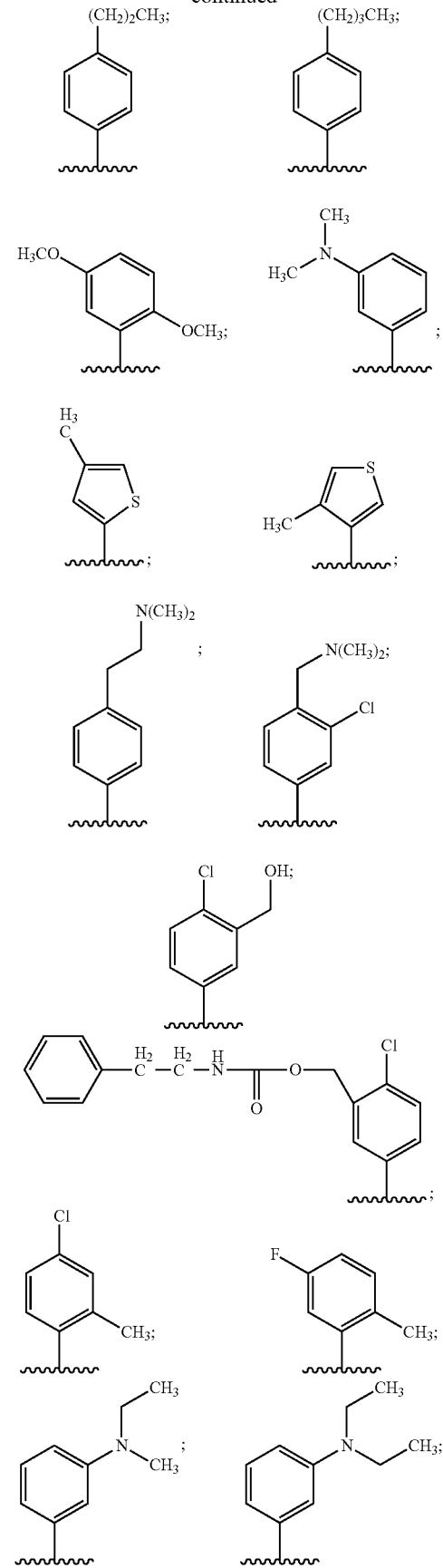

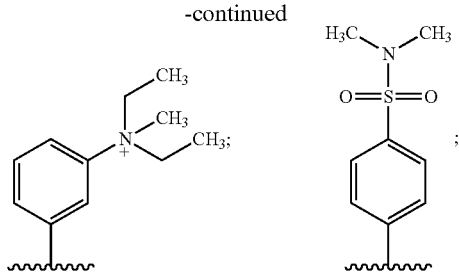
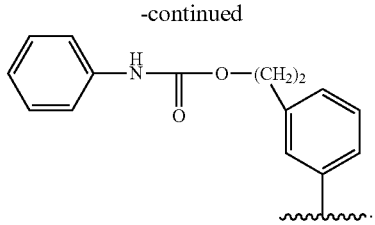
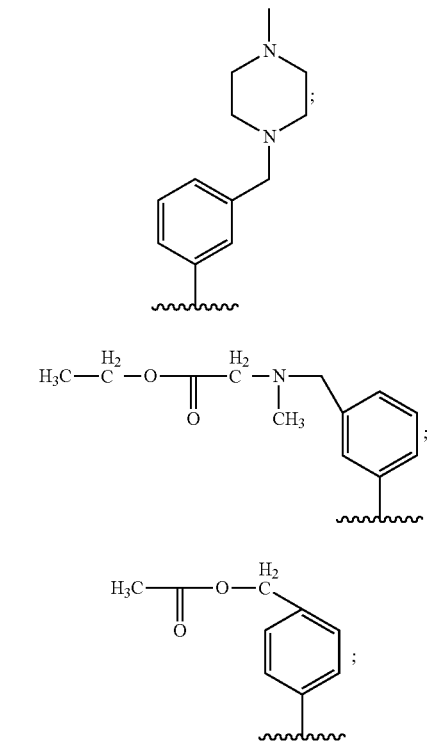
5. The compound of claim 4, wherein R* is a member selected from:
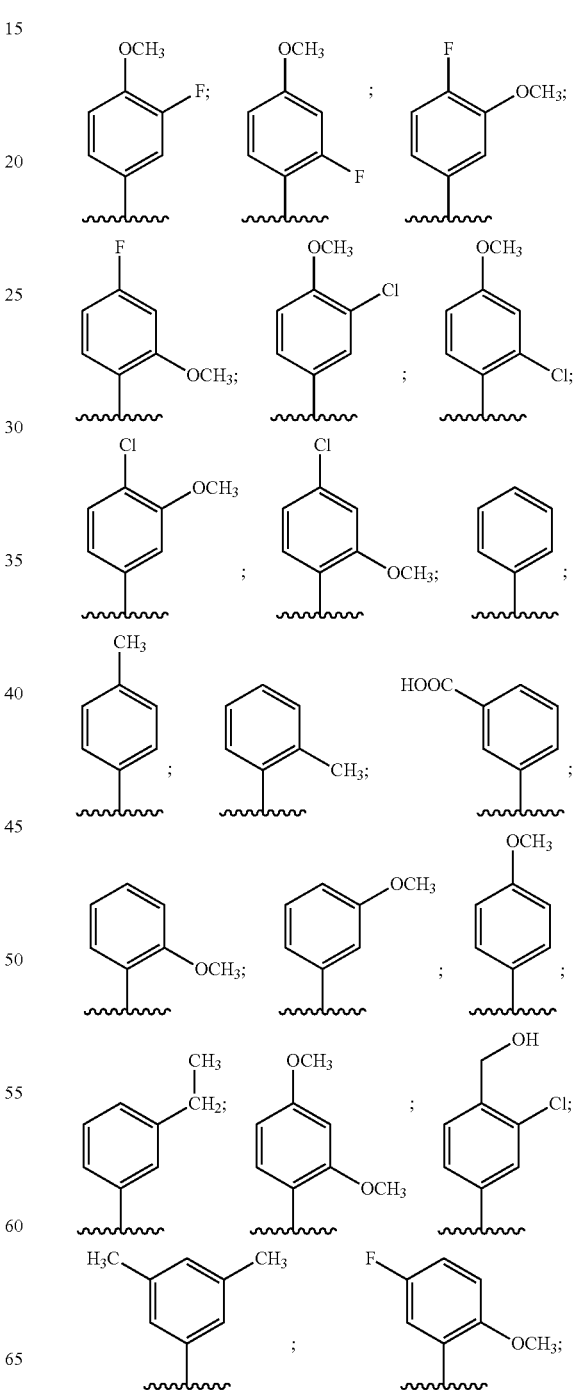
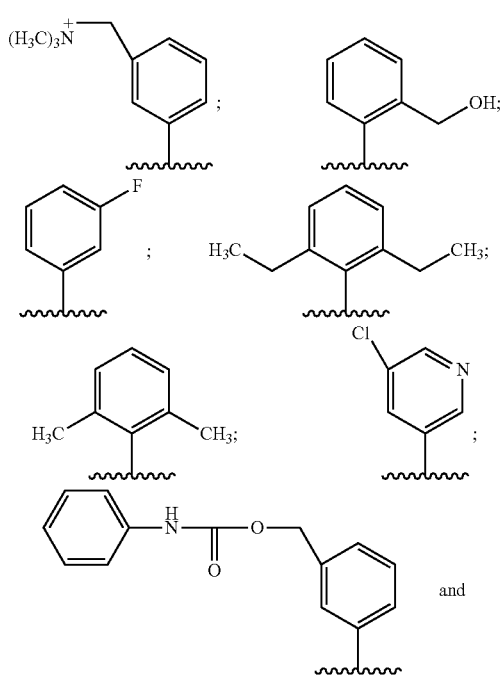
and

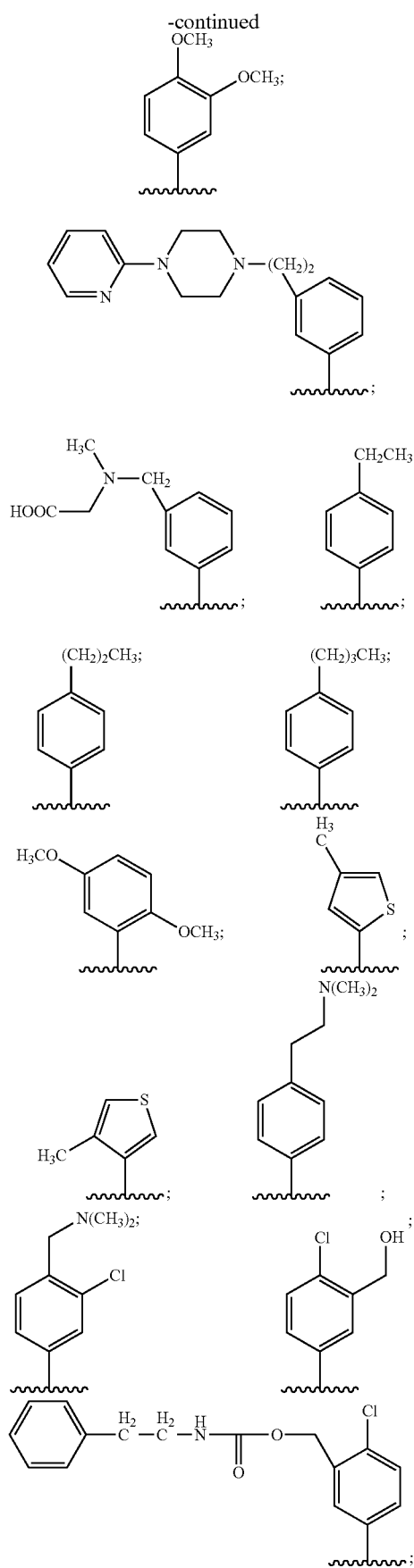
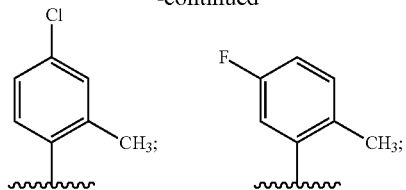
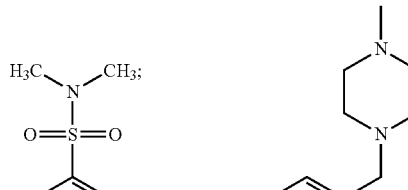
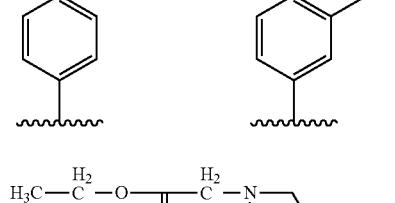
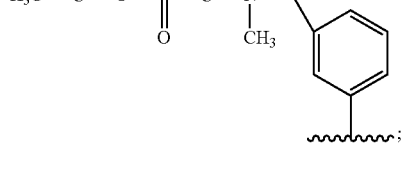
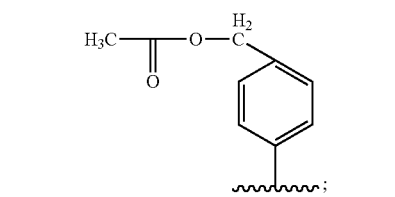
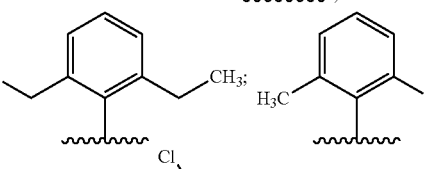
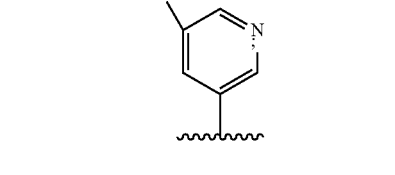
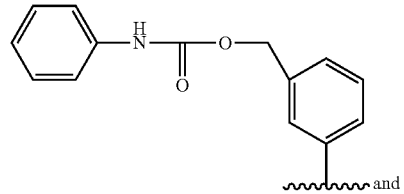
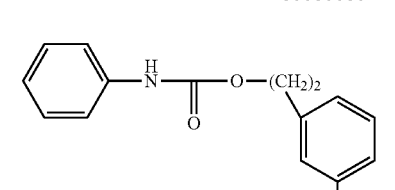

6. A compound of Formula (I)

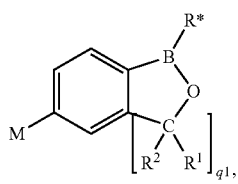

wherein

B is boron;

q1 is an integer selected from 1 to 3;

M is H,

R¹ and R² are members independently selected from H, OH, $NH_2$, SH, CN, $NO_2$, $OSO_2OH$, $OSO_2NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

R* is a member selected from:

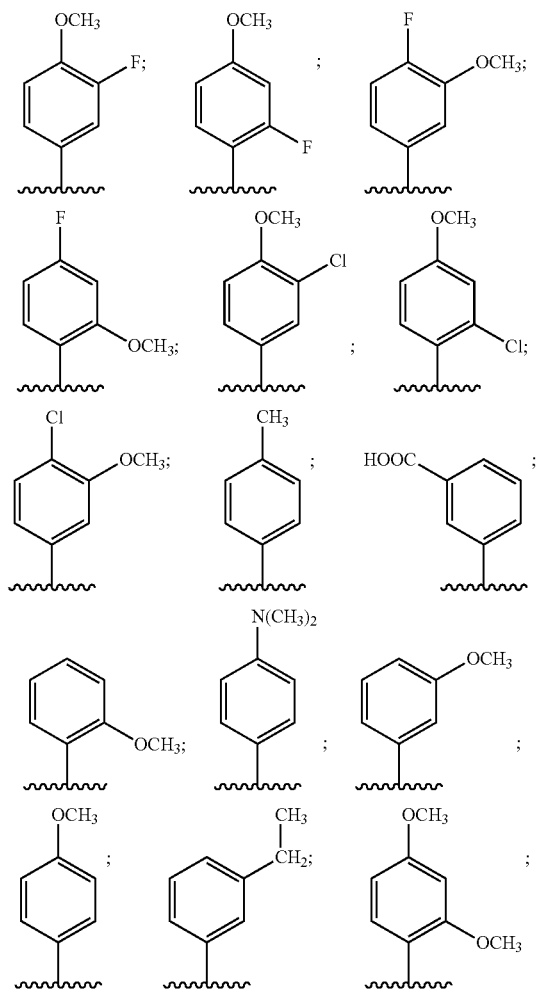

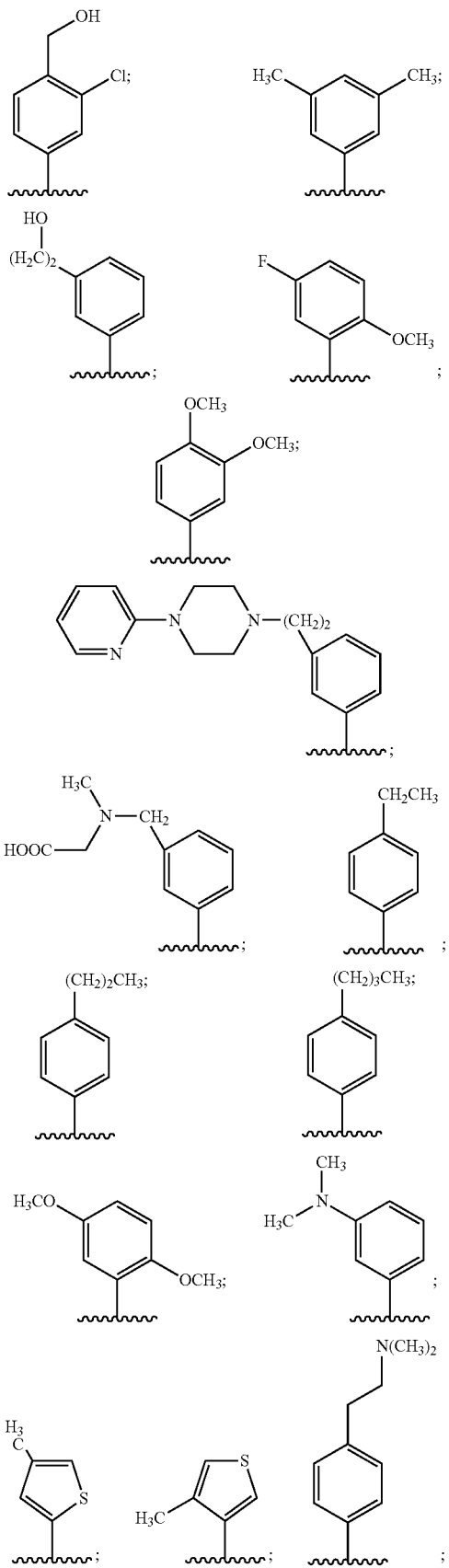

7. A compound of Formula (I)

$$\text{(I)}$$

wherein
- B is boron;
- q1 is an integer selected from 1 to 3;
- M is H,
- $R^1$ and $R^2$ are members independently selected from H, OH, $NH_2$, SH, CN, $NO_2$, $OSO_2OH$, $OSO_2NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;
- R* is a member selected from:

-continued
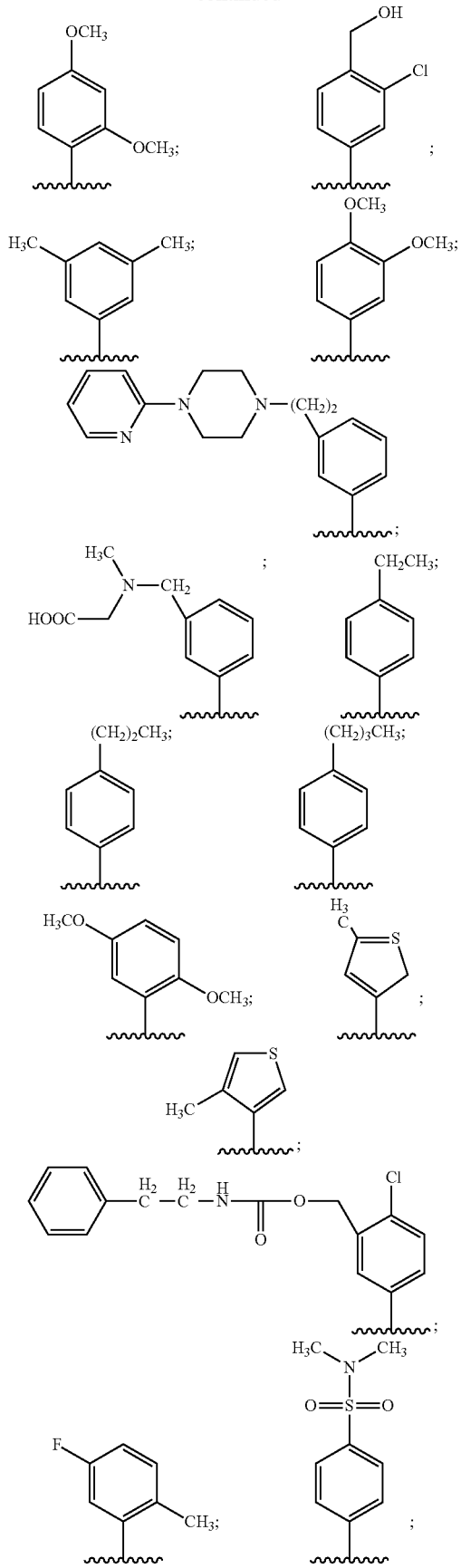
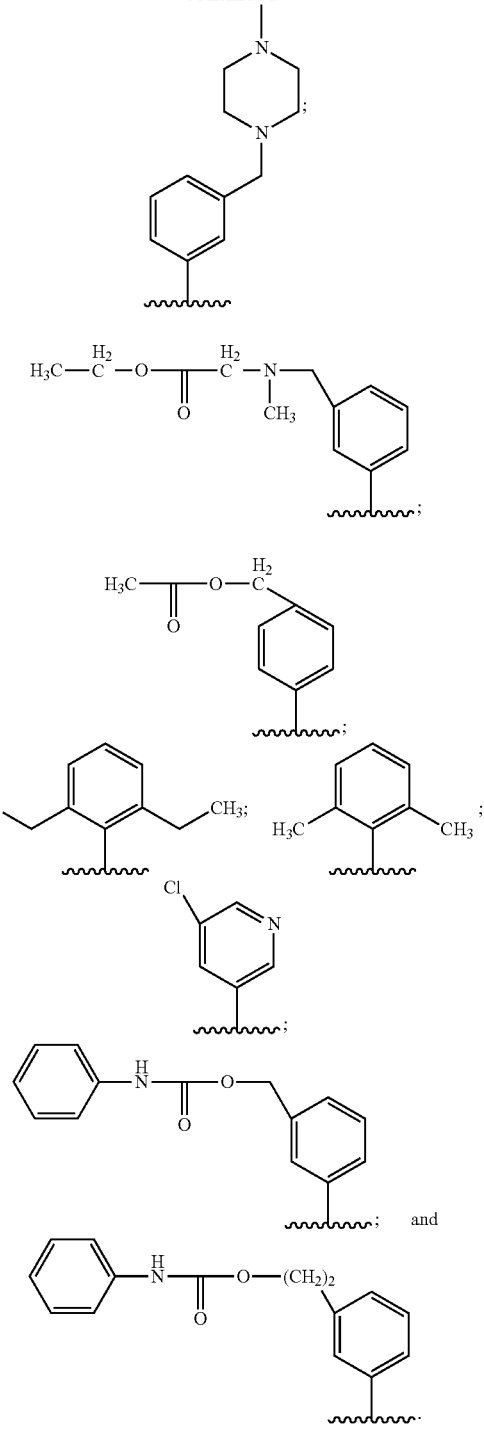
8. A compound of Formula (I)
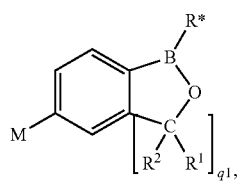

wherein

B is boron;

q1 is an integer selected from 1 to 3;

M is H,

R¹ and R² are members independently selected from H, OH, $NH_2$, SH, CN, $NO_2$, $OSO_2OH$, $OSO_2NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

R* is a member selected from:

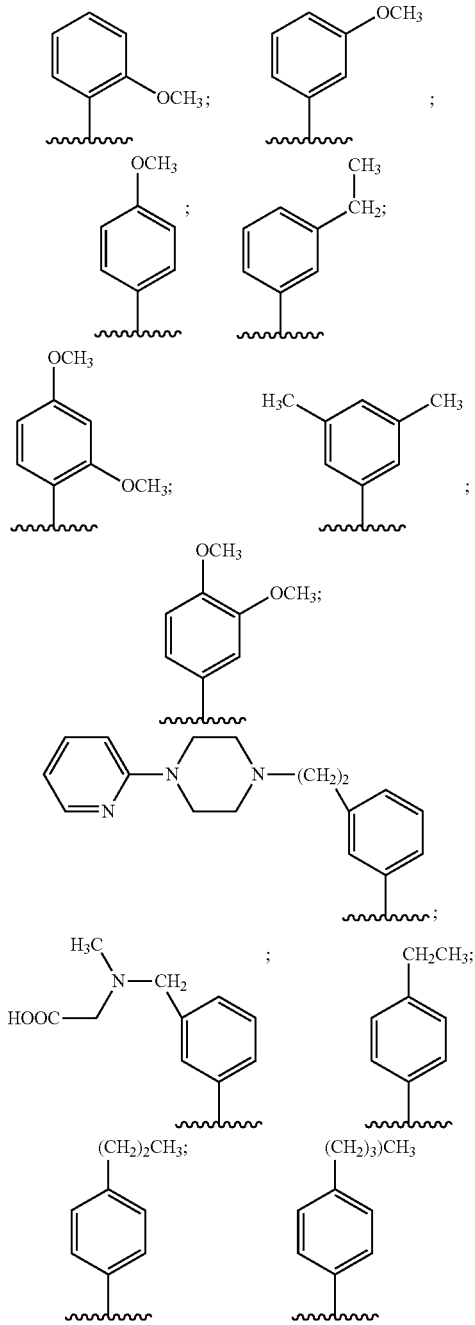

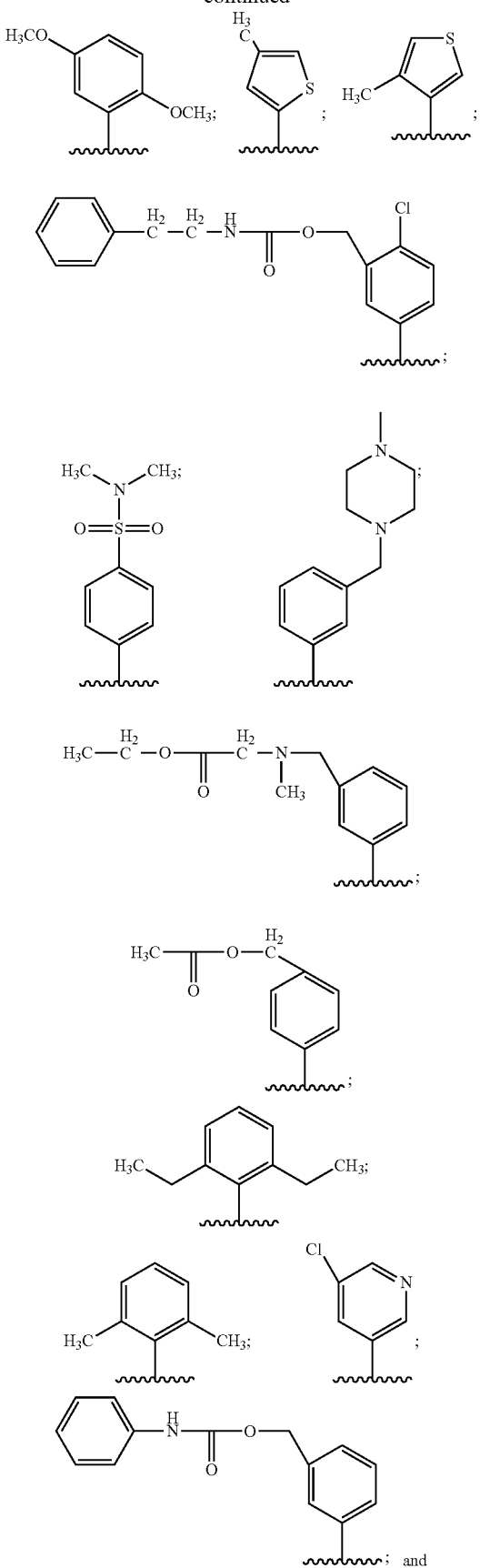

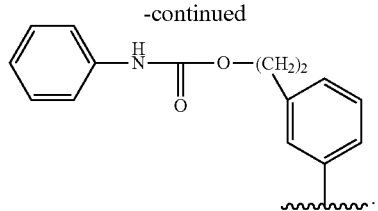

9. A compound of Formula (I)

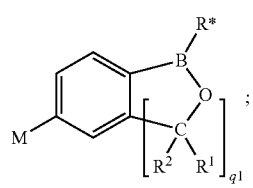

wherein
B is boron;
q1 is an integer selected from 1 to 3;
M is Cl;
R¹ and R² are members independently selected from H, OH, $NH_2$, SH, CN, $NO_2$, $OSO_2OH$, $OSO_2NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and
R* is a member selected from:

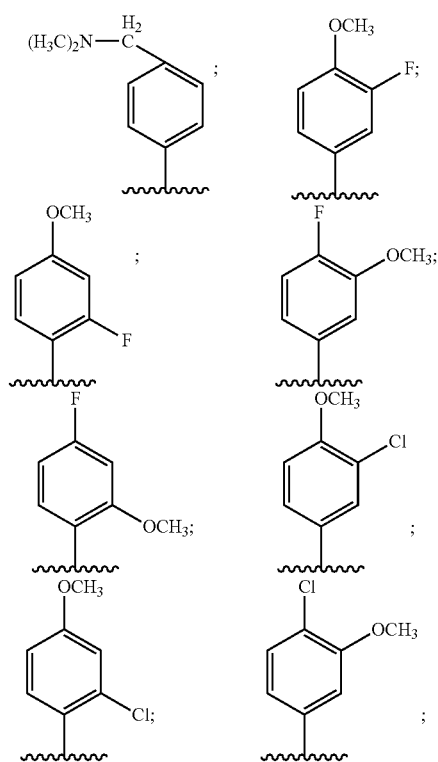

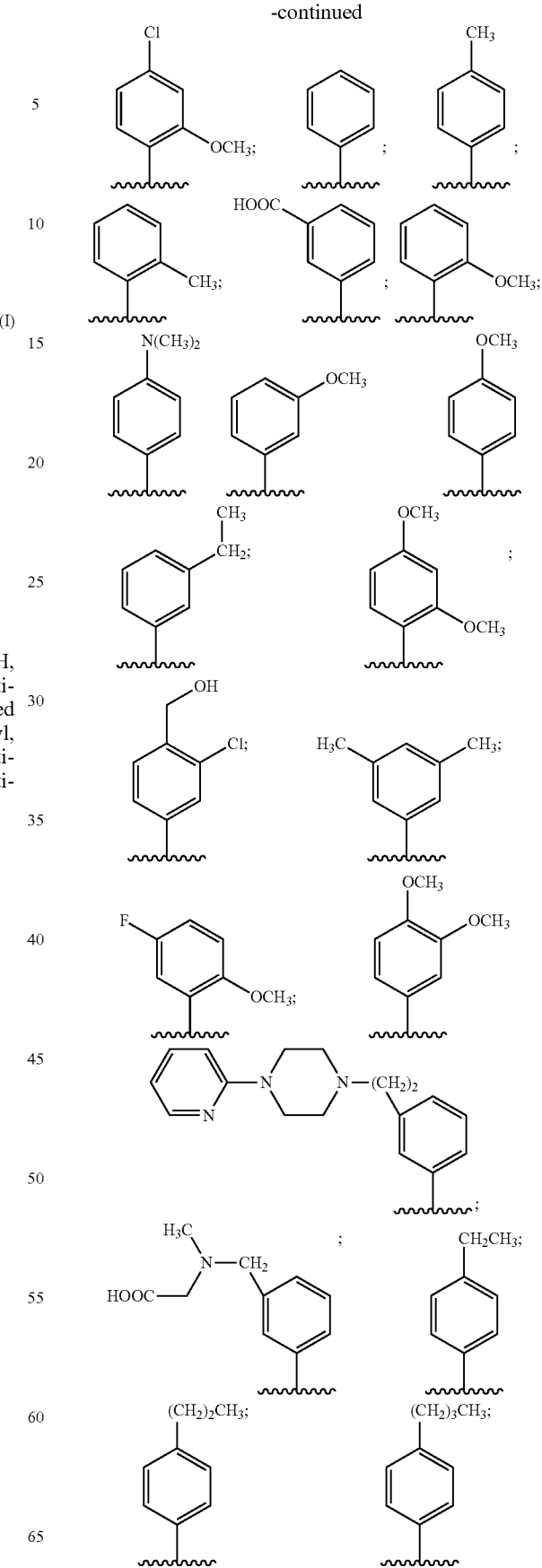

139
-continued
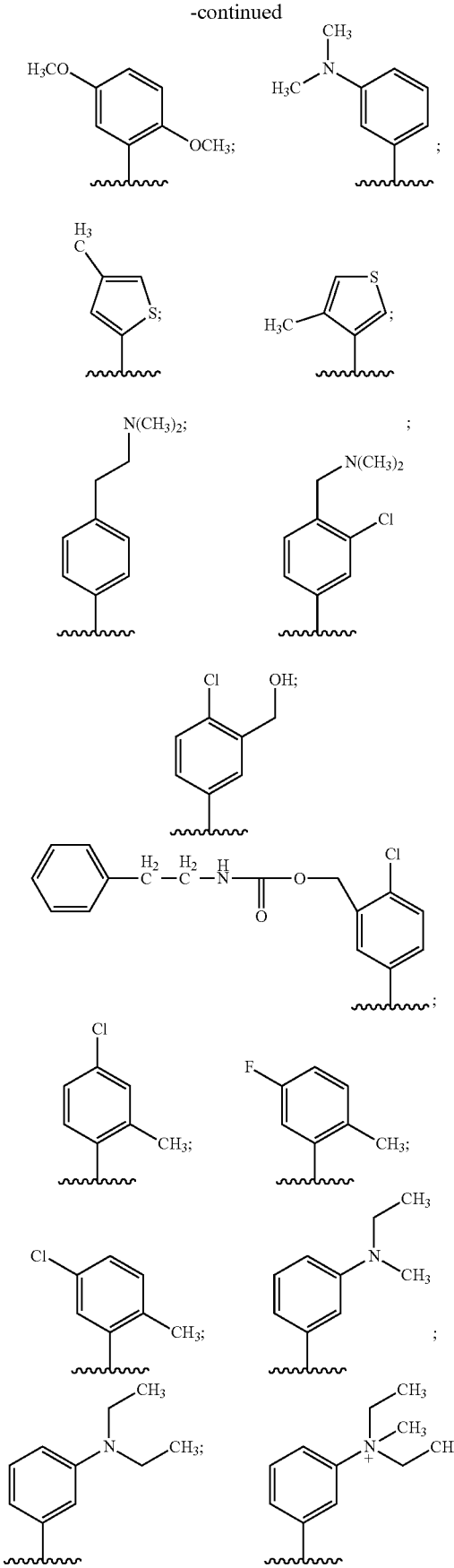
140
-continued
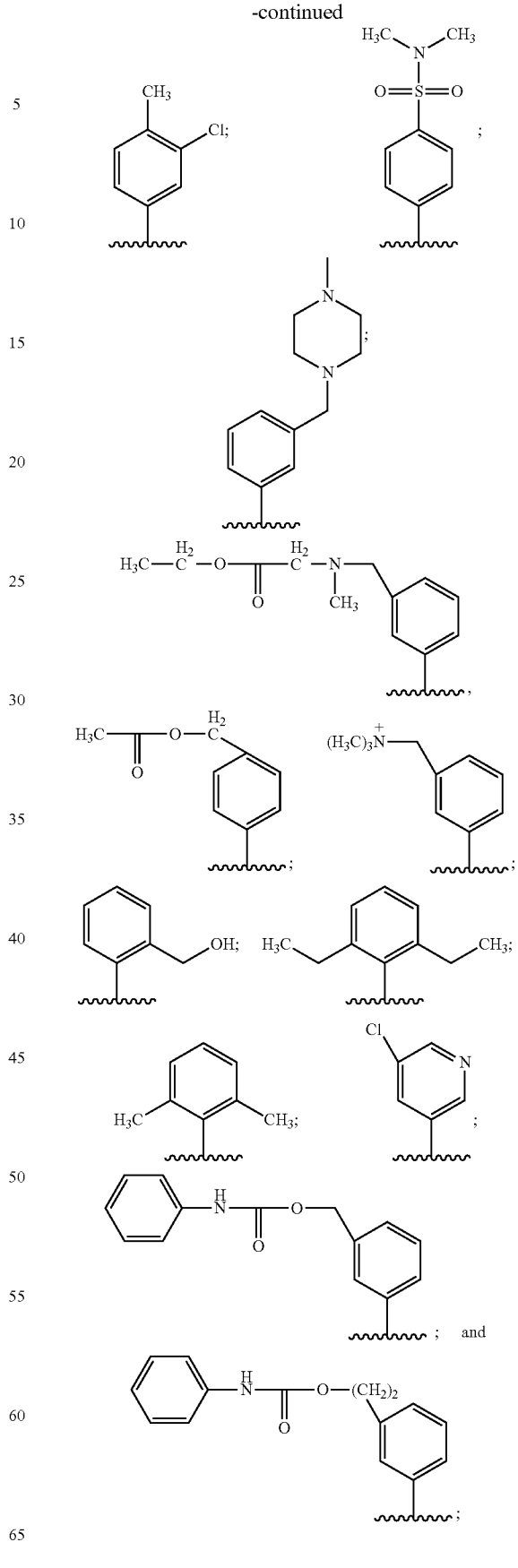
including salts thereof.

10. The compound of claim 9, wherein R* is a member selected from:
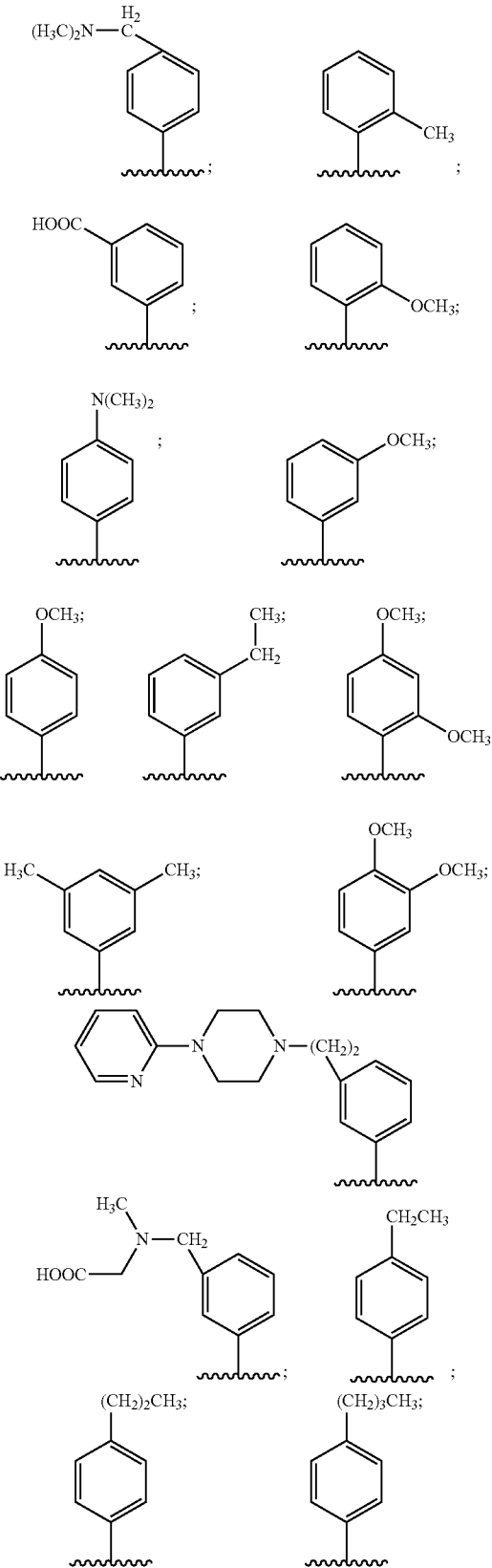
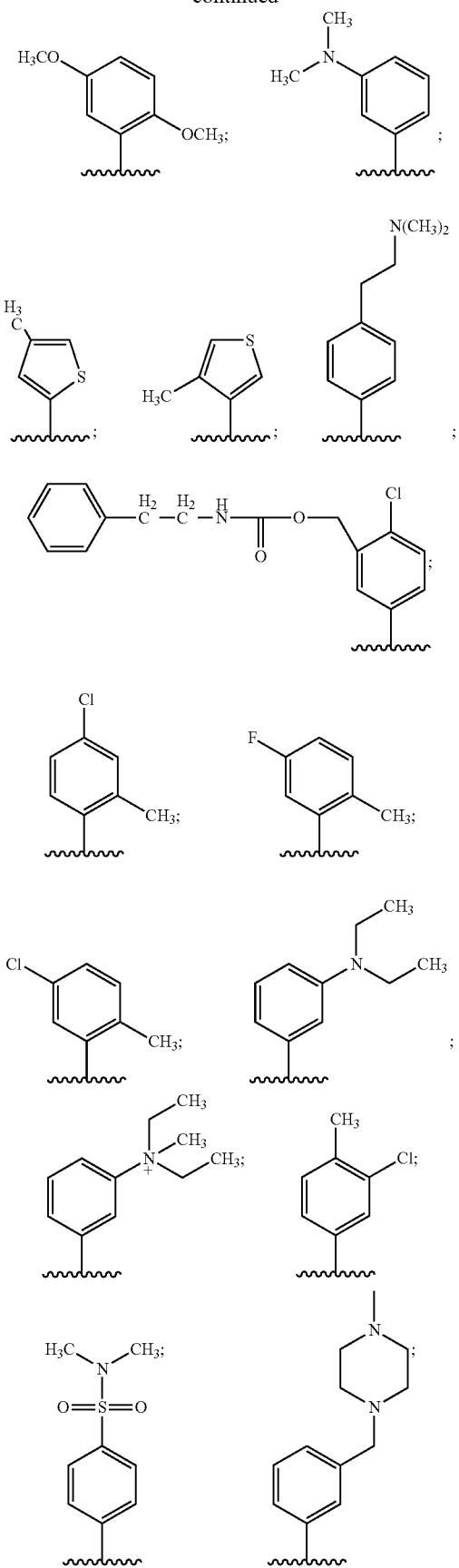

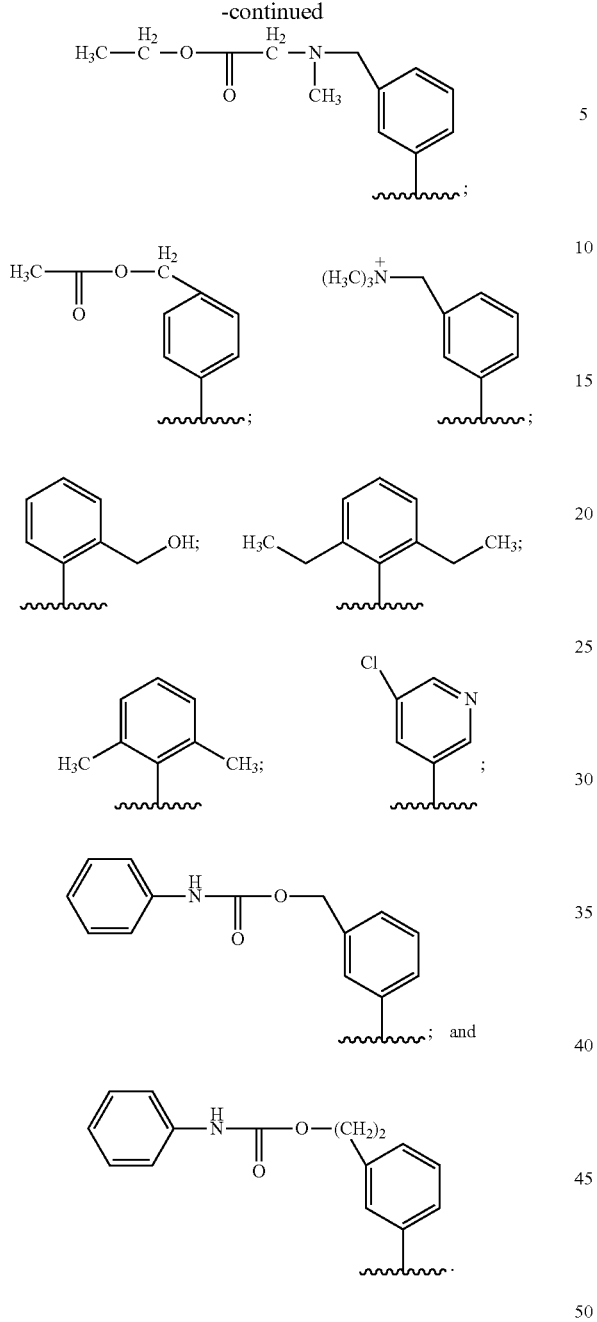
11. A compound of a structure which is a member selected from:
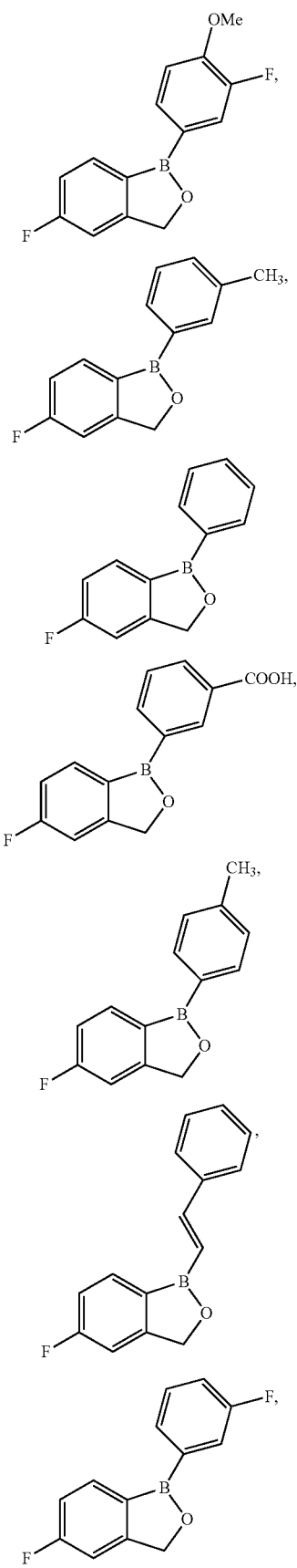

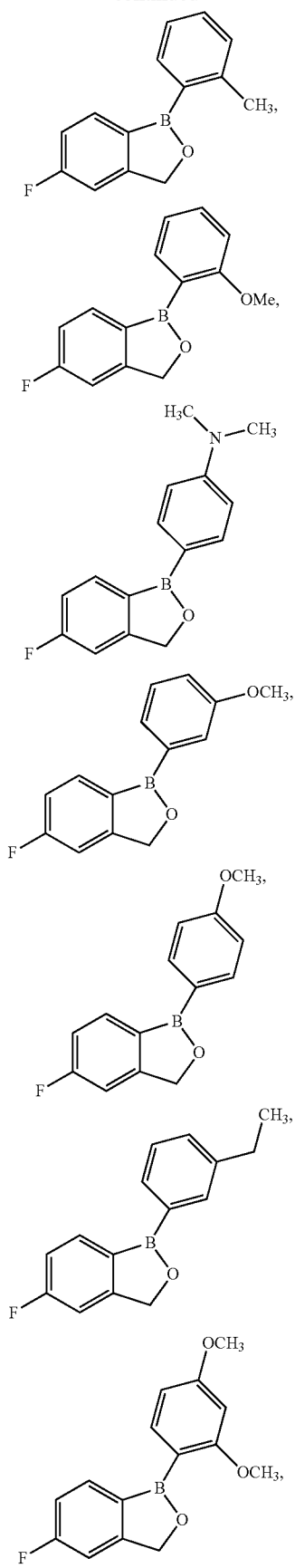
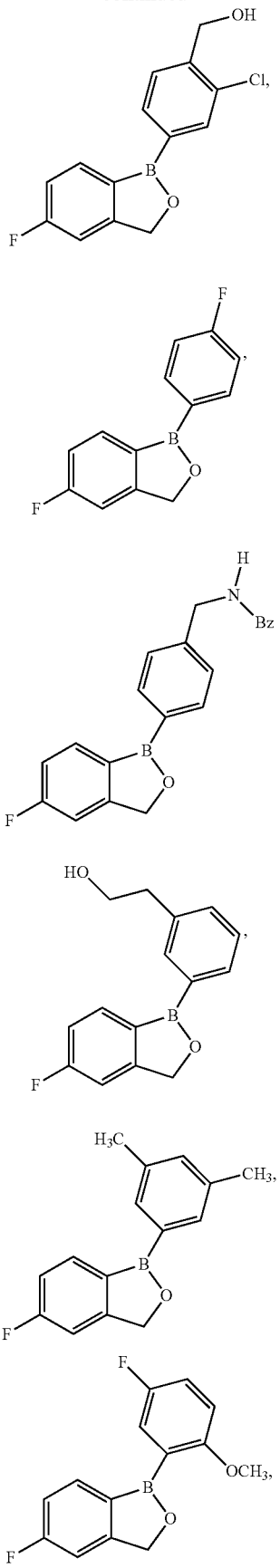

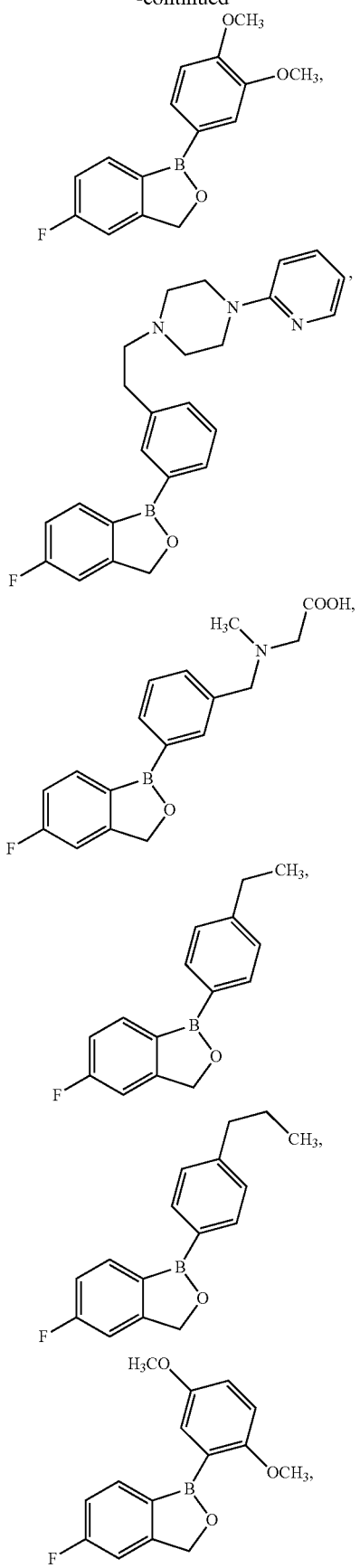
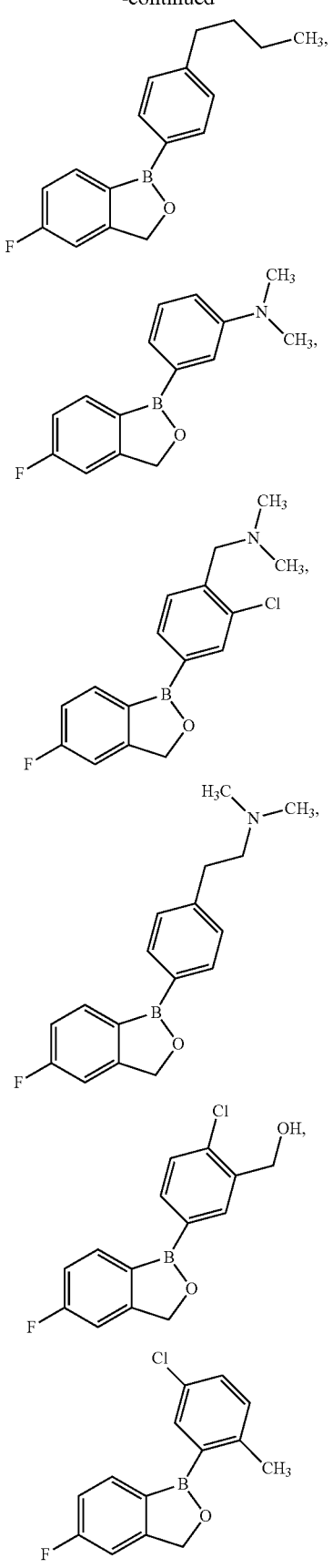

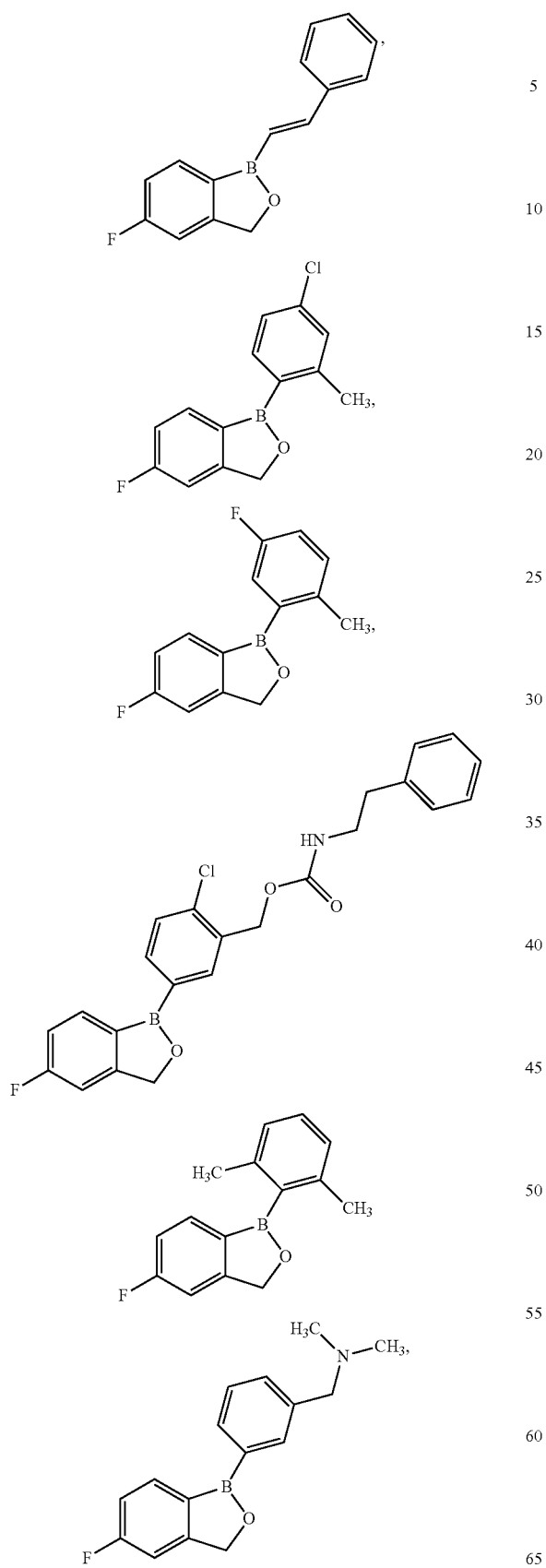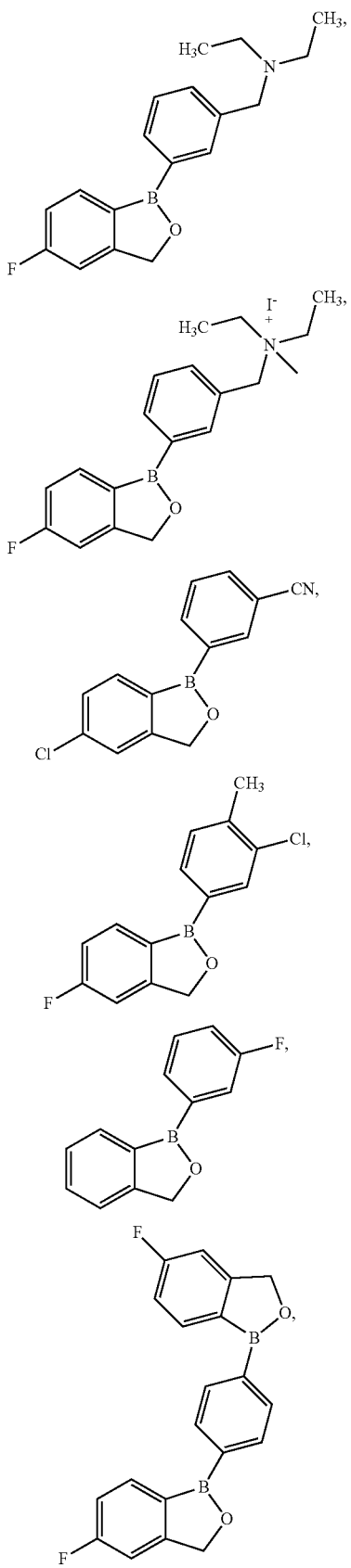

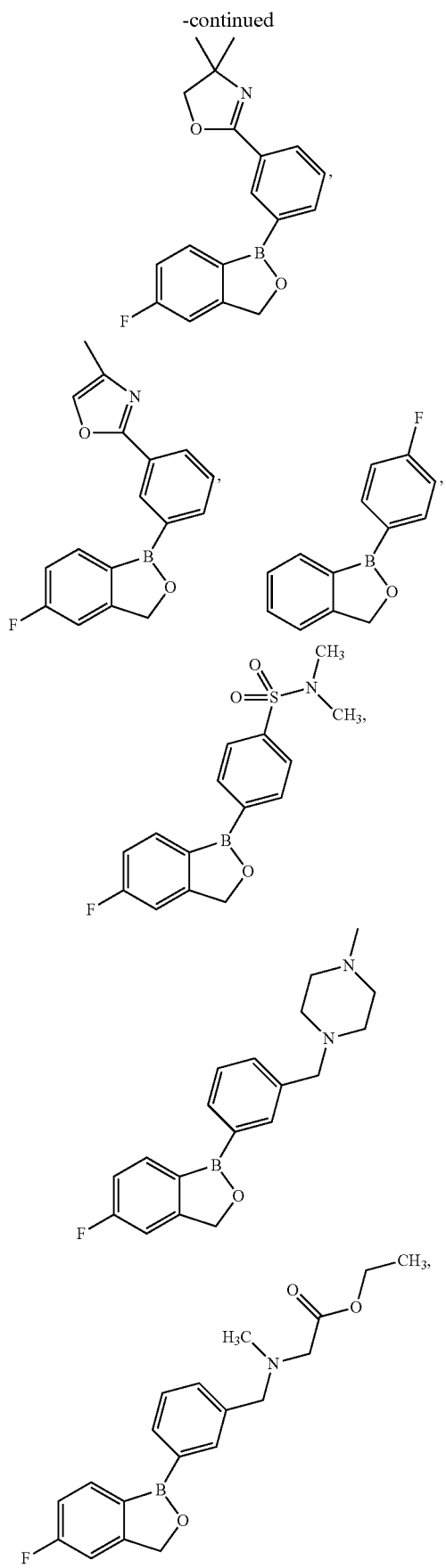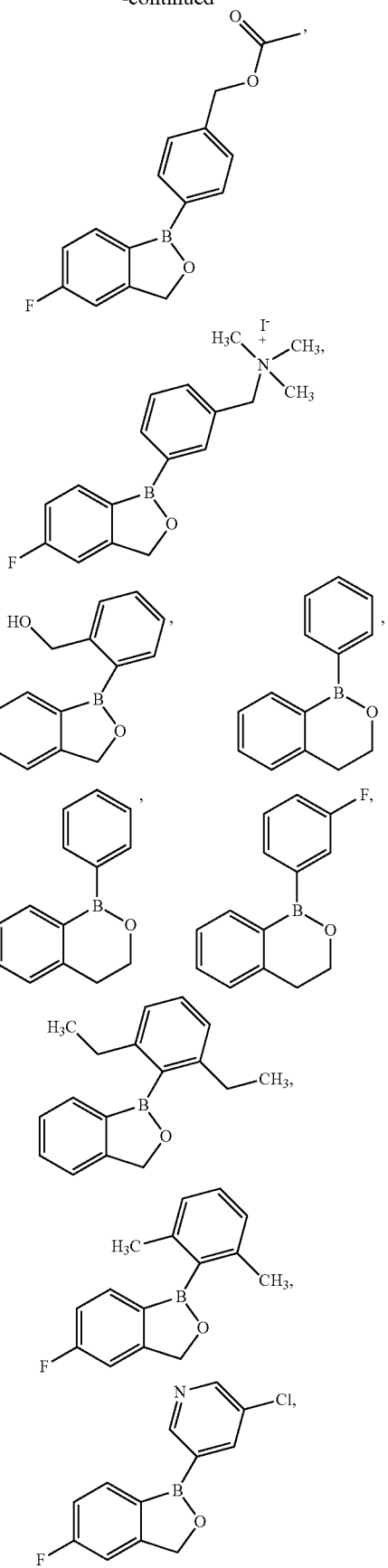

153
-continued
154
-continued
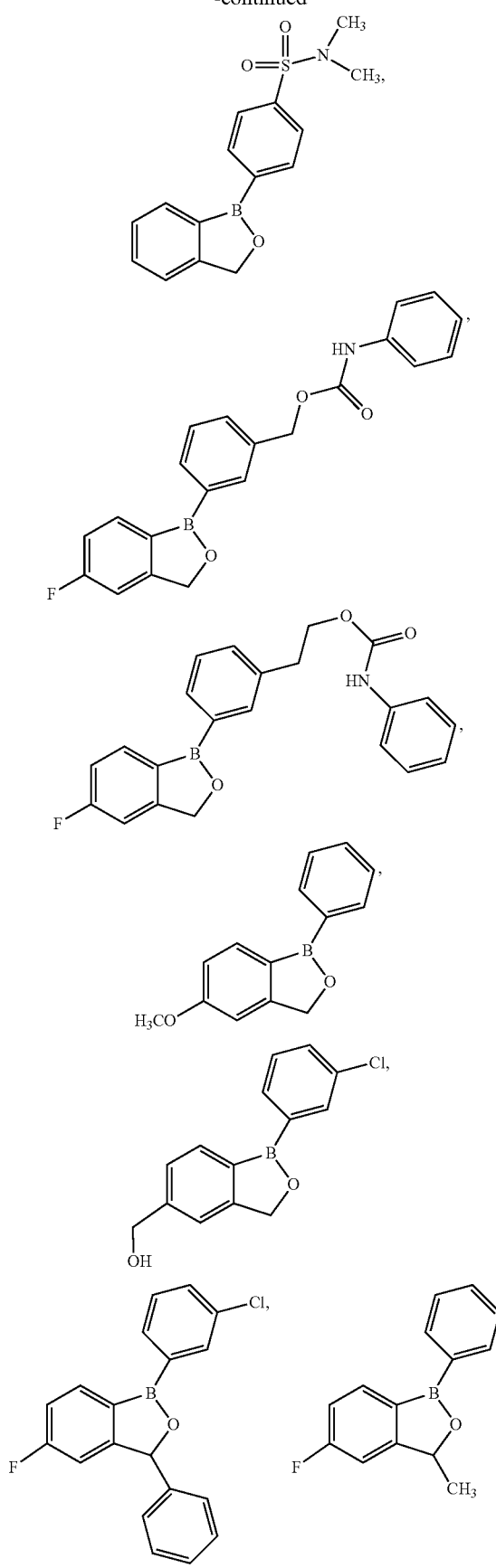
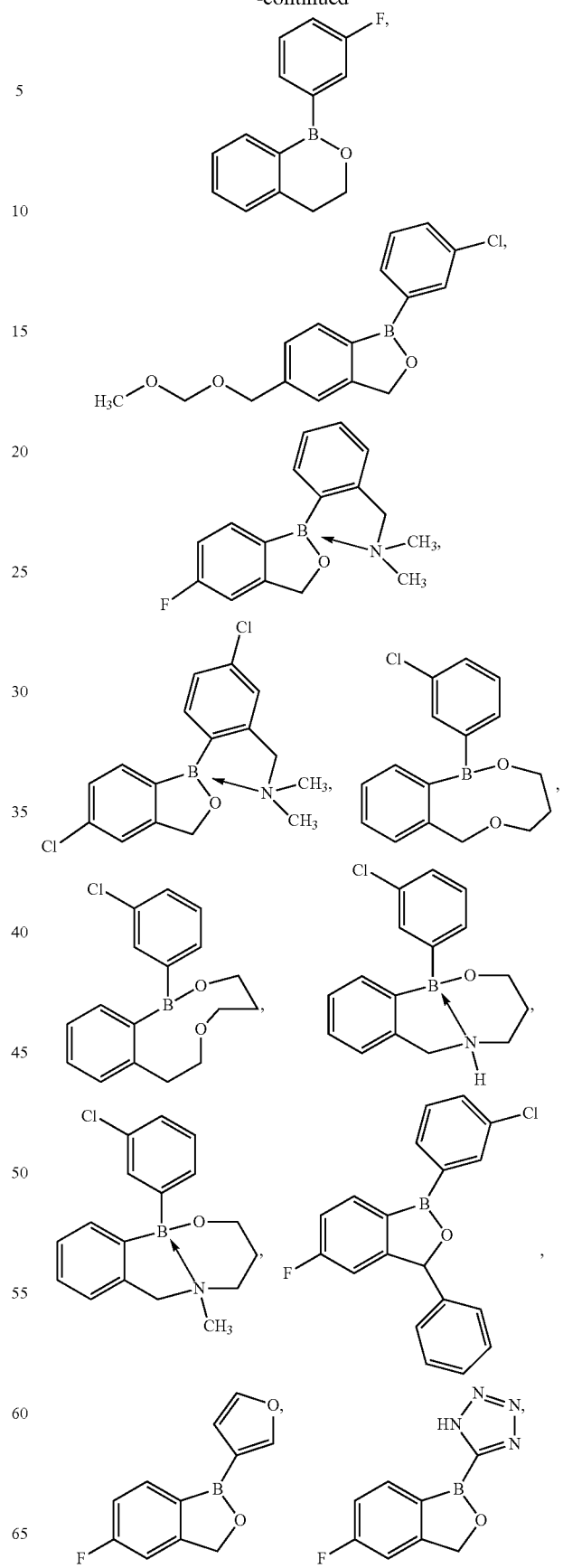

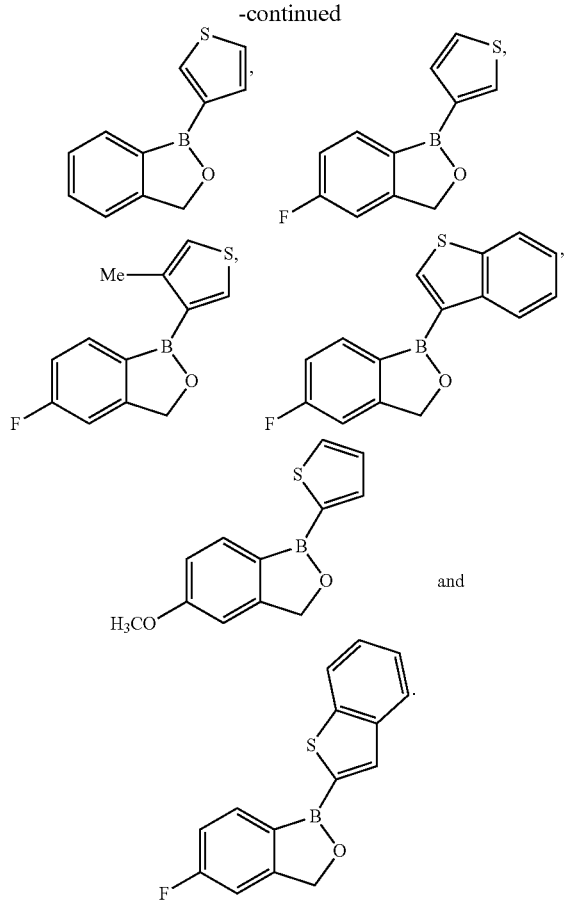

12. A compound of Formula (II)

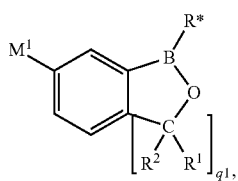

(II)

wherein

B is boron;

q1 is an integer selected from 1 to 3;

$M^1$ is a member selected from halogen, —CH$_2$OH, and —OCH$_3$;

$R^1$ and $R^2$ are members independently selected from H, OH, NH$_2$, SH, CN, NO$_2$, OSO$_2$OH, OSO$_2$NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

R* is a member selected from substituted or unsubstituted aryl, substituted or unsubstituted arylalkyl, substituted or unsubstituted heteroaryl, substituted or unsubstituted heteroarylalkyl, and substituted or unsubstituted vinyl, wherein said aryl has the structure:

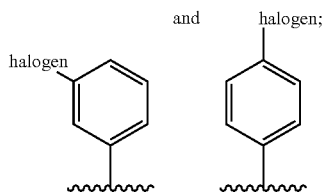

wherein $R^{10}$, $R^{11}$, $R^{12}$, $R^{13}$ and $R^{14}$ are members independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, (CH$_2$)$_t$OH, CO$_2$H, CO$_2$-alkyl, CONH$_2$, CONH-alkyl, CON(alkyl)$_2$, OHSH, S-alkyl, S-aryl, SO-alkyl, SO-aryl, SO$_2$-alkyl, SO$_2$-aryl, SO$_3$H, SCF$_3$, CN, halogen, CF$_3$, NO$_2$, (CH$_2$)$_u$NR$^{22}$R$^{23}$, SO$_2$NH$_2$, OCH$_2$CH$_2$NH$_2$, OCH$_2$CH$_2$NH-alkyl and OCH$_2$CH$_2$N(alkyl)$_2$ wherein t is a member selected from 1, 2 and 3;

u is a member selected from 0, 1 and 2;

$R^{22}$ and $R^{23}$ are members independently selected from H, substituted or unsubstituted alkyl, and substituted or unsubstituted alkanoyl; and with the proviso that when $M^1$ is F, R* is not a member selected from:

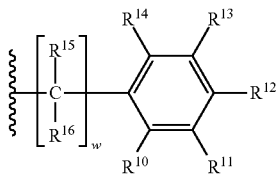

including salts thereof.

13. The compound of claim 12 wherein R* is substituted or unsubstituted arylalkyl.

14. The compound of claim 13 wherein said arylalkyl has the structure:

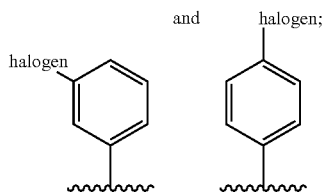

wherein $R^{10}$, $R^{11}$, $R^{12}$, $R^{13}$ and $R^{14}$ are members independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, (CH$_2$)$_t$OH, CO$_2$H, CO$_2$-alkyl, CONH$_2$, CONH-alkyl, CON(alkyl)$_2$, OH, SH, S-alkyl, S-aryl, SO-alkyl, SO-aryl, SO$_2$-alkyl, SO$_2$-aryl, SO$_3$H, SCF$_3$, CN, halogen, CF$_3$, NO$_2$, (CH$_2$)$_u$NR$^{22}$R$^{23}$, SO$_2$NH$_2$, OCH$_2$CH$_2$NH$_2$, OCH$_2$CH$_2$NH-alkyl and OCH$_2$CH$_2$N(alkyl)$_2$;

wherein
t is an integer selected from 1, 2 and 3;
u is a member selected from 0, 1 and 2;
$R^{22}$ and $R^{23}$ are members independently selected from H, substituted or unsubstituted alkyl, and substituted or unsubstituted alkanoyl;
$R^{15}$ and $R^{16}$ are members independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_3H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$;
w is a member selected from 1 to 6.

15. The compound of claim 12 wherein R* is substituted or unsubstituted heteroaryl.

16. The compound of claim 15 wherein said heteroaryl has a structure which is a member selected from:

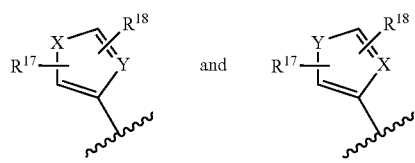

wherein
X is a member selected from CH=CH, N=CH, $NR^{19}$, O and S;
wherein
$R^{19}$ is a member selected from H, substituted or unsubstituted alkyl, substituted or unsubstituted aryl and substituted or unsubstituted arylalkyl;
Y is a member selected from CH and N; and wherein at least one of X and Y is or includes a heteroatom;
$R^{17}$ and $R^{18}$ are members independently selected from H, substituted or unsubstituted alkyl, substituted or unsubstituted aryl, substituted or unsubstituted arylalkyl, $(CH^2)_vOH$, $(CH_2)_wNR^{24}R^{25}$, $CO_2H$, $CO_2$-alkyl, $CONH_2$, S-alkyl, S-aryl, SO-alkyl, SO-aryl, $SO_2$-alkyl, $SO_2$-aryl, $SO_3H$, $SCF_3$, CN, halogen, $CF_3$ and $NO_2$;
wherein
$R^{24}$ and $R^{25}$ are members independently selected from hydrogen, substituted or unsubstituted alkyl and substituted or unsubstituted alkanoyl;
v is a member selected from 1, 2 and 3; and
w is a member selected from 0, 1, 2 and 3.

17. A composition comprising the compound of claim 12 and a pharmaceutically acceptable carrier.

18. The compound of claim 12, wherein R* is a member selected from:

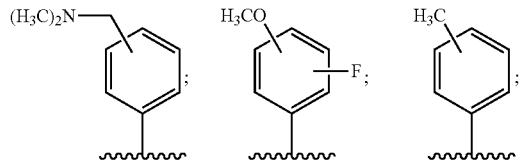

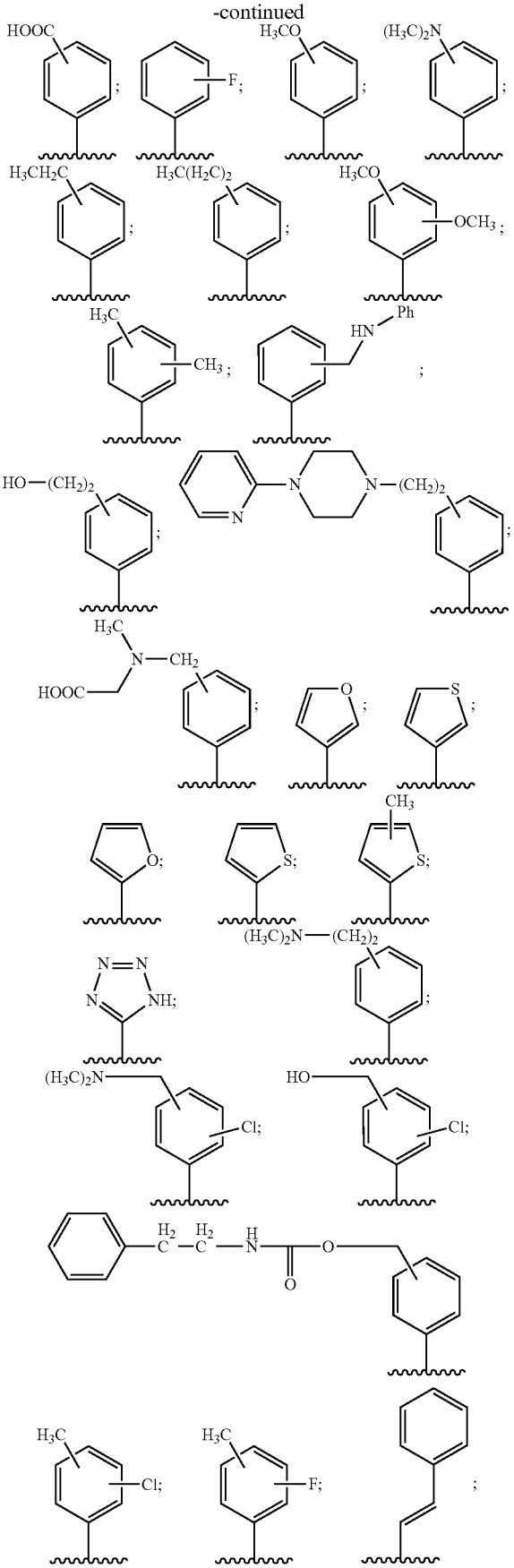

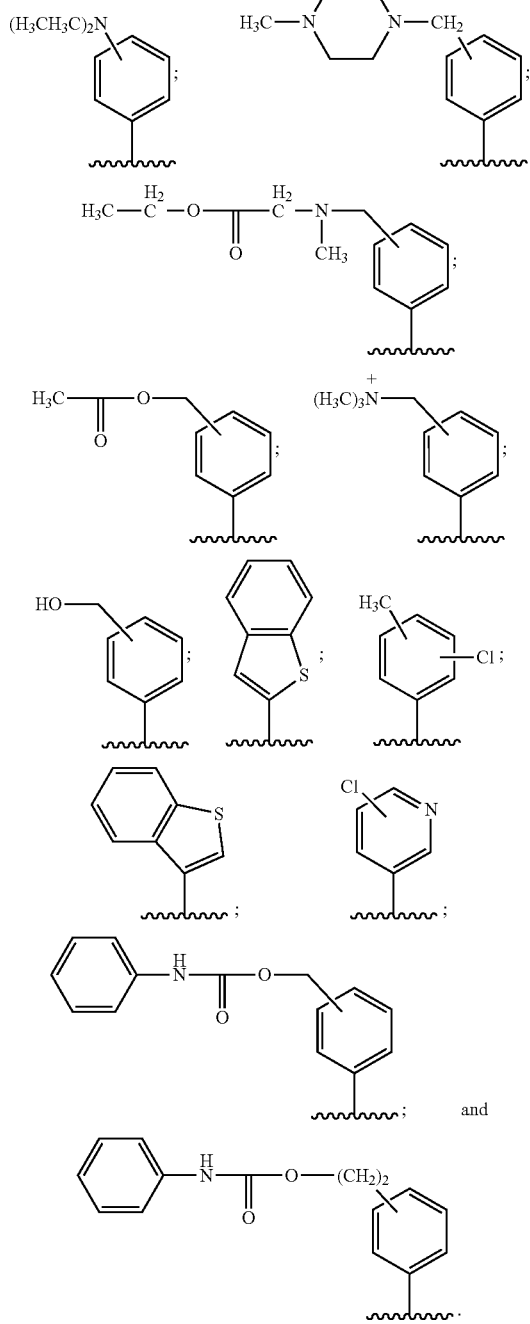
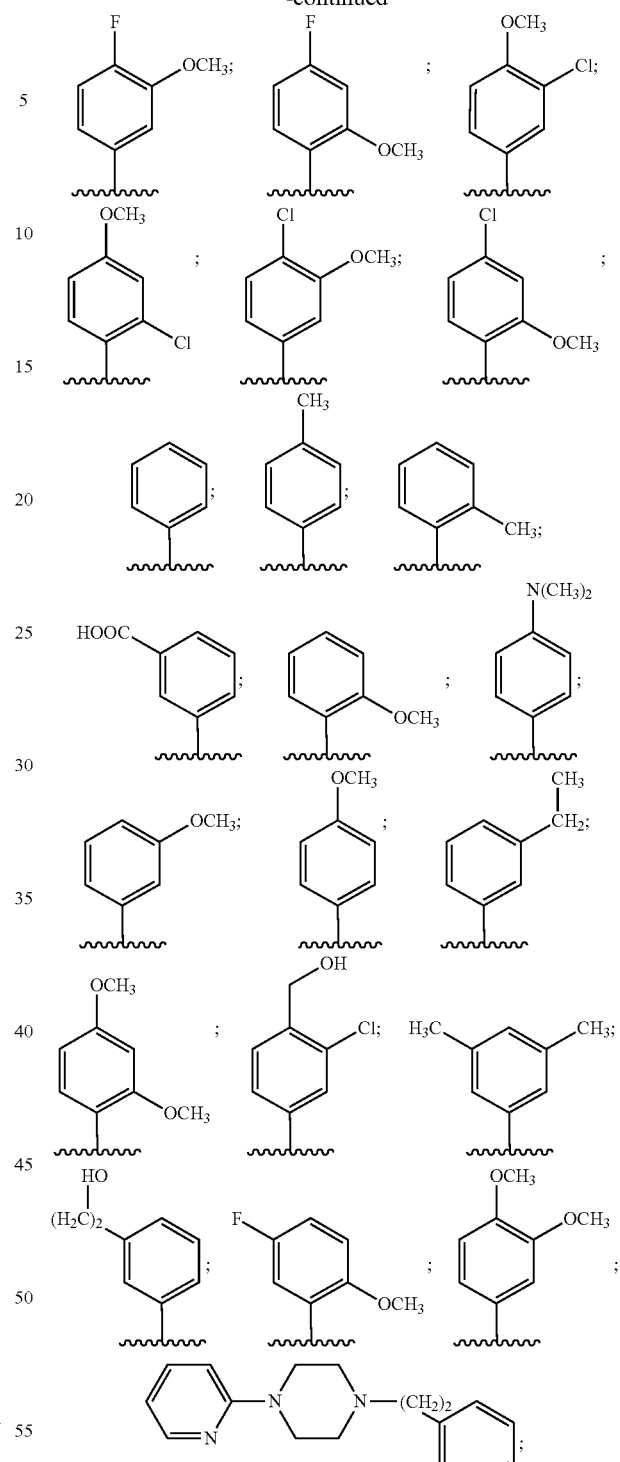
19. The compound of claim 12, wherein R* is a member selected from
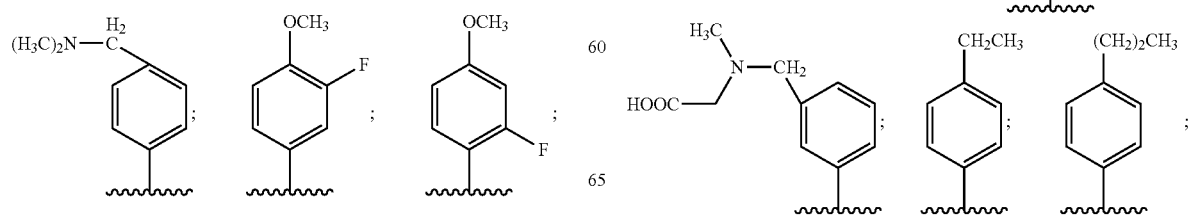

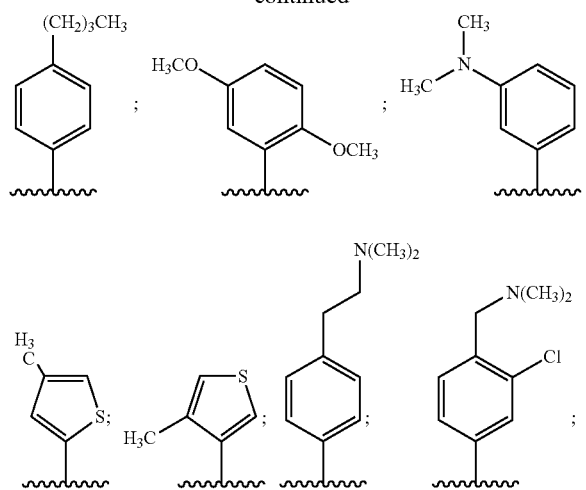
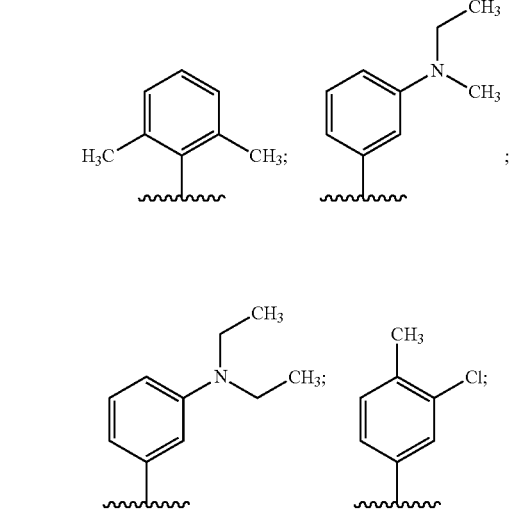
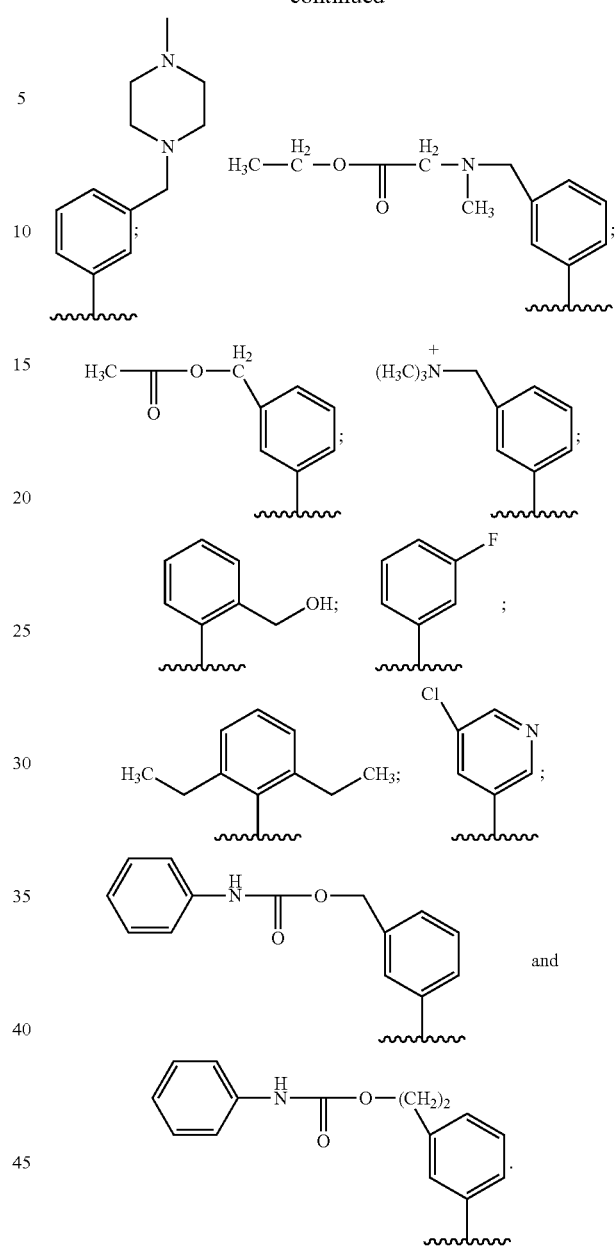
20. The compound of claim 12, wherein $M^1$ is Cl or F, and R* is a member selected from:
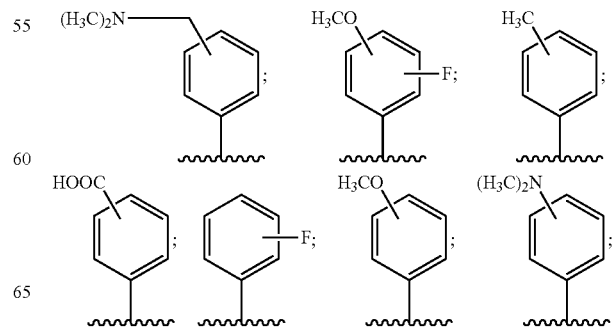

-continued
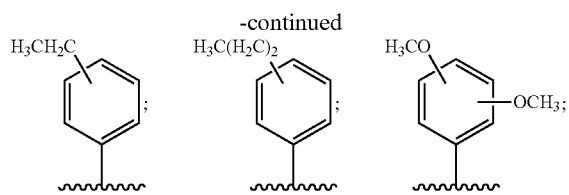
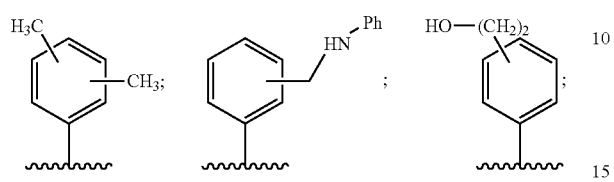
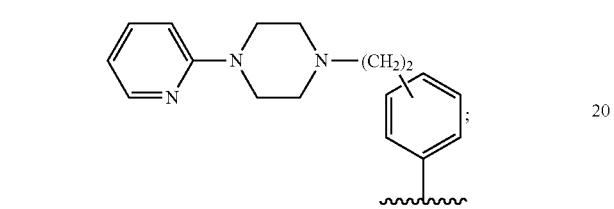
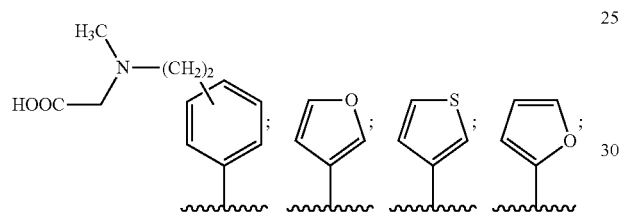
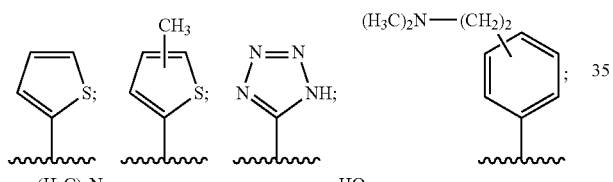
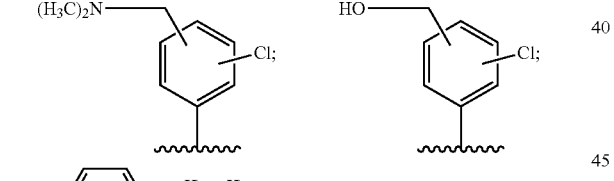
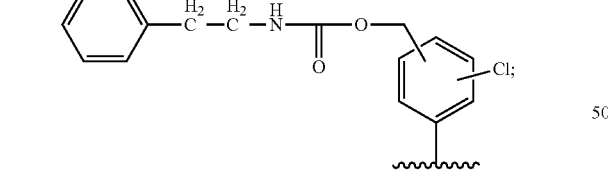
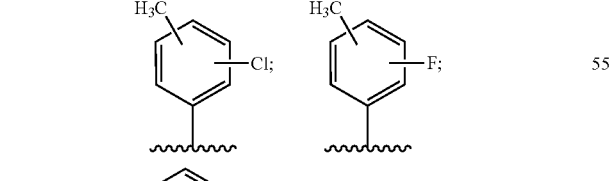
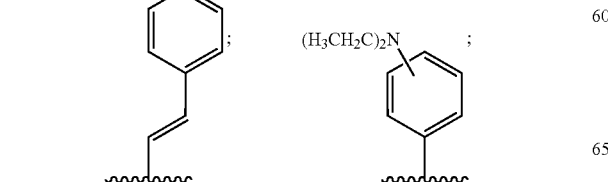
-continued
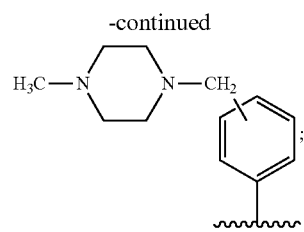
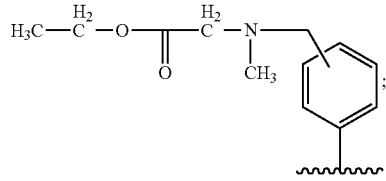
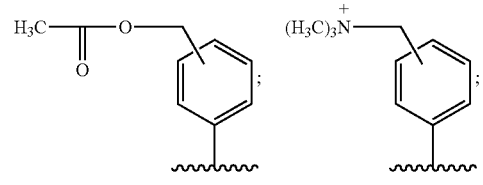
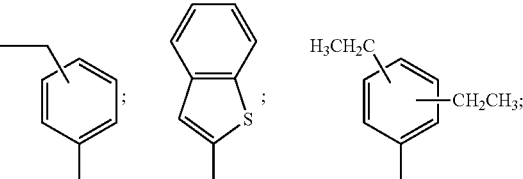
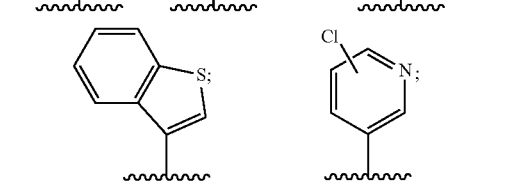
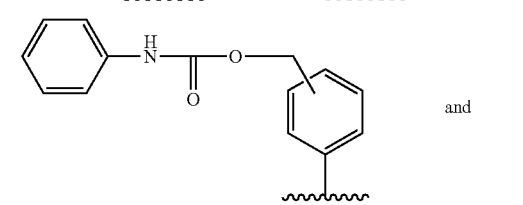
and
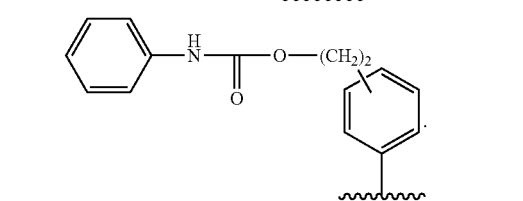
21. The compound of claim 12, wherein $M^1$ is F, R* is a member selected from:
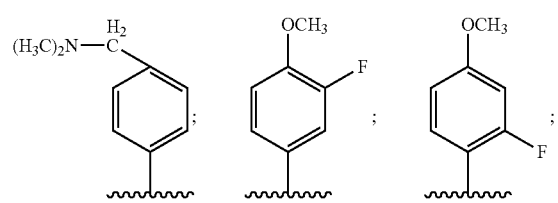

-continued
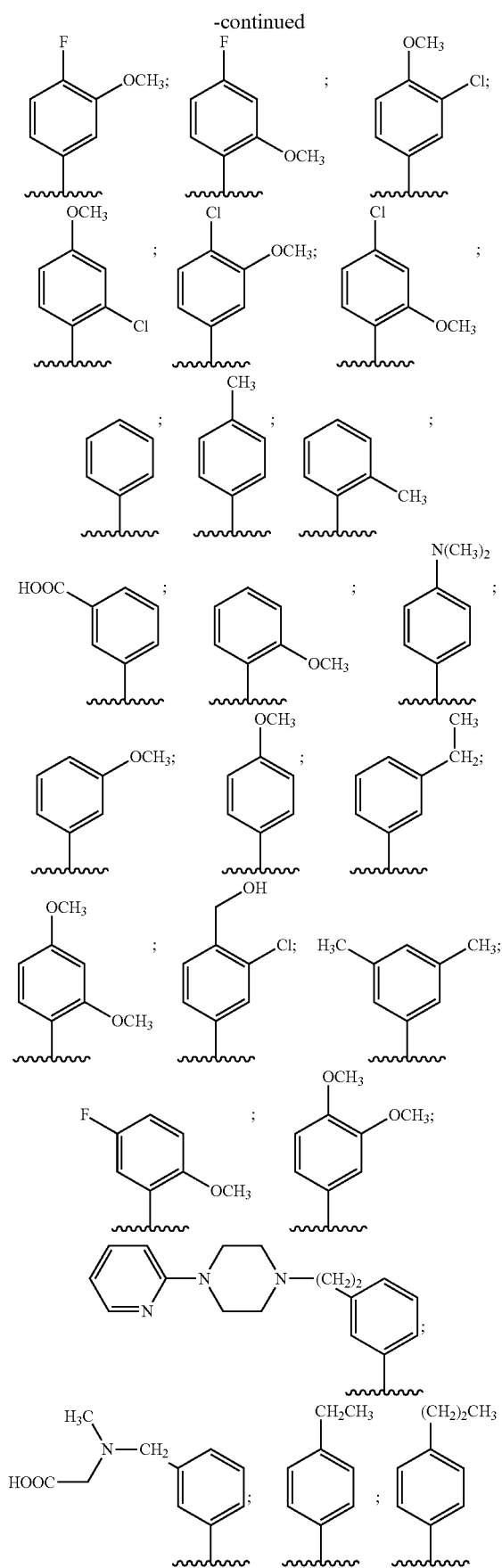
-continued
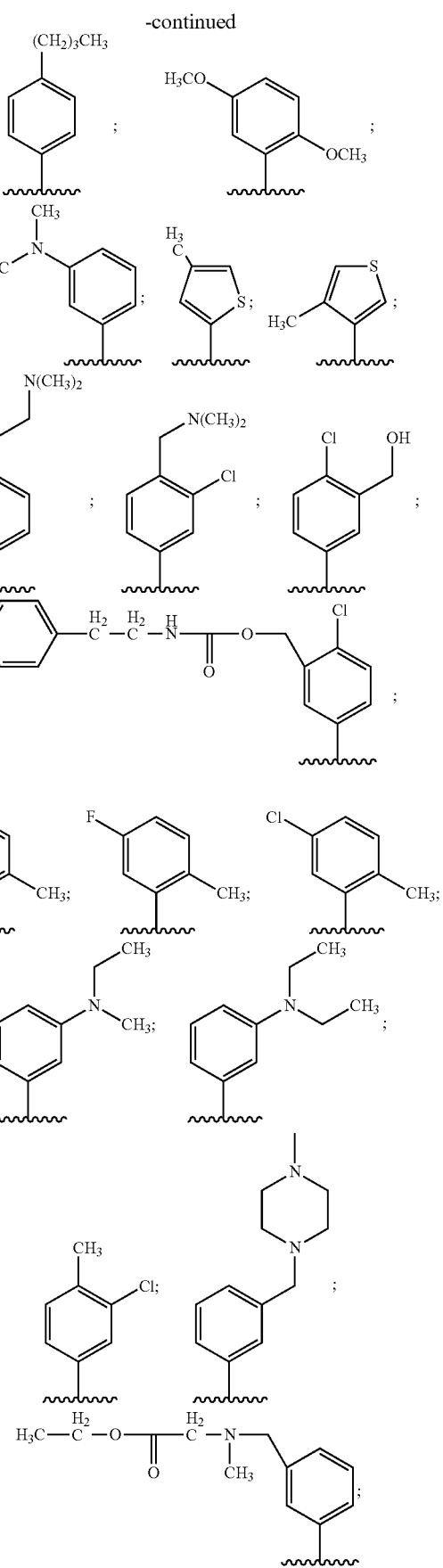

-continued
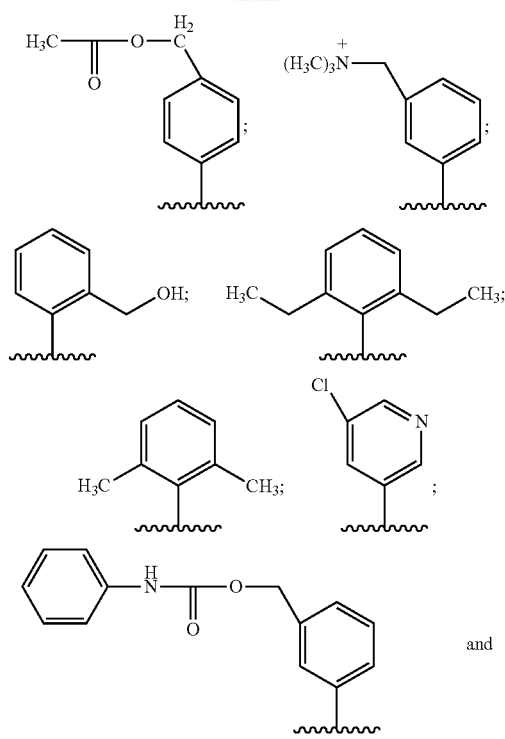
22. The compound of claim 12, wherein $M^1$ is F, R* is a member selected from:
-continued
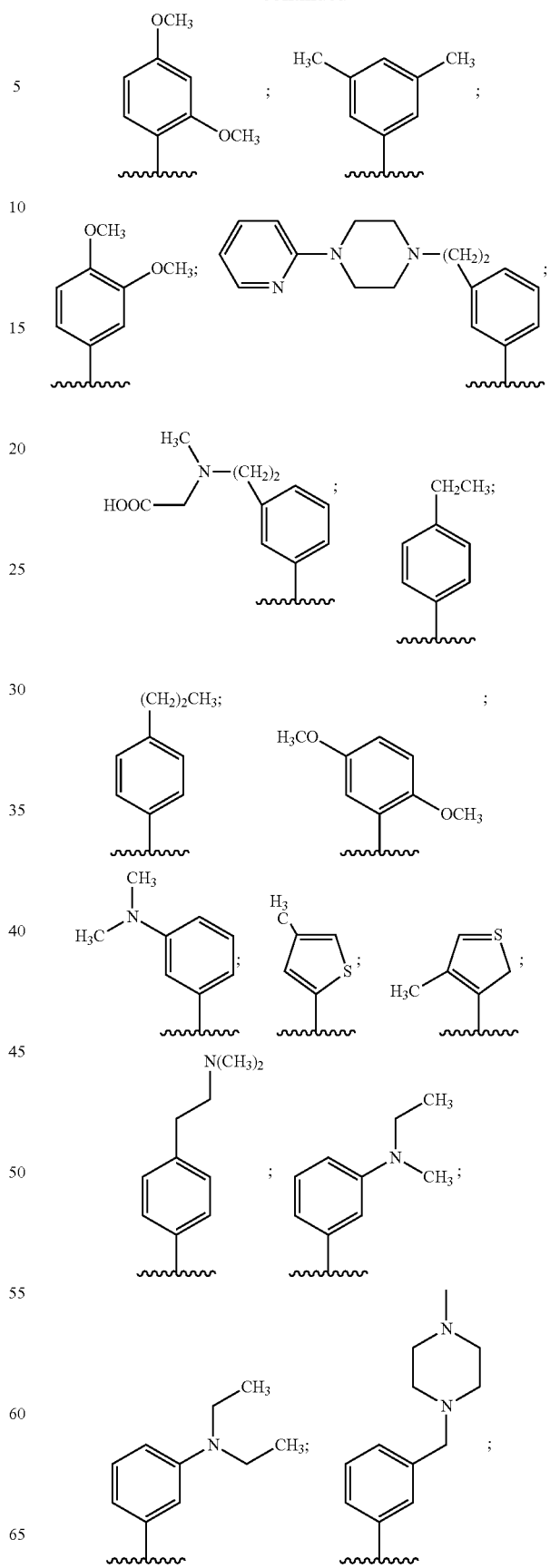

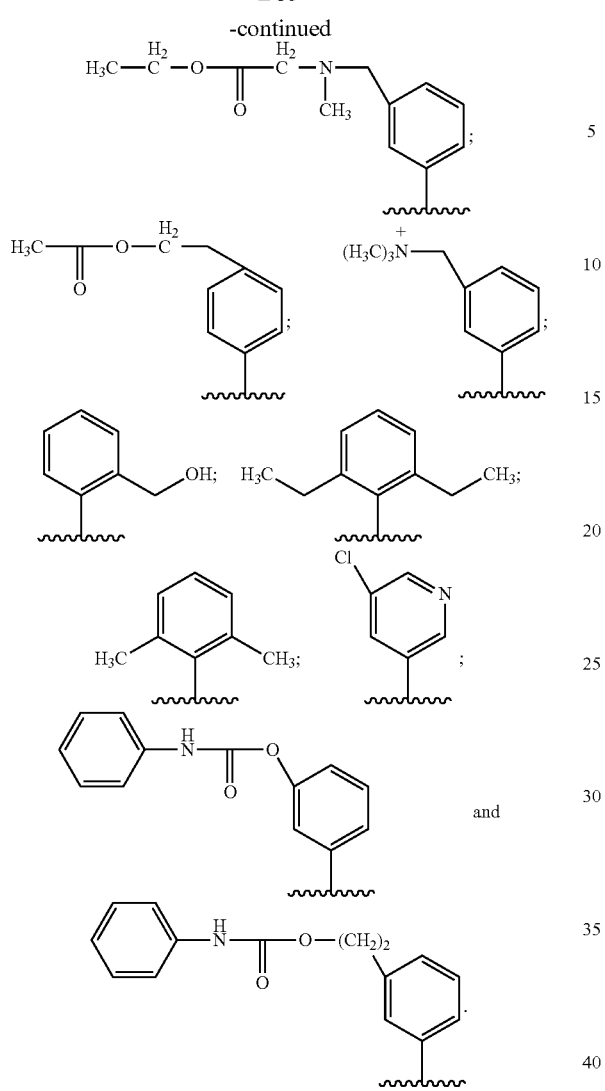
23. A compound of a structure which is a member selected from:
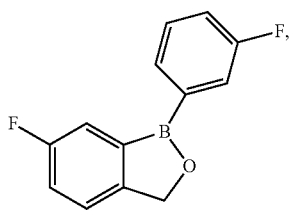
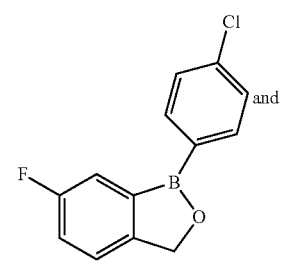
and
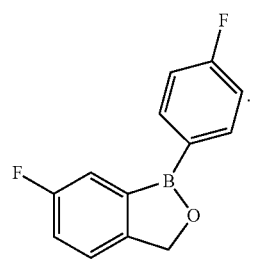
* * * * *